US010065928B2

(12) United States Patent
Zuo et al.

(10) Patent No.: US 10,065,928 B2
(45) Date of Patent: Sep. 4, 2018

(54) QUINOLINONE COMPOUND AND USE THEREOF

(71) Applicant: Sunshine Lake Pharma Co., Ltd., Dongguan, Guangdong (CN)

(72) Inventors: Yinglin Zuo, Dongguan (CN); Xiaojun Wang, Dongguan (CN); Yingjun Zhang, Dongguan (CN); Liang Wen, Dongguan (CN); Shoutao Wu, Dongguan (CN); Xiaofeng Yuan, Dongguan (CN)

(73) Assignee: SUNSHINE LAKE PHARMA CO., LTD., Dongguan, Guangdong (CN)

( * ) Notice: Subject to any disclaimer, the term of this patent is extended or adjusted under 35 U.S.C. 154(b) by 0 days.

(21) Appl. No.: 15/502,499

(22) PCT Filed: Sep. 1, 2015

(86) PCT No.: PCT/CN2015/088799
§ 371 (c)(1),
(2) Date: May 4, 2017

(87) PCT Pub. No.: WO2016/034108
PCT Pub. Date: Mar. 10, 2016

(65) Prior Publication Data
US 2017/0247332 A1    Aug. 31, 2017

(30) Foreign Application Priority Data

Sep. 2, 2014 (CN) .......................... 2014 1 0442574

(51) Int. Cl.
| C07D 215/56 | (2006.01) |
| C07D 215/54 | (2006.01) |
| C07D 401/04 | (2006.01) |
| C07D 401/12 | (2006.01) |
| C07D 413/12 | (2006.01) |
| A61P 9/10 | (2006.01) |
| A61P 7/06 | (2006.01) |

(52) U.S. Cl.
CPC ............. *C07D 215/56* (2013.01); *A61P 7/06* (2018.01); *A61P 9/10* (2018.01); *C07D 215/54* (2013.01); *C07D 401/04* (2013.01); *C07D 401/12* (2013.01); *C07D 413/12* (2013.01); *H05K 999/99* (2013.01)

(58) Field of Classification Search
CPC .. C07D 215/56; C07D 413/12; C07D 401/04; C07D 401/12; C07D 215/54; A61P 9/10; A61P 7/06
See application file for complete search history.

(56) References Cited

U.S. PATENT DOCUMENTS

| 7,323,475 | B2 | 1/2008 | Arend et al. |
| 7,569,726 | B2 | 8/2009 | Allen et al. |
| 7,608,621 | B2 | 10/2009 | Shaw et al. |
| 7,635,715 | B2 | 12/2009 | Allen et al. |
| 7,696,223 | B2 | 4/2010 | Deng et al. |
| 7,728,130 | B2 * | 6/2010 | Allen .................... C07D 215/22 544/105 |
| 7,811,595 | B2 | 10/2010 | Kawamoto et al. |
| 7,897,612 | B2 | 3/2011 | Fitch et al. |
| 7,928,120 | B2 | 4/2011 | Arend et al. |
| 8,012,968 | B2 * | 9/2011 | Allen .................... C07D 215/22 514/235.2 |
| 8,030,346 | B2 | 10/2011 | Allen et al. |
| 8,048,892 | B2 | 11/2011 | Allen et al. |
| 8,048,894 | B2 | 11/2011 | Allen et al. |
| 8,217,043 | B2 | 7/2012 | Deng et al. |
| 8,252,817 | B2 | 8/2012 | Flamme et al. |
| 8,269,008 | B2 | 9/2012 | Arend et al. |
| 8,283,465 | B2 | 10/2012 | Mitani et al. |
| 8,324,208 | B2 | 12/2012 | Duffy et al. |
| 8,324,405 | B2 | 12/2012 | Ho et al. |
| 8,372,863 | B2 | 2/2013 | Clements et al. |
| 8,389,520 | B2 | 3/2013 | Thede et al. |
| 8,445,680 | B2 | 5/2013 | Debenham et al. |
| 8,471,024 | B2 | 6/2013 | Colandrea et al. |
| 8,541,430 | B2 | 9/2013 | Srivastava et al. |
| 8,703,795 | B2 | 4/2014 | Turtle et al. |
| 8,742,138 | B2 | 6/2014 | Kang et al. |
| 8,796,263 | B2 | 8/2014 | Rabinowitz et al. |
| 8,815,884 | B2 | 8/2014 | Fitch et al. |
| 8,865,713 | B2 | 10/2014 | Hocutt et al. |
| 8,865,748 | B2 | 10/2014 | Shalwitz et al. |
| 8,883,823 | B2 | 11/2014 | Witschi et al. |

(Continued)

FOREIGN PATENT DOCUMENTS

| WO | 2007038571 | * | 4/2007 |
| WO | 2007038571 | A2 | 4/2007 |

(Continued)

OTHER PUBLICATIONS

Murry, J Combinatorial Chemistry, vol. 12(5), 676-686, 2010.*
Chowdhury, Rasheduzzaman et al., Selective Small Molecule Probes for the Hypoxia Inducible Factor (HIF) Prolyl Hydroxylases, Chem. Biol., May 7, 2013, pp. 1488-1496, vol. 8.
Murray, Justin K. et al., Dipeptidyl-Quinolone Derivatives Inhibit Hypoxia Inducible Factor-1 a Prolyl Hydroxylase-1, -2 and -3 with Altered Selectivity, Journal of Combinatorial Chemistry, Jul. 28, 2010, pp. 676-686, vol. 12, No. 05.
ISR of PCT/CN2015/088799.

(Continued)

*Primary Examiner* — D Margaret M Seaman
(74) *Attorney, Agent, or Firm* — Kam Wah Law

(57) ABSTRACT

Provided herein are a quinolinone compound, pharmaceutical composition thereof, and use of the compound or the pharmaceutical composition in drug preparation, the drug being used to prevent, manage, treat or relieve diseases related to HIF and/or EPO of a patient, including anemia, vascular disease, myocardial ischemia, dysmetabolism, or for wound healing.

13 Claims, No Drawings

(56) References Cited

U.S. PATENT DOCUMENTS

| | | |
|---|---|---|
| 8,921,389 B2 | 12/2014 | Ng et al. |
| 8,927,591 B2 | 1/2015 | Ho et al. |
| 8,937,078 B2 | 1/2015 | Bembenek et al. |
| 8,952,160 B2 | 2/2015 | Zhou et al. |
| 9,145,366 B2 | 9/2015 | Lanthier et al. |
| 9,238,637 B2 | 1/2016 | Kang et al. |
| 9,340,511 B2 | 5/2016 | Thompson et al. |
| 9,394,300 B2 * | 7/2016 | Desai .................. C07D 409/04 |
| 9,409,892 B2 | 8/2016 | Ho et al. |
| 9,422,240 B2 | 8/2016 | Takayama et al. |
| 2008/0171756 A1 | 7/2008 | Shaw |
| 2009/0176825 A1 | 7/2009 | Fitch et al. |
| 2010/0056563 A1 | 3/2010 | Guiadeen et al. |
| 2010/0298324 A1 | 11/2010 | Gotchev et al. |
| 2010/0305133 A1 | 12/2010 | Colon et al. |
| 2010/0305154 A1 | 12/2010 | Fitch |
| 2011/0028507 A1 | 2/2011 | Kim et al. |
| 2011/0039895 A1 | 2/2011 | Chai et al. |
| 2011/0098324 A1 | 4/2011 | Brackley, III et al. |
| 2011/0144167 A1 | 6/2011 | Tedesco |
| 2011/0160227 A1 | 6/2011 | Shaw et al. |
| 2015/0239889 A1 | 8/2015 | Nakajima et al. |
| 2016/0002170 A1 | 1/2016 | Witschi et al. |

FOREIGN PATENT DOCUMENTS

| | | |
|---|---|---|
| WO | 2009039321 A1 | 3/2009 |
| WO | 2009039322 A1 | 3/2009 |
| WO | 2009039323 A1 | 3/2009 |
| WO | 2009049112 A1 | 4/2009 |
| WO | 2009134847 A1 | 11/2009 |
| WO | 2011045811 A1 | 4/2011 |
| WO | 2011048611 A1 | 4/2011 |
| WO | 2011056725 A1 | 5/2011 |

OTHER PUBLICATIONS

English translation of ISR.
Written Opinion of PCT/CN2015/088799.
English translation of Written Opinion.

* cited by examiner

QUINOLINONE COMPOUND AND USE THEREOF

CROSS-REFERENCE TO RELATED APPLICATIONS

This is a U.S. national stage application of the International Patent Application No. PCT/CN2015/088799, filed Sep. 1, 2015, which claims priority to Chinese Patent Application No. 201410442574.4, filed Sep. 2, 2014, both of which are incorporated herein by reference in their entireties.

FIELD

The invention belongs to the pharmaceutical field, specifically, it relates to a novel quinolinone compound and pharmaceutical composition thereof. Furthermore, it relates to use of the compound and pharmaceutical composition thereof in the manufacture of medicaments.

BACKGROUND

Under the cases of anemia, trauma, tissue necrosis and defect, tissues or cells are often in a hypoxia state. Hypoxia leads to the transcriptional induction of a series of genes that participate in angiogenesis, iron metabolism, glucose metabolism, cell growth and proliferation. Wherein, hypoxia inducible factor (HIF) is a transcription factor activating in the case of oxygen reduction of somatic cell, and is widely distributed in various parts of the body, especially in endangium, heart, brain, kidney, liver, etc. HIF is a heterodimer containing an oxygen-regulated α-subunit (HIFα), and a constitutively expressed β-subunit (HIFβ/ARNT). In oxygenated (normoxic) cells, HIFα subunits are rapidly degraded by a mechanism that involves ubiquitination by the von Hippel-Lindau tumor suppressor (pVHL) E3 ligase complex. Under hypoxic conditions, HIFα is not degraded, and an active HIFα/β complex accumulates in the nucleus, and activates the expression of several genes including glycolytic enzymes, glucose transporters, erythropoietin (EPO), and vascular endothelial growth factor (VEGF).

Erythropoietin (EPO), a naturally occurring hormone that is produced in response to HIFα, stimulates the production of red blood cells (erythrocytes), which carry oxygen throughout the body. EPO is normally secreted by the kidneys, and endogenous EPO is increased under conditions of reduced oxygen (hypoxia). All types of anemia are characterized by the blood's reduced capacity to carry oxygen, and thus are associated with similar signs and symptoms, including pallor of the skin and mucous membranes, weakness, dizziness, easy fatigability, and drowsiness, leading to a decrease in quality of life. Anemia is typically associated with a condition in which the blood is deficient in red blood cells or in hemoglobin. Common causes of anemia include deficiencies of iron, vitamin B12, and folic acid. Anemia can also develop in association with chronic diseases, e.g., inflammatory disorders, including disorders with consequent inflammatory suppression of marrow, etc. Anemia also associates with renal dysfunction, and most dialysis patients with renal failure often suffer from chronic anemia.

Prolyl hydroxylase domain (PHD) is a key factor regulating HIF. Under a constant oxygen condition, PHD can hydroxylate two key proline residue Pro402 and Pro564 of HIF alpha to increase its affinity with pVHL and accelerate the degradation process. Under hypoxia and other pathological conditions, PHD-catalyzed HIF reaction is blocked, and the speed of proteolytic degradation slows, which results in intracellular accumulation of HIF a, thereby causes a series of adaptive cellular response to hypoxia. Using PHD inhibitors to inhibit PHD and extend the action time of HIF, thereby to increase the expression of EPO and other genes, which can effectively treat and prevent HIF-related and/or EPO-related disorders, such as anemia, ischemic and hypoxic conditions.

SUMMARY OF THE INVENTION

The invention provides a novel quinolinone compound as an HIF-PHD inhibitor and pharmaceutical composition thereof, and use of the compound and pharmaceutical composition thereof in the manufacture of a medicament; wherein the medicament is used for preventing, managing, treating or lessening a disease in a patient wherein the disease is related to HIF and/or EPO, such as anemia. etc.

In one aspect, provided herein is a compound having Formula (I) or a stereoisomer, a geometric isomer, a tautomer, an N-oxide, a hydrate, a solvate, a metabolite, an ester, a pharmaceutically acceptable salt or a prodrug thereof,

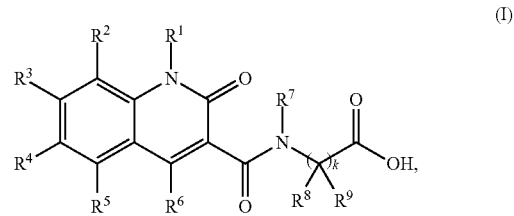

wherein, $R^1$ is H or $C_{1-4}$ alkyl, and wherein the $C_{1-4}$ alkyl is optionally substituted with one, two, three or four substituents independently selected from oxo (=O), halogen, amino, hydroxy, mercapto, cyano, $C_{1-4}$ alkyl, $C_{2-4}$ alkenyl, $C_{1-4}$ haloalkyl, $C_{1-4}$ alkoxy, acyl, sulfonyl, $C_{3-6}$ cycloalkyl, $C_{2-5}$ heterocyclyl or $C_{1-5}$ heteroaryl;

each of $R^2$, $R^3$, $R^4$ and $R^5$ is independently H or -L-$R_{10}$, with the proviso that $R^2$, $R^3$, $R^4$ and $R^5$ are not H at the same time;

wherein each L is independently —$(CR^{11}R^{12})_m$—, —$(CR^{11}R^{12})_p$—O—, —$(CR^{11}R^{12})_p$—S(=O)—, —$(CR^{11}R^{12})_p$—N($R^{13}$)—, —$(CR^{11}R^{12})_p$—C(=X)—, —$(CR^{11}R^{12})_p$—C(=X)N($R^{13}$)—$(CR^{11}R^{12})_q$—, —$(CR^{11}R^{12})_p$—C(=X)O—$(CR^{11}R^{12})_q$—, —$(CR^{11}R^{12})_p$—OC(=X)N($R^{13}$)—$(CR^{11}R^{12})_q$—, —$(CR^{11}R^{12})_p$—N($R^{13}$)C(=X)N($R^{13}$)—$(CR^{11}R^{12})_q$—, —$(CR^{11}R^{12})_p$—S(=O)$_2$N($R^{13}$)—$(CR^{11}R^{12})_q$—, —$(CR^{11}R^{12})_p$—S(=O)$_2$O—$(CR^{11}R^{12})_q$—, $C_{3-10}$ cycloalkylene, $C_{2-9}$ heterocyclylene or $C_{1-9}$ heteroarylene, and wherein optionally each of the $C_{3-10}$ cycloalkylene, $C_{2-9}$ hererocyclylene and $C_{1-9}$ heteroarylene is independently substituted with one, two, three or four substituents independently selected from oxo (=O), hydroxy, mercapto, amino, nitro, cyano, halogen, $C_{1-6}$ alkyl, $C_{1-6}$ haloalkyl, $C_{1-6}$ alkoxy, $C_{1-6}$ haloalkoxy, acyl, sulfonyl, $C_{3-10}$ cycloalkyl, $C_{2-9}$ heterocyclyl, $C_{6-10}$ aryl or $C_{1-9}$ hereroaryl;

wherein each X is independently O or S;

each $R^{11}$ and $R^{12}$ is independently H, halogen, cyano, hydroxy, mercapto, amino, $C_{1-6}$ alkyl, $C_{1-6}$ haloalkyl, $C_{1-6}$ alkoxy, $C_{1-6}$ haloalkoxy, $C_{3-10}$ cycloalkyl, $C_{2-9}$ heterocyclyl, $C_{6-10}$ aryl or $C_{1-9}$ heteroaryl, and wherein optionally each of the hydroxy, mercapto, amino, $C_{1-6}$ alkyl, $C_{1-6}$ haloalkyl, $C_{1-6}$ alkoxy, $C_{1-6}$ haloalkoxy, $C_{3-10}$ cycloalkyl, $C_{2-9}$ heterocyclyl, $C_{6-10}$ aryl and $C_{1-9}$ heteroaryl is independently substituted with one, two, three or four substituents independently selected from oxo (=O), halogen, hydroxy, amino, $C_{1-6}$ alkyl, $C_{1-6}$ haloalkyl, $C_{1-6}$ alkoxy, $C_{1-6}$ haloalkoxy, acyl, sulfonyl, $C_{3-8}$ cycloalkyl, $C_{2-7}$ heterocyclyl, $C_{6-10}$ aryl or $C_{1-9}$ heteroaryl;

each $R^{13}$ is independently H, $C_{1-6}$ alkyl, $C_{3-10}$ cycloalkyl, $C_{2-9}$ heterocyclyl, $C_{6-10}$ aryl or $C_{1-9}$ heteroaryl, and wherein optionally each of the $C_{1-6}$ alkyl, $C_{3-10}$ cycloalkyl, $C_{2-9}$ heterocyclyl, $C_{6-10}$ aryl and $C_{1-9}$ heteroaryl is independently substituted with one, two, three or four substituents independently selected from oxo (=O), cyano, nitro, halogen, hydroxy, amino, mercapto, $C_{1-6}$ alkyl, $C_{1-6}$ haloalkyl, $C_{1-6}$ alkoxy, $C_{1-6}$ haloalkoxy, acyl, sulfonyl, $C_{3-8}$ cycloalkyl, $C_{2-7}$ heterocyclyl, $C_{6-10}$ aryl or $C_{1-9}$ heteroaryl;

each $R^{10}$ is independently —$OR^{14}$, —$NR^{15}R^{16}$, —C(=O)$NR^{15}R^{16}$, —N($R^{15}$)C(=O)$R^{17}$, —C(=O)$R^{17}$, —S(=O)$R^{18}$, —S(=O)$_2NR^{15}R^{16}$, —N($R^{15}$)S(=O)$_2R^{18}$, $C_{3-10}$ cycloalkyl, $C_{3-10}$ cycloalkyl-$C_{1-6}$-alkyl, $C_{2-9}$ heterocyclyl, $C_{2-9}$ heterocyclyl-$C_{1-6}$-alkyl, $C_{6-10}$ aryl, $C_{6-10}$ aryl-$C_{1-6}$-alkyl, $C_{1-9}$ heteroaryl or $C_{1-9}$ heteroaryl-$C_{1-6}$-alkyl, and wherein optionally each of the $C_{3-10}$ cycloalkyl, $C_{3-10}$ cycloalkyl-$C_{1-6}$-alkyl, $C_{2-9}$ heterocyclyl, $C_{2-9}$ heterocyclyl-$C_{1-6}$-alkyl, $C_{6-10}$ aryl, $C_{6-10}$ aryl-$C_{1-6}$-alkyl, $C_{1-9}$ heteroaryl and $C_{1-9}$ heteroaryl-$C_{1-6}$-alkyl is independently substituted with one, two, three or four substituents independently selected from oxo (=O), halogen, hydroxy, mercapto, amino, nitro, cyano, $C_{1-6}$ alkyl, $C_{1-6}$ haloalkyl, $C_{1-6}$ alkoxy, $C_{1-6}$ haloalkoxy, acyl, sulfonyl, $C_{3-10}$ cycloalkyl, $C_{2-9}$ heterocyclyl, $C_{6-10}$ aryl or $C_{1-9}$ heteroaryl;

wherein, each $R^{14}$, $R^{16}$, $R^{17}$ and $R^{18}$ is independently $C_{3-10}$ cycloalkyl, $C_{3-10}$ cycloalkyl-$C_{1-6}$-alkyl, $C_{2-9}$ heterocyclyl, $C_{2-9}$ heterocyclyl-$C_{1-6}$-alkyl, $C_{6-10}$ aryl, $C_{6-10}$ aryl-$C_{1-6}$-alkyl, $C_{1-9}$ heteroaryl or $C_{1-9}$ heteroaryl-$C_{1-6}$-alkyl, and wherein optionally each of the $C_{3-10}$ cycloalkyl, $C_{3-10}$ cycloalkyl-$C_{1-6}$-alkyl, $C_{2-9}$ heterocyclyl, $C_{2-9}$ heterocyclyl-$C_{1-6}$-alkyl, $C_{6-10}$ aryl, $C_{6-10}$ aryl-$C_{1-6}$-alkyl, $C_{1-9}$ heteroaryl and $C_{1-9}$ heteroaryl-$C_{1-6}$-alkyl is independently substituted with one, two, three or four substituents independently selected from oxo (=O), halogen, hydroxy, amino, nitro, cyano, $C_{1-4}$ alkyl, $C_{1-4}$ haloalkyl, $C_{1-4}$ alkoxy, $C_{1-4}$ haloalkoxy, acyl or sulfonyl;

each $R^{15}$ is independently H or $C_{1-6}$ alkyl, and wherein the $C_{1-6}$ alkyl is independently and optionally substituted with one, two, three or four substituents independently selected from oxo (=O), halogen, $C_{1-4}$ alkyl, $C_{1-4}$ haloalkyl, amino, $C_{1-4}$ alkoxy, $C_{1-4}$ haloalkyl, $C_{3-6}$ cycloalkyl, $C_{2-5}$ heterocyclyl, $C_{6-10}$ aryl or $C_{1-5}$ heteroaryl;

$R^6$ is H, hydroxy, mercapto, amino or $C_{1-4}$ alkyl;

$R^7$ is H or $C_{1-4}$ alkyl, and wherein the $C_{1-4}$ alkyl is independently and optionally substituted with one, two, three or four substituents independently selected from halogen, amino, hydroxy, $C_{1-4}$ alkyl, $C_{1-4}$ alkoxy, $C_{3-6}$ cycloalkyl, $C_{2-5}$ heterocyclyl, $C_{6-10}$ aryl or $C_{1-5}$ heteroaryl;

each $R^8$ and $R^9$ is independently H or $C_{1-4}$ alkyl, and wherein the $C_{1-4}$ alkyl is independently and optionally substituted with one, two, three or four substituents independently selected from halogen, amino, hydroxy, $C_{1-4}$ alkyl, $C_{1-4}$ alkoxy, $C_{3-6}$ cycloalkyl, $C_{2-5}$ heterocyclyl, $C_{6-10}$ aryl or $C_{1-5}$ heteroaryl;

k is 1, 2, 3 or 4;

each m is independently 1, 2, 3 or 4;

each n is independently 0, 1 or 2; and each p and q is independently 0, 1, 2, 3 or 4.

In certain embodiments, the compound disclosed herein, wherein each L is independently —(CR$^{11}$R$^{12}$)$_m$—, —(CR$^{11}$R$^{12}$)$_p$—O—, —(CR$^{11}$R$^{12}$)$_p$—S(O)—, —(CR$^{11}$R$^{12}$)$_p$—N(R$^{13}$)—, —(CR$^{11}$R$^{12}$)$_p$—C(O)N(R$^{13}$)—(CR$^{11}$R$^{12}$)$_q$—, $C_{3-8}$ cycloalkylene, $C_{2-7}$ heterocyclylene or $C_{1-5}$ heteroarylene, and wherein optionally each of the $C_{3-8}$ cycloalkylene, $C_{2-7}$ heterocyclylene and $C_{1-5}$ heteroarylene is independently substituted with one, two, three or four substituents independently selected from oxo (=O), hydroxy, mercapto, —NH$_2$, methylamino, dimethylamino, nitro, cyano, fluorine, chlorine, bromine, methyl, ethyl, propyl, n-butyl, t-butyl, trifluoromethyl, methoxy, ethoxy, trifluoromethoxy, acetyl, methoxycarbonyl, carbamoyl, methyl sulfonyl, aminosulfonyl, methoxysulfonyl, cyclopropyl, cyclohexyl, piperidyl, morpholinyl, phenyl, naphthyl, pyrrolyl, thienyl or pyridyl;

wherein each $R^{11}$ and $R^{12}$ is independently H, fluorine, chlorine, bromine, $C_{1-4}$ alkyl, $C_{1-4}$ haloalkyl, $C_{3-6}$ cycloalkyl, $C_{2-5}$ heterocyclyl, $C_{6-10}$ aryl or $C_{1-5}$ heteroaryl, and wherein optionally each of the $C_{1-4}$ alkyl, $C_{1-4}$ haloalkyl, $C_{3-6}$ cycloalkyl, $C_{2-5}$ heterocyclyl, $C_{6-10}$ aryl and $C_{1-5}$ heteroaryl is independently substituted with one, two, three or four substituents independently selected from oxo (=O), fluorine, chlorine, bromine, hydroxy, —NH$_2$, methylamino, dimethylamino, methyl, ethyl, propyl, n-butyl, t-butyl, trifluoromethyl, methoxy, trifluoromethoxy, cyclopropyl, cyclopentyl, cyclohexyl, pyrrolidyl, piperidyl, morpholinyl, phenyl, naphthyl, pyrrolyl, thienyl or pyridyl;

each $R^{13}$ is independently H, $C_{1-4}$ alkyl, $C_{3-6}$ cycloalkyl, $C_{2-5}$ heterocyclyl, $C_{6-10}$ aryl or $C_{1-5}$ heteroaryl, and wherein optionally each of the $C_{1-4}$ alkyl, $C_{3-6}$ cycloalkyl, $C_{2-5}$ heterocyclyl, $C_{6-10}$ aryl and $C_{1-5}$ heteroaryl is independently substituted with one, two, three or four substituents independently selected from oxo (=O), cyano, nitro, fluorine, chlorine, bromine, hydroxy, —NH$_2$, methylamino, dimethylamino, methyl, ethyl, propyl, n-butyl, t-butyl, trifluoromethyl, methoxy, trifluoromethoxy, acetyl, methyl sulfonyl, cyclopropyl, cyclopentyl, cyclohexyl, pyrrolidyl, piperidyl, morpholinyl, phenyl or pyridyl.

In certain embodiments, the compound disclosed herein, wherein each L is independently —(CR$^{11}$R$^{12}$)$_m$—, —O—, —S(=O)—, —N(R$^{13}$)—, —(CR$^{11}$R$^{12}$)$_p$—C(=O)N(R$^{13}$)—(CR$^{11}$R$^{12}$)$_q$—, $C_{3-6}$ cycloalkylene, $C_{2-5}$ heterocyclylene or $C_{1-5}$ heteroarylene, and wherein optionally each of the $C_{3-6}$ cycloalkylene, $C_{2-5}$ heterocyclylene and $C_{1-5}$ heteroarylene is independently substituted with one, two, three or four substituents independently selected from oxo (=O), hydroxy, mercapto, —NH$_2$, methylamino, dimethylamino, nitro, cyano, fluorine, chlorine, bromine, methyl, ethyl, propyl, n-butyl, t-butyl, trifluoromethyl, methoxy, ethoxy, trifluoromethoxy, acetyl, carbamoyl, methyl sulfonyl, aminosulfonyl or methoxysulfonyl;

wherein each $R^{11}$ and $R^{12}$ is independently H, $C_{1-4}$ alkyl, $C_{3-6}$ cycloalkyl, $C_{2-5}$ heterocyclyl, $C_{6-10}$ aryl or $C_{1-5}$ heteroaryl, and wherein optionally each of the $C_{1-4}$ alkyl, $C_{3-6}$ cycloalkyl, $C_{2-5}$ heterocyclyl, $C_{6-10}$ aryl or $C_{1-5}$ heteroaryl is independently substituted with one, two, three or four substituents independently selected from fluorine, chlorine, bromine, hydroxy, —NH$_2$, methyl, ethyl, propyl, n-butyl, t-butyl, trifluoromethyl, methoxy, trifluoromethoxy, cyclopropyl, cyclopentyl, cyclohexyl, pyrrolidyl, piperidyl, morpholinyl, phenyl, pyrrolyl or pyridyl;

each $R^{13}$ is independently H or $C_{1-4}$ alkyl, and wherein the $C_{1-4}$ alkyl is optionally substituted with one, two, three or four substituents independently selected from cyano, nitro, fluorine, chlorine, bromine, hydroxy, —NH$_2$, methylamino, dimethylamino, methyl, ethyl, trifluoromethyl, methoxy, trifluoromethoxy, acetyl, methyl sulfonyl, cyclopropyl, cyclopentyl, cyclohexyl, pyrrolidyl, piperidyl, morpholinyl, phenyl or pyridyl.

In certain embodiments, the compound disclosed herein, wherein each $R^{10}$ is independently $C_{3-8}$ cycloalkyl, $C_{3-8}$ cycloalkyl-$C_{1-4}$-alkyl, $C_{2-7}$ heterocyclyl, $C_{2-7}$ heterocyclyl-$C_{1-4}$-alkyl, $C_{6-10}$ aryl, $C_{6-10}$ aryl-$C_{1-4}$-alkyl, $C_{1-9}$ heteroaryl or $C_{1-9}$ heteroaryl-$C_{1-4}$-alkyl, and wherein optionally each of the $C_{3-8}$ cycloalkyl, $C_{3-8}$ cycloalkyl-$C_{1-4}$-alkyl, $C_{2-7}$ heterocyclyl, $C_{2-7}$ heterocyclyl-$C_{1-4}$-alkyl, $C_{6-10}$ aryl, $C_{6-10}$ aryl-$C_{1-4}$-alkyl, heteroaryl and $C_{1-9}$ heteroaryl-$C_{1-4}$-alkyl is independently substituted with one, two, three or four substituents independently selected from oxo (=O), fluorine, chlorine, bromine, hydroxy, —$NH_2$, methylamino, dimethylamino, nitro, cyano, $C_{1-4}$ alkyl, $C_{1-4}$ haloalkyl, $C_{1-4}$ alkoxy, $C_{1-4}$ haloalkoxy, acyl, sulfonyl, $C_{3-6}$ cycloalkyl, $C_{2-5}$ heterocyclyl, $C_{6-10}$ aryl or $C_{1-9}$ heteroaryl.

In certain embodiments, the compound disclosed herein, wherein each $R^{10}$ is independently $C_{3-6}$ cycloalkyl, $C_{2-5}$ heterocyclyl, $C_{6-10}$ aryl or $C_{1-9}$ heteroaryl, and wherein optionally each of the $C_{3-6}$ cycloalkyl, $C_{2-5}$ heterocyclyl, $C_{6-10}$ aryl and $C_{1-9}$ heteroaryl is independently substituted with one, two, three or four substituents independently selected from oxo (=O), fluorine, chlorine, bromine, hydroxy, —$NH_2$, methylamino, dimethylamino, nitro, cyano, methyl, ethyl, propyl, n-butyl, t-butyl, trifluoromethyl, methoxy, ethoxy, trifluoromethoxy, acetyl, methoxycarbonyl, carbamoyl, methyl sulfonyl, aminosulfonyl, methoxysulfonyl, cyclopropyl, cyclohexyl, pyrrolidyl, piperidyl, morpholinyl, oxomorpholinyl, phenyl, naphthyl, pyrrolyl, thienyl, pyridyl, pyrimidyl or quinolyl.

In certain embodiments, provided herein is a compound having Formula (II) or a stereoisomer, a geometric isomer, a tautomer, an N-oxide, a hydrate, a solvate, a metabolite, a ester, a pharmaceutically acceptable salt or a prodrug thereof,

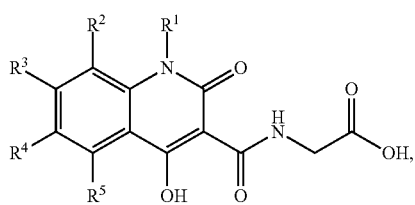

(II)

wherein $R^1$, $R^2$, $R^3$, $R^4$ and $R^5$ are as defined herein.

In certain embodiments, the compound disclosed herein, wherein each L is independently —($CR^{11}R^{12}$)—, —($CR^{11}R^{12}$)$_2$—, —O—, —S(=O)$_2$—, —C(=O)N($R^{13}$)—, —($CR^{11}R^{12}$)—C(=O)N($R^{13}$)—, —C(=O)N($R^{13}$)—($CR^{11}R^{12}$)—, —($CR^{11}R^{12}$)—C(=O)N($R^{13}$)—($CR^{11}R^{12}$)—, cyclopentylene, cyclohexylene, pyrrolidylene, pyrazolidylene, oxazolidinylene, piperidylene, tetrahydropyrimidinylene, oxotetrahydropyrimidinylene, piperazinylene, oxazinanylene, thiazolylene, pyrrolylene, thienylene, furylene, pyrazolylene, imidazolylene, pyridylene, pyrimidinylene or pyrazinylene, and wherein optionally each of the cyclopentylene, cyclohexylene, pyrrolidylene, pyrazolidylene, oxazolidinylene, piperidylene, tetrahydropyrimidinylene, oxotetrahydropyrimidinylene, piperazinylene, oxazinanylene, thiazolylene, pyrrolylene, thienylene, furylene, pyrazolylene, imidazolylene, pyridylene, pyrimidinylene and pyrazinylene is independently substituted with one, two, three or four substituents independently selected from oxo (=O), hydroxy, —$NH_2$, methylamino, dimethylamino, nitro, cyano, fluorine, chlorine, bromine, methyl, ethyl, propyl, n-butyl, t-butyl, trifluoromethyl, methoxy, ethoxy, trifluoromethoxy, acetyl, carbamoyl, methyl sulfonyl, aminosulfonyl or methoxysulfonyl;

wherein each $R^{11}$ and $R^{12}$ is independently H, methyl, ethyl, propyl, butyl, cyclopropyl, cyclopentyl, cyclohexyl, pyrrolidyl, piperidyl, morpholinyl, phenyl or pyridyl, and wherein optionally each of the methyl, ethyl, propyl, butyl, cyclopropyl, cyclopentyl, cyclohexyl, pyrrolidyl, piperidyl, morpholinyl, phenyl and pyridyl is independently substituted with one, two, three or four substituents independently selected from fluorine, chlorine, bromine, hydroxy, —$NH_2$, methylamino, dimethylamino, methyl, ethyl, trifluoromethyl, methoxy or trifluoromethoxy; and each $R^{13}$ is independently H, methyl, ethyl, propyl or butyl.

In certain embodiments, each $R^{10}$ is independently cyclopropyl, cyclopentyl, cyclohexyl, oxiranyl, pyrrolidyl, pyrazolidyl, oxazolidinyl, piperidyl, morpholinyl, tetrahydropyrimidinyl, piperazinyl, oxazinanyl, phenyl, 2,3-dihydro-1H-indenyl, naphthyl, pyrrolyl, pyrazolyl, furyl, imidazolyl, oxazolyl, thienyl, thiazolyl, pyridinyl, pyrimidinyl, indolyl, dihydroindolyl, quinolyl, isoquinolyl, quinazolinyl, imidazopyridinyl, benzimidazolyl, benzofuranyl or benzothienyl, and wherein optionally each of the cyclopropyl, cyclopentyl, cyclohexyl, oxiranyl, pyrrolidyl, pyrazolidyl, oxazolidinyl, piperidyl, morpholinyl, tetrahydropyrimidinyl, piperazinyl, oxazinanyl, phenyl, 2,3-dihydro-1H-indenyl, naphthyl, pyrrolyl, pyrazolyl, furyl, imidazolyl, oxazolyl, thienyl, thiazolyl, pyridinyl, pyrimidinyl, indolyl, dihydroindolyl, quinolyl, isoquinolyl, quinazolinyl, imidazopyridinyl, benzimidazolyl, benzofuranyl and benzothienyl is independently substituted with one, two, three or four substituents independently selected from oxo (=O), fluorine, chlorine, bromine, hydroxy, —$NH_2$, methylamino, dimethylamino, nitro, cyano, methyl, ethyl, propyl, n-butyl, t-butyl, trifluoromethyl, methoxy, ethoxy, trifluoromethoxy, acetyl, methoxycarbonyl, carbamoyl, methyl sulfonyl, aminosulfonyl, methoxysulfonyl, cyclopropyl, cyclopentyl, cyclohexyl, pyrrolidyl, piperidyl, morpholinyl, oxomorpholinyl, phenyl, pyrrolyl, thienyl or pyridyl.

In other aspect, provided herein is a pharmaceutical composition comprising the compound disclosed herein.

In certain embodiments, the pharmaceutical composition disclosed herein further comprises at least one of pharmaceutically acceptable carriers, excipients, diluents, adjuvants and vehicles.

In one aspect, provided herein is use of the compound or the pharmaceutical composition disclosed herein in the manufacture of a medicament for preventing, managing, treating or lessening a disease in a patient wherein the disease is related to hypoxia inducible factor and/or erythropoietin.

In certain embodiments, the use disclosed herein, wherein the medicament is used for preventing, managing, treating or lessening a disease in a patient wherein the disease is mediated at least in part by hypoxia inducible factor (HIF) prolyl hydroxylase.

In certain embodiments, the use disclosed herein, wherein the disease is anemia, ischemia, a vascular disease, angina pectoris, myocardial ischemia, myocardial infarction, a metabolic disorder or wound healing.

In another aspect, provided herein is the compound or the pharmaceutical composition disclosed herein in preventing, managing, treating or lessening a disease in a patient wherein the disease is related to hypoxia inducible factor and/or erythropoietin.

In certain embodiments, the compound or the composition disclosed herein is for use in preventing, managing, treating or lessening a disease in a patient wherein the disease is mediated at least in part by hypoxia inducible factor prolyl hydroxylase.

In other embodiments, the compound or the composition disclosed herein, wherein the disease is anemia, ischemia, a vascular disease, angina pectoris, myocardial ischemia, myocardial infarction, a metabolic disorders or wound healing.

In another aspect, provided herein is a method for preventing, managing, treating or lessening a disease in a patient wherein the disease is related to hypoxia inducible factor and/or erythropoietin comprising administering to the patient a therapeutically effective amount of the compound or the pharmaceutical composition disclosed herein.

In certain embodiments, the method disclosed herein is a method for preventing, managing, treating or lessening a disease in a patient wherein the disease is mediated at least in part by hypoxia inducible factor (HIF) prolyl hydroxylase.

In other embodiments, the method disclosed herein, wherein the disease is anemia, ischemia, a vascular disease, angina pectoris, myocardial ischemia, myocardial infarction, a metabolic disorders or wound healing.

DETAILED DESCRIPTION OF THE INVENTION

Definitions and General Terminology

Reference will now be made in detail to certain embodiments of the invention, examples of which are illustrated in the accompanying structures and formulas. The invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described herein. In the event that one or more of the incorporated literature, patents, and similar materials differs from or contradicts this application, including but not limited to defined terms, term usage, described techniques, or the like, this application controls.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

Unless defined otherwise, all technical and scientific terms used herein have the same meaning as is commonly understood by one skilled in the art to which this invention belongs. All patents and publications referred to herein are incorporated by reference in their entirety.

As used herein, the following definitions shall be applied unless otherwise indicated. For purposes of this invention, the chemical elements are identified in accordance with the *Periodic Table of the Elements*, CAS version, and the *Handbook of Chemistry and Physics*, 75th Ed. 1994. Additionally, general principles of organic chemistry are described in "*Organic Chemistry*", Thomas Sorrell, University Science Books, Sausalito: 1999, and "*March's Advanced Organic Chemistry*" by Michael B. Smith and Jerry March, John Wiley & Sons, New York: 2007, the entire contents of which are hereby incorporated by reference.

The grammatical articles "a", "an" and "the", as used herein, are intended to include "at least one" or "one or more" unless otherwise indicated herein or clearly contradicted by the context. Thus, the articles are used herein to refer to one or more than one (i.e. at least one) of the grammatical objects of the article. By way of example, "a component" means one or more components, and thus, possibly, more than one component is contemplated and may be employed or used in an implementation of the described embodiments.

As used herein, "patient" refers to a human (including adults and children) or other animal. In one embodiment, "patient" refers to a human.

The term "comprise" is an open expression, it means comprising the contents disclosed herein, but don't exclude other contents.

"Stereoisomers" refers to compounds which have identical chemical constitution, but differ with regard to the arrangement of the atoms or groups in space. Stereoisomers include enantiomer, diastereomers, conformer (rotamer), geometric (cis/trans) isomer, atropisomer, etc.

"Enantiomers" refers to two stereoisomers of a compound which are non-superimposable mirror images of one another.

"Diastereomer" refers to a stereoisomer with two or more centers of chirality and whose molecules are not mirror images of one another. Diastereomers have different physical properties, e.g., melting points, boiling points, spectral properties or biological activities. Mixture of diastereomers may separate under high resolution analytical procedures such as electrophoresis and chromatography such as HPLC.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "*Stereochemistry of Organic Compounds*", John Wiley & Sons, Inc., New York, 1994.

Any asymmetric atom (e.g., carbon or the like) of the compound(s) disclosed herein can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration.

Any resulting mixtures of stereoisomers can be separated on the basis of the physicochemical differences of the constituents, into the pure or substantially pure geometric isomers, enantiomers, diastereomers, for example, by chromatography and/or fractional crystallization.

The term "tautomer" or "tautomeric form" refers to structural isomers of different energies which are interconvertible via a low energy barrier. Where tautomerization is possible (e.g. in solution), a chemical equilibrium of tautomers can be reached. For example, proton tautomers (also known as prototropic tautomers) include interconversions via migration of a proton, such as keto-enol and imine-enamine isomerizations. Valence tautomers include interconversions by reorganization of some of the bonding electrons. A specific example of keto-enol tautomerization is the interconversion of pentane-2,4-dione and 4-hydroxypent-3- en-2-one tautomers. Another example of tautomerization is phenol-keto tautomerization. The specific example of phenol-keto tautomerisms is pyridin-4-ol and pyridin-4(1H)-one tautomerism. Unless otherwise stated, all tautomeric forms of the compounds disclosed herein are within the scope of the invention.

As described herein, the compounds disclosed herein may optionally be substituted with one or more substituents, such as are illustrated by the general formula of compound, or as exemplified by particular classes, subclasses, and species of the invention.

It will be appreciated that the phrase "optionally substituted" is used interchangeably with the phrase "substituted or unsubstituted". In general, the term "substituted" refers to the replacement of one or more hydrogen radicals in a given structure with the radical of a specified substituent. The phrase "optionally substituted" refers to that the structure or group may be unsubstituted or substituted with one or more specific substituent groups. Unless otherwise indicated, an optionally substituted group may have a substituent at each substitutable position of the group. When more than one position in a given structure can be substituted with more than one substituent selected from a specified group, the substituent may be either the same or different at each position. Wherein the substituent may be, but are not limited to, oxo (=O), hydrogen, deuterium, cyano, nitro, halogen, hydroxy, mercapto, amino, alkyl, haloalkyl, alkoxy, haloalkoxy, acyl, acyloxy, sulfonyl, sulfinyl, carboxy, cycloalkyl, cycloalkylalkyl, cycloalkyloxy, heterocyclyl, heterocyclylalkyl, heterocyclyloxy, aryl, arylalkyl, aryloxy, heteroaryl, heteroarylalkyl, heteroaryloxy, etc.

The term "optional" or "optionally" refers to that a subsequently described event or circumstance may but need not occur, and that the description includes instances where the event or circumstance occurs and instances in which it does not. For example, " . . . is optionally substituted with one, two, three or four substituents independently selected from . . . " includes the instance that the group is substituted with one, two, three or four substituents described herein and the instance that the group is unsubstituted. Furthermore, when the group is substituted with one or more substituents described herein, these substituents are independent of each other, i.e., one or more substituents described herein may be different from each other or the same.

At various places in the present specification, substituents of the compounds disclosed herein are disclosed in groups or in ranges. It is specifically intended that the invention include each and every individual subcombination of the members of such groups and ranges. For example, term "$C_1$-$C_6$ alkyl" or "$C_{1-6}$ alkyl" is specifically intended to individually disclose methyl, ethyl, $C_3$ alkyl, $C_4$ alkyl, $C_5$ alkyl, and $C_6$ alkyl; "$C_{1-4}$ alkyl" is specifically intended to individually disclose methyl, ethyl, $C_3$ alkyl (i.e., propyl, including n-propyl and i-propyl), $C_4$ alkyl (i.e., butyl, including n-butyl, i-butyl, sec-butyl and t-butyl).

At various places in the present specification, linking substituents are described. Where the structure clearly requires a linking group, the Markush variables listed for that group are understood to be linking groups. For example, if the structure requires a linking group and the Markush group definition for that variable lists "alkyl" or "aryl" then it is understood that the "alkyl" or "aryl" represents a linking alkylene group or arylene group, respectively.

The term "alkyl" or "alkyl group" refers to a saturated linear or branched-chain monovalent hydrocarbon group of 1-20 carbon atoms, wherein the alkyl group is optionally substituted with one or more substituents described herein. In some embodiments, the alkyl group contains 1-12 carbon atoms. In other embodiments, the alkyl group contains 1-6 carbon atoms. In still other embodiments, the alkyl group contains 1-4 carbon atoms. In yet other embodiments, the alkyl group contains 1-3 carbon atoms.

Further embodiments of the alkyl group include, but are not limited to, methyl, ethyl, n-propyl, isopropyl, n-butyl, isobutyl, sec-butyl, tert-butyl, n-pentyl, 2-pentyl, 3-pentyl, 2-methyl-2-butyl, 3-methyl-2-butyl, 3-methyl-1-butyl, 2-methyl-1-butyl, n-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, n-heptyl, n-octyl, and the like.

In some specific structures, the alkyl group acts as a linking group, it should be understood that the alkyl group represents a linking alkylene group. For example, the $C_{1-6}$ alkyl group in $C_{3-10}$ cycloalkyl-$C_{1-6}$-alkyl should be understood as $C_{1-6}$ alkylene.

The term "alkylene" refers to a saturated divalent hydrocarbon group derived from a straight or branched chain saturated hydrocarbon by the removal of two hydrogen atoms. Unless otherwise specified, the alkylene group contains 1-12 carbon atoms. In some embodiments, the alkylene group contains 1-6 carbon atoms. In other embodiments, the alkylene group contains 1-4 carbon atoms. In still other embodiments, the alkylene group contains 1-3 carbon atoms. In yet other embodiments, the alkylene group contains 1-2 carbon atoms. Such examples include methylene (—$CH_2$—), ethylene (including —$CH_2CH_2$— or —CH($CH_3$)—), isopropylene (including —CH($CH_3$)$CH_2$— or —CH($CH_3$)$_2$—), and the like. Wherein, the cycloalkyl group may be optionally substituted with one or more substituents disclosed herein.

The term "alkenyl" refers to linear or branched-chain monovalent hydrocarbon radical of 2 to 12 carbon atoms with at least one site of unsaturation, i.e., a carbon-carbon, $sp^2$ double bond, wherein the alkenyl radical may be optionally substituted with one or more substituents described herein, and includes radicals having "cis" and "trans" orientations, or alternatively, "F" and "Z" orientations. In some embodiments, the alkenyl group contains 2 to 8 carbon atoms. In other embodiments, the alkenyl group contains 2 to 6 carbon atoms. In still other embodiments, the alkenyl group contains 2 to 4 carbon atoms. Examples of alkenyl group include, but are not limited to, ethylenyl or vinyl (—CH=$CH_2$), allyl (—$CH_2$CH=$CH_2$), and the like.

The term "alkoxy" refers to an alkyl group, as previously defined, attached to the parent molecular moiety via an oxygen atom. Some non-limiting examples of the alkoxy group include methoxy, ethoxy, 1-propoxy, 2-propoxy, 1-butoxy, etc.

The term "haloalkyl" or "haloalkoxy" refers to alkyl or alkoxy, as the case may be, substituted with one or more halogen atoms. Some non-limiting examples of "haloalkyl" or "haloalkoxy" group include trifluoromethyl, trifluoromethoxy, and the like.

The term "amino" refers to —$NR^aR^b$, and wherein each of $R^a$ and $R^b$ is independently H, alkyl, cycloalkyl, cycloalkylalkyl, heterocyclyl, heterocyclylalkyl, aryl, arylalkyl, heteroaryl, heteroarylalkyl, acyl or sulfonyl, etc. Wherein, alkyl, cycloalkyl, cycloalkylalkyl, heterocyclyl, heterocyclylalkyl, aryl, arylalkyl, heteroaryl, heteroarylalkyl, acyl and sulfonyl are as described herein; and wherein the amino may be optionally substituted with one or more substituents described herein. Examples of such group include, but are not limited to, —$NH_2$, methylamino (—NHCH$_3$), dimethylamino (—N(CH$_3$)$_2$), ethylamino (—NHCH$_2$CH$_3$), phenylamino (—NHPh), pyridylamino, acetamino, methylsulfonyl, etc.

The term "cycloalkyl" refers to a monovalent or multivalent saturated or partially unsaturated ring having 3 to 12 ring carbon atoms as a monocyclic, bicyclic, or tricyclic ring system, and wherein the cycloalkyl is nonaromatic and the aromatic ring does not exist in the cycloalkyl system. In some embodiments, the cycloalkyl contains 3 to 10 ring carbon atoms, such as C$_{3-10}$ cycloalkyl. In other embodiments, the cycloalkyl contains 3 to 8 ring carbon atoms, such as C$_{3-8}$ cycloalkyl. In yet other embodiments, the cycloalkyl contains 3 to 6 ring carbon atoms, such as C$_{3-6}$ cycloalkyl. Some examples of cycloalkyl include, but are not limited to, cyclopropyl, cyclobutyl, cyclopentyl, cyclohexyl, cycloheptyl, cyclooctyl, etc.; wherein the C$_{3-6}$ cycloalkyl includes cyclopropyl, cyclobutyl, cyclopentyl, cyclohexyl. Wherein the cycloalkyl group may be optionally substituted with one or more substituents disclosed herein.

The term "cycloalkylalkyl" refers to a cycloalkyl group attached to the rest of the molecule via an alkyl group, wherein the cycloalkyl and alkyl are as defined herein. In the specification, the description "C$_{3-10}$ cycloalkyl-C$_{1-6}$-alkyl" or "C$_{3-10}$ cycloalkyl-C$_{1-4}$ alkyl" etc., refers to the C$_{3-10}$ cycloalkyl attached to the rest of molecular via C$_{1-6}$ alkyl or C$_{1-4}$ alkyl group. The "cycloalkylalkyl" group may be optionally substituted with one or more substituents disclosed herein. Some non-limiting examples of the cycloalkylalkyl group include cyclopropylmethyl, cyclopropylethyl, cyclopentylmethyl, cyclohexylmethyl, cyclohexylethyl, etc.

The term "cycloalkyloxy" refers to a cycloalkyl group, attached to the rest part of the molecule via an oxygen atom. Wherein the cycloalkyl group is as defined herein. The cycloalkyloxy group may be optionally substituted with one or more substituents disclosed herein. Some non-limiting examples of the cycloalkyloxy group include cyclopropoxy, cyclopentyl oxy and cyclohexyloxy, etc.

The term "heterocyclyl" refers to a saturated or partially unsaturated monocyclic, bicyclic or tricyclic ring system having 3 to 12 ring atoms in which at least one ring atom is selected from nitrogen, sulfur and oxygen; and wherein the heterocyclyl is nonaromatic, and the aromatic ring does not exist in the heterocyclyl system. Unless otherwise specified, the heterocyclyl group may be carbon or nitrogen linked, and a —CH$_2$— group can be optionally replaced by a —C(=O)— group. In which, the sulfur can be optionally oxygenized to S-oxide and the nitrogen can be optionally oxygenized to N-oxide. The heterocyclyl group may be optionally substituted with one or more substituents disclosed herein.

In some embodiments, the heterocyclyl group may be a C$_{2-9}$ heterocyclyl group, which refers to a heterocyclyl group containing 2 to 9 ring carbon atoms and at least one ring heteroatom selected from nitrogen, sulfur and oxygen. In other embodiments, the heterocyclyl group may be a C$_{2-7}$ heterocyclyl group, which refers to a heterocyclyl group containing 2 to 7 ring carbon atoms and at least one ring heteroatom selected from nitrogen, sulfur and oxygen. In still other embodiments, the heterocyclyl group may be a C$_{2-5}$ heterocyclyl group, which refers to a heterocyclyl group containing 2 to 5 ring carbon atoms and at least one ring heteroatom selected from nitrogen, sulfur and oxygen. Some non-limiting examples of the heterocyclyl group include oxiranyl, thietanyl, pyrrolidinyl, pyrazolinyl, pyrazolidinyl, imidazolinyl, imidazolidinyl, oxazolidinyl, tetrahydrofuranyl, dihydrothienyl, dihydropyranyl, piperidinyl (or piperidyl), morpholinyl, tetrahydropyrimidinyl, oxazinanyl, thiomorpholinyl and piperazinyl, etc. A —CH$_2$— group of the heterocyclyl group may be substituted with —C(=O)—, some non-limiting examples of such group include 2-oxopyrrolidinyl, 2-piperidinonyl, 3-morpholinonyl, 3-thiomorpholinonyl and oxotetrahydropyrimidinyl, etc.

The term "heterocyclylalkyl" refers to a heterocyclyl group attached to the rest of the molecule via an alkyl group, wherein the heterocyclyl and alkyl are as defined herein. In the specification, the description "C$_{2-9}$ heterocyclyl-C$_{1-6}$-alkyl" etc., refers to the C$_{2-9}$ heterocyclyl attached to the rest of the molecular via a C$_{1-6}$ alkyl group. The "heterocyclylalkyl" group may be optionally substituted with one or more substituents disclosed herein. Some non-limiting examples of such group include pyrrolidinylmethyl, piperidinylmethyl, piperidinylethyl, morpholinylmethyl and morpholinylethyl, etc.

The term "heterocyclyloxy" refers to a heterocyclyl group attached to the rest of the molecule via an oxygen atom, and wherein the heterocyclyl is as defined herein. The "heterocyclyloxy" group may be optionally substituted with one or more substituents disclosed herein. Some non-limiting examples of the heterocyclyloxy group include pyrrolidinyloxy, morpholinyloxy, piperidyloxy, etc.

The term "halogen" refers to fluorine (F), chlorine (Cl), bromine (Br) or iodine (I).

The term "aryl" refers to monocyclic, bicyclic and tricyclic carbocyclic ring systems having a total of six to fourteen ring members, or six to twelve ring members, or six to ten ring members, wherein at least one ring in the system is aromatic, and the aryl group has a single point or multipoint of attachment to the rest of the molecule. The term "aryl" and "aromatic ring" can be used interchangeably herein. Some non-limiting examples of the aryl group include phenyl, 2,3-dihydro-1H-indenyl, naphthalenyl and anthracenyl, etc. The aryl group may be optionally substituted with one or more substituents disclosed herein. Unless otherwise specified, the group "C$_{6-14}$ aryl" refers to an aryl group having 6-14 ring carbon atoms.

The term "arylalkyl" or "aralkyl" refers to an aryl group attached to the rest of the molecule via an alkyl group, wherein the aryl and alkyl are as defined herein. The "arylalkyl" group may be optionally substituted with one or more substituents disclosed herein. Some non-limiting examples of such group include benzyl, phenylethyl and naphthylmethyl, etc.

The term "aryloxy" refers to an aryl group, attached to the rest part of the molecule via an oxygen atom. Wherein the aryl group is as defined herein. The aryloxy group may be optionally substituted with one or more substituents disclosed herein. Some non-limiting examples of such group include phenoxy and naphthyloxy, etc.

The term "heteroaryl" refers to monocyclic, bicyclic and tricyclic carbocyclic ring systems having a total of five to twelve ring members, or five to ten ring members, or five to six ring members, wherein at least one ring in the system is aromatic, and in which at least one ring member is selected from nitrogen, sulfur and oxygen, and wherein the heteroaryl has a single point or multipoint of attachment to the rest of the molecule. When —CH$_2$— group exists in heteroaryl, the —CH$_2$— can be optionally replaced by —C(=O)—. Unless otherwise specified, the heteroaryl group can attach to the rest of the molecular via any reasonable attachments (such as carbon atom of CH, or nitrogen atom of NH). The term "heteroaryl" and "heteroaromatic ring" or "heteroaromatic compound" can be used interchangeably herein. In some embodiments, the heteroaryl group may be a $C_{1-9}$ heteroaryl group, which refers to a heteroaryl group containing 1 to 9 ring carbon atoms and at least one ring heteroatom selected from nitrogen, sulfur and oxygen. In other embodiments, the heteroaryl group may be a $C_{1-7}$ heteroaryl group, which refers to a heteroaryl group containing 1 to 7 ring carbon atoms and at least one ring heteroatom selected from nitrogen, sulfur and oxygen. In still other embodiments, the heteroaryl group may be a $C_{1-6}$ heteroaryl group, which refers to a heteroaryl group containing 1 to 6 ring carbon atoms and at least one ring heteroatom selected from nitrogen, sulfur and oxygen. In other embodiments, the heteroaryl group may be a $C_{1-5}$ heteroaryl group, which refers to a heteroaryl group containing 1 to 5 ring carbon atoms and at least one ring heteroatom selected from nitrogen, sulfur and oxygen. In still other embodiments, the heteroaryl group may be a $C_{1-4}$ heteroaryl group, which refers to a heteroaryl group containing 1 to 4 ring carbon atoms and at least one ring heteroatom selected from nitrogen, sulfur and oxygen. In yet other embodiments, the heteroaryl group may be a $C_{1-3}$ heteroaryl group, which refers to a heteroaryl group containing 1 to 3 ring carbon atoms and at least one ring heteroatom selected from nitrogen, sulfur and oxygen. Some non-limiting examples of such group include furanyl, imidazolyl, isoxazolyl, oxazolyl, pyrrolyl, pyrazolyl, pyridyl, pyrimidinyl, pyridazinyl, pyrazinyl, thienyl, thiazolyl, etc., and also include the following bicycle ring: benzimidazolyl, benzofuranyl, benzothiophenyl, indolyl, oxoindolyl, indolinyl, imidazopyridyl, pyrazopryridyl, pyrazopyrimidinyl, quinolyl, isoquinolyl and quinazolinyl, etc. The heteroaryl group may be optionally substituted with one or more substituents disclosed herein.

The term "heteroarylalkyl" refers to a heteroaryl group attached to the rest of the molecule via an alkyl group, wherein the heteroaryl and alkyl are as defined herein. The "heteroarylalkyl" group may be optionally substituted with one or more substituents disclosed herein. Some non-limiting examples of such group included pyridylmethyl, pyrrolylethyl and quinolylmethyl, etc.

The term "heteroaryloxy" refers to a heteroaryl group attached to the rest of the molecule via an oxygen atom, wherein the heteroaryl is as defined herein. The heteroaryloxy group may be optionally substituted with one or more substituents disclosed herein. Some non-limiting examples of such group include pyridyloxy and pyrimidyloxy, etc.

The term "acyl" refers to —C(═O)—R, and wherein the substituent R is attached to the rest of molecular via carbonyl (—C(═O)—); wherein the R is the substituent described herein, including but not limited to, alkyl, alkoxy, hydroxy, amino, cycloalkyl, heterocyclyl, aryl, heteroaryl, etc. Wherein the alkyl, alkoxy, hydroxy, amino, cycloalkyl, heterocyclyl, aryl and heteroaryl are as described herein; examples of such group include, but are not limited to, acetyl (—C(═O)CH$_3$), carboxy (—C(═O)OH), methoxycarbonyl (—C(═O)OCH$_3$), carbamoyl (—C(═O)NH$_2$), phenylcarbonyl, etc.

The term "sulfonyl" refers to —S(═O)$_2$—R, and wherein the substituent R is attached to the rest of molecular via sulfonyl (—S(═O)$_2$—); wherein the R is the substituent described herein, including but not limited to, alkyl, alkoxy, hydroxy, amino, cycloalkyl, heterocyclyl, aryl, heteroaryl, etc. Wherein the alkyl, alkoxy, hydroxy, amino, cycloalkyl, heterocyclyl, aryl and heteroaryl are as described herein; examples of such group include, but are not limited to, sulfo (—S(═O)$_2$OH), methyl sulfonyl (—S(═O)$_2$CH$_3$), methoxysulfonyl (—S(═O)$_2$OCH$_3$), aminosulfonyl (—S(═O)$_2$NH$_2$), phenyl sulfonyl, etc.

The term "sulfinyl" refers to —S(═O)—R, and wherein the substituent R is attached to the rest of molecular via sulfonyl (—S(═O)—); wherein the R is the substituent described herein, including but not limited to, alkyl, alkoxy, hydroxy, amino, cycloalkyl, heterocyclyl, aryl, heteroaryl, etc. Wherein the alkyl, alkoxy, hydroxy, amino, cycloalkyl, heterocyclyl, aryl and heteroaryl are as described herein. Examples of such group include, but are not limited to, sulfinic acid group (—S(═O)OH), methylsulfinyl (—S(═O)CH$_3$), phenylsulfinyl, etc.

As described herein, a bond drawn from a substituent (R)$_n$ to the center of one ring within a ring system represents substitution of n substituents R at any substitutable position on the rings. For example, Formula a represents possible substitution of n substituents R in any of the position on ring B.

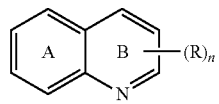

Formula a

As described herein, there has two attachment points on "—(CR$^{11}$R$^{12}$)$_p$—C(O)N(R$^{13}$)—(CR$^{11}$R$^{12}$)$_q$—" which can attach to the rest of molecular, and the two attachment points can exchange with each other. For example, when the L described in the specification is the group of Formula b, L (i. e., —(CR$^{11}$R$^{12}$)$_p$—C(═O)N(R$^{13}$)—(CR$^{11}$R$^{12}$)$_q$—) can attach to the rest of molecular via E endpoint or E' endpoint (such as the dihydroquinolinone skeleton of Formula (I)).

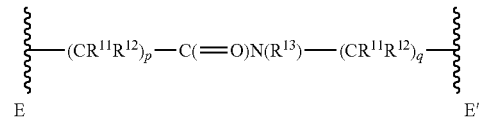

Formula b

In addition, the description of "each . . . is independently" and "each (of) . . . and . . . is independently" in the invention can be used interchangeably herein, unless otherwise specified. It should have a general understanding that each individual described herein is independent of each other, which is independently the same or different from each other. In more detail, the description of "each . . . is independently" and "each (of) . . . and . . . is independently" can be expressed both in different groups in which same symbols expressed specific options do not affect each other (for example, the specific options of R$^{11}$ in Formula "—(CR$^{11}$R$^{12}$)$_p$—" and "—(CR$^{11}$R$^{12}$)$_q$—" are not affected with each other) and the same groups in which same symbols expressed specific options do not affect each other (for example, when p is above 1, the specific options of each R$^{11}$ and each R$^{12}$ in Formula "—(CR$^{11}$R$^{12}$)$_p$—" are not affected with each other). The term "independently" in " . . . independently and optionally" also should be broadly understood.

The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" refers to molecular entities and compositions that approved by a regulatory agency of the Federal or a state government or listed in the U.S. Pharmacopeia or other generally recognized pharmacopeia for use in animals, and more particularly in humans.

The term "carrier" refers to a diluent, adjuvant, excipient, or substrate with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "*Remington's Pharmaceutical Sciences*" by E. W. Martin.

The term "prodrug" refers to a compound that is transformed in vivo into a compound of Formula (I). Such a transformation can be affected, for example, by hydrolysis of the prodrug form in blood or enzymatic transformation to the parent form in blood or tissue. Prodrugs of the compounds disclosed herein may be, for example, esters. Some common esters which have been utilized as prodrugs are phenyl esters, aliphatic ($C_1$-$C_{24}$) esters, acyloxymethyl esters, carbamates, carbamates and amino acid esters. For example, a compound disclosed herein that contains a hydroxy group may be acylated at this position to form its prodrug. Other prodrug forms include phosphates, such as, those phosphates resulting from the phosphonation of a hydroxy group on the parent compound. A thorough discussion of prodrugs is provided in T. Higuchi and V. Stella, *Pro-drugs as Novel Delivery Systems*, Vol. 14 of the A.C.S. Symposium Series, Edward B. Roche, ed., *Bioreversible Carriers in Drug Design*, American Pharmaceutical Association and Pergamon Press, 1987, J. Rautio et al., Prodrugs: Design and Clinical Applications, *Nature Review Drug Discovery*, 2008, 7, 255-270, and S. J. Hecker et al., Prodrugs of Phosphates and Phosphonates, *Journal of Medicinal Chemistry*, 2008, 51, 2328-2345, all of which are incorporated herein by reference in their entireties.

A "metabolite" is a product produced through metabolism in the body of a specified compound or salt thereof. The metabolites of a compound may be identified using routine techniques known in the art and their activities determined using tests such as those described herein. Such products may result for example from oxidation, reduction, hydrolysis, amidation, deamidation, esterification, deesterification, enzyme cleavage, and the like, of the administered compound. Accordingly, the invention includes metabolites of compounds disclosed herein, including compounds produced by a process comprising contacting a compound disclosed herein with a mammal for a period of time sufficient to yield a metabolic product thereof.

A "pharmaceutically acceptable salts" refers to organic or inorganic salts of a compound disclosed herein. Pharmaceutically acceptable salts are well known in the art. For example, S. M. Berge et al., describe pharmaceutically acceptable salts in detail in *J. Pharmaceutical Sciences*, 1977, 66: 1-19, which is incorporated herein by reference. Some non-limiting examples of pharmaceutically acceptable and nontoxic salts include salts formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid and malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, cyclopentanepropionate, digluconate, dodecyl sulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, laurylsulfate, malate, methanesulfonate, 2-naphthalenesulfonate, nicotinate, nitrate, oleate, palmitate, pamoate, pectinate, persulfate, 3-phenylpropionate, picrate, pivalate, propionate, stearate, thiocyanate, p-toluenesulfonate, undecanoate, valerate, and the like. Salts derived from appropriate bases include alkali metal, alkaline earth metal, ammonium and $N^+(C_{1-4}\ alkyl)_4$ salts. This invention also envisions the quaternization of any basic nitrogen-containing groups of the compounds disclosed herein. Water or oil soluble or dispersible products may be obtained by such quaternization. Representative alkali or alkaline earth metal used for forming salts include sodium, lithium, potassium, calcium, magnesium, and the like. Further pharmaceutically acceptable salts include, when appropriate, non-toxic ammonium, quaternary ammonium, and amine cations formed using counterions such as halide, hydroxide, carboxylate, sulfate, phosphate, nitrate, $C_{1-8}$ sulfonate or aryl sulfonate.

The term "solvate" refers to an association or complex of one or more solvent molecules and a compound disclosed herein. Examples of solvents that form solvates include, but are not limited to, water, isopropanol, ethanol, methanol, dimethylsulfoxide, ethyl acetate, acetic acid and ethanolamine. The term "hydrate" refers to the complex where the solvent molecule is water.

An "ester" refers to an in vivo hydrolysable ester of a compound of the Formula (I) containing hydroxy group or carboxy group, for example, a pharmaceutically acceptable ester which is hydrolysed in the human or animal body to produce the parent alcohol or acid. The compound of the Formula (I) having carboxy group can form a hydrolyzable ester in vivo with a appropriate group, such group includes, but are not limited to alkyl, arylalkyl, etc.

An "N-oxide" refers to one or more than one nitrogen atoms oxidised to form N-oxide(s), where a compound contains several amine functions. Particular examples of N-oxides are the N-oxides of a tertiary amine or a nitrogen atom of a nitrogen-containing heterocycle. N-oxides can be formed by treatment of the corresponding amine with an oxidizing agent such as hydrogen peroxide or a per-acid (e.g., a peroxycarboxylic acid) (See, *Advanced Organic Chemistry*, by Jerry March, 4th Edition, Wiley Interscience, pages). More particularly, N-oxides can be made by the procedure of L. W. Deady (*Syn. Comm.* 1977, 7, 509-514) in which the amine compound is reacted with m-chloroperoxybenzoic acid (MCPBA), for example, in an inert solvent such as dichloromethane.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment, "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

The term "disease related to erythropoietin (EPO)" or "erythropoietin-related condition" refers to any condition associated with below normal, abnormal, or inappropriate modulation of erythropoietin. Diseases related to erythropoietin (EPO) include any condition wherein an increase in EPO level would provide therapeutic benefit. Diseases related to erythropoietin (EPO) include, but are not limited to, such as anemia, including anemia associated with diabetes, ulcers, kidney failure, cancer, infection, dialysis, surgery, and chemotherapy and conditions involving ischemia and hypoxia such as occlusive arterial disease, angina pectoris, intestinal infarctions, pulmonary infarctions, cerebral ischemia, and myocardial infarction.

The term "disease related to hypoxia-inducible factor (HIF)" or "HIF-related condition" refers to any condition associated with below normal, abnormal, or inappropriate modulation of hypoxia-inducible factor (HIF). HIF-related conditions include any condition wherein an increase in HIF level would provide therapeutic benefit. Diseases related to hypoxia-inducible factor (HIF) include, but are not limited to, heart disease, stroke, peripheral vascular disease, ulcers, burns, chronic wounds, chronic ischemia, pulmonary embolism, ischemia—reperfusion injury, inflammation and anemia.

A disease related to erythropoietin (EPO) or hypoxia-inducible factor (HIF) includes, but is not limited to, anemia, ischemia, vascular disease, angina pectoris, myocardial ischemia, myocardial infarction, metabolic disorders or wound healing, etc.

"A disease mediated at least in part by HIF prolyl hydroxylase (HIF-PHD)" can be used interchangeably with "an HIF prolyl hydroxylase related disease", which refers to any condition associated with abnormal of HIF-PHD, including disease induced by abnormal of HIF-PHD. HIF-PHD related diseases include, but are not limited to, anemia and ischemia, etc.

The term "anemia" as used herein refers to any abnormality or insufficient in hemoglobin or erythrocyte that leads to reduced oxygen levels in the blood. Anemia can be associated with abnormal production, processing, or performance of erythrocytes and/or hemoglobin. The term anemia refers to any reduction in the number of red blood cells and/or level of hemoglobin in blood relative to normal blood levels. Anemia can arise due to various conditions such as acute or chronic kidney disease, infections, inflammation, cancer, irradiation, toxins, diabetes, and surgery. Infections may be due to, e.g., virus, bacteria, and/or parasites, etc. Inflammation may be due to infection, autoimmune disorders, such as rheumatoid arthritis, etc. Anemia can also be associated with blood loss due to, e.g., stomach ulcer, duodenal ulcer, hemorrhoids, cancer of the stomach or large intestine, trauma, injury, surgical procedures, etc. Anemia is further associated with radiation therapy, chemotherapy, and kidney dialysis. Anemia is also associated with HIV-infected patients undergoing treatment with azidothymidine (zidovudine) or other reverse transcriptase inhibitors, and can develop in cancer patients undergoing chemotherapy, e.g., with cyclic cisplatin- or non-cisplatin-containing chemotherapeutics. Aplastic anemia and myelodysplastic syndromes are diseases associated with bone marrow failure that result in decreased production of erythrocytes. Further, anemia can result from defective or abnormal hemoglobin or erythrocytes, such as in disorders including microcytic anemia, hypochromic anemia, etc. Anemia can result from disorders in iron transport, processing, and utilization, see, e.g., sideroblastic anemia, etc.

Any formula given herein is also intended to represent isotopically unenriched forms as well as isotopically enriched forms of the compounds. Isotopically enriched compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, sulfur, fluorine, and chlorine, such as $^2$H, $^3$H, $^{11}$C, $^{13}$C, $^{14}$C, $^{15}$N, $^{17}$O, $^{18}$O, $^{18}$F, $^{31}$P, $^{32}$P, $^{35}$S, $^{36}$Cl and $^{125}$I, respectively.

In another aspect, the compounds of the invention include isotopically enriched compounds as defined herein, for example those into which radioactive isotopes, such as $^3$H, $^{14}$C and $^{18}$F, or those into which non-radioactive isotopes, such as $^2$H and $^{13}$C are present. Such isotopically enriched compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F-enriched compound may be particularly desirable for PET or SPECT studies. Isotopically-enriched compounds of Formula (I) can generally be prepared by conventional techniques known to those skilled in the art or by processes analogous to those described in the accompanying Examples and Preparations using an appropriate isotopically-labeled reagent in place of the non-labeled reagent previously employed.

Further, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index. It is understood that deuterium in this context is regarded as a substituent of a compound of Formula (I) or Formula (II). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). Pharmaceutically acceptable solvates in accordance with the invention include those wherein the solvent of crystallization may be isotopically substituted, e.g., D$_2$O, d$_6$-acetone, DMSO-d$_6$.

Unless otherwise stated, all tautomeric forms of the compounds disclosed herein are within the scope of the invention. Additionally, unless otherwise stated, structures depicted herein are also meant to include compounds that differ only in the presence of one or more isotopically enriched atoms.

As used herein, the abbreviations for any protective groups, amino acids and other compounds are, unless otherwise indicated, in accord with their common usage, recognized abbreviations, or the IUPAC-IUB Commission on Biochemical Nomenclature (See, Biochem. 1972, 11: 942-944).

DESCRIPTION OF COMPOUNDS OF THE INVENTION

The invention provides a novel quinolinone compound as an HIF-PHD inhibitor and pharmaceutical composition thereof, and use of the compound or pharmaceutical composition thereof in the manufacture of a medicament; wherein the medicament is used for preventing, managing, treating or lessening a disease in a patient wherein the disease is related to HIF and/or EPO, such as anemia. etc.

In one aspect, provided herein is a compound having Formula (I) or a stereoisomer, a geometric isomer, a tautomer, an N-oxide, a hydrate, a solvate, a metabolite, an ester, a pharmaceutically acceptable salt or a prodrug thereof,

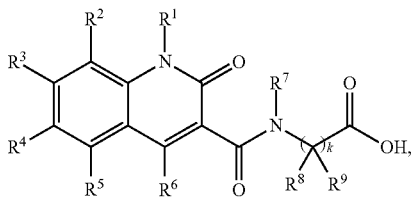

(I)

wherein $R^1$, $R^2$, $R^3$, $R^4$, $R^5$, $R^6$, $R^7$, $R^8$, $R^9$ and k are as defined herein.

In certain embodiments, $R^1$ is H, alkyl, cycloalkyl, heterocyclyl, aryl or heteroaryl; and wherein the alkyl is optionally substituted with one, two, three or four substituents independently selected from oxo (=O), halogen, amino, hydroxy, mercapto, cyano, alkyl, alkenyl, alkoxy, haloalkoxy, acyl, sulfonyl, sulfinyl, cycloalkyl, heterocyclyl or hereroaryl; wherein optionally each of the cycloalkyl, heterocyclyl, aryl and heteroaryl is independently substituted with one, two, three or four substituents independently selected from oxo (=O), cyano, halogen, alkyl, alkenyl, haloalkyl, amino, hydroxy, mercapto, alkoxy, haloalkoxy, acyl, sulfonyl, sulfinyl, cycloalkyl, heterocyclyl, aryl or heteroaryl.

In certain embodiments, each of $R^2$, $R^3$, $R^4$ and $R^5$ is independently H or -L-$R^{10}$, with the proviso that $R^2$, $R^3$, $R^4$ and $R^5$ are not H at the same time, and wherein L and $R^{10}$ are as defined herein.

In certain embodiments, each L is independently —(CR$^{11}$R$^{12}$)$_m$—, —(CR$^{11}$R$^{12}$)$_p$—O—, —(CR$^{11}$R$^{12}$)$_p$—S(=O)$_n$—, —(CR$^{11}$R$^{12}$)$_p$—N(R$^{13}$)—, —(CR$^{11}$R$^{12}$)$_p$—C(=X)—, —(CR$^{11}$R$^{12}$)$_p$—C(=X)N(R$^{13}$)—(CR$^{11}$R$^{12}$)$_q$—, —(CR$^{11}$R$^{12}$)$_p$—C(=X)O—(CR$^{11}$R$^{12}$)$_q$—, —(CR$^{11}$R$^{12}$)$_p$—OC(=X)N(R$^{13}$)—(CR$^{11}$R$^{12}$)$_q$, —(CR$^{11}$R$^{12}$)$_p$—N(R$^{13}$)C(=X)N(R$^{13}$)—(CR$^{11}$R$^{12}$)$_q$—, —(CR$^{11}$R$^{12}$)$_p$—S(=O)$_2$N(R$^{13}$)—(CR$^{11}$R$^{12}$)$_q$—, —(CR$^{11}$R$^{12}$)$_p$—S(=O)$_2$O—(CR$^{11}$R$^{12}$)$_q$—, cycloalkylene, heterocyclylene or heteroarylene, and wherein optionally each of the cycloalkylene, heterocyclylene and heteroarylene is independently substituted with one, two, three or four substituents independently selected from oxo (=O), hydroxy, mercapto, amino, nitro, cyano, halogen, alkyl, haloalkyl, alkoxy, haloalkoxy, acyl, sulfonyl, sulfinyl, cycloalkyl, heterocyclyl, aryl or heteroaryl;

wherein each X is independently O or S; and each $R^{11}$, $R^{12}$, $R^{13}$, m, n, p and q are as defined herein.

In certain embodiments, each $R^{11}$ and $R^{12}$ is independently H, halogen, cyano, hydroxy, mercapto, amino, alkyl, haloalkyl, alkoxy, haloalkoxy, cycloalkyl, heterocyclyl, aryl or heteroaryl; and wherein optionally each of the hydroxy, mercapto, amino, alkyl, haloalkyl, alkoxy, haloalkoxy, cycloalkyl, heterocyclyl, aryl and heteroaryl is independently substituted with one, two, three or four substituents independently selected from oxo (=O), halogen, hydroxy, amino, alkyl, haloalkyl, alkoxy, haloalkoxy, acyl, sulfonyl, sulfinyl, cycloalkyl, heterocyclyl, aryl or hereroaryl.

In certain embodiments, each $R^{13}$ is independently H, alkyl, cycloalkyl, heterocyclyl, aryl or heteroaryl, and wherein optionally each of the alkyl, cycloalkyl, heterocyclyl, aryl and heteroaryl is independently substituted with one, two, three or four substituents independently selected from oxo (=O), cyano, nitro, halogen, hydroxy, amino, mercapto, alkyl, haloalkyl, alkoxy, haloalkoxy, acyl, sulfonyl, sulfinyl, cycloalkyl, heterocyclyl, aryl or hereroaryl.

In certain embodiments, each $R^{10}$ is independently —OR$^{14}$, —NR$^{15}$R$^{16}$, —C(=O)NR$^{15}$R$^{16}$, —N(R$^{15}$)C(=O)R$^{17}$, —C(=O)R$^{17}$, —S(=O)R$^{18}$, —S(=O)$_2$NR$^{15}$R$^{16}$, —N(R$^{15}$)S(O)$_2$R$^{18}$, cycloalkyl, cycloalkylalkyl, heterocyclyl, heterocyclylalkyl, aryl, arylalkyl, heteroaryl or heteroarylalkyl, and wherein optionally each of the cycloalkyl, cycloalkylalkyl, heterocyclyl, heterocyclylalkyl, aryl, arylalkyl, heteroaryl and heteroarylalkyl is independently substituted with one, two, three or four substituents independently selected from oxo (=O), halogen, hydroxy, mercapto, amino, nitro, cyano, alkyl, haloalkyl, alkoxy, haloalkoxy, acyl, sulfonyl, sulfinyl, cycloalkyl, heterocyclyl, aryl or heteroaryl; and wherein $R^{14}$, $R^{15}$, $R^{16}$, $R^{17}$ and $R^{18}$ are as defined herein.

In other embodiments, each $R^{14}$, $R^{16}$, $R^{17}$ and $R^{18}$ is independently cycloalkyl, cycloalkylalkyl, heterocyclyl, heterocyclylalkyl, aryl, arylalkyl, heteroaryl or heteroarylalkyl, and wherein optionally each of the cycloalkyl, cycloalkylalkyl, heterocyclyl, heterocyclylalkyl, aryl, arylalkyl, heteroaryl and heteroarylalkyl is independently substituted with one, two, three or four substituents independently selected from oxo (=O), halogen, hydroxy, amino, nitro, cyano, alkyl, haloalkyl, alkoxy, haloalkoxy, acyl or sulfonyl; and each $R^{15}$ is independently H or alkyl, and wherein the alkyl is independently and optionally substituted with one, two, three or four substituents independently selected from oxo (=O), halogen, alkyl, haloalkyl, amino, alkoxy, haloalkoxy, cycloalkyl, heterocyclyl, aryl or hereroaryl.

In certain embodiments, $R^6$ is H, hydroxy, mercapto, amino or alkyl;

each $R^7$ is independently H or alkyl, and wherein the alkyl is independently and optionally substituted with one, two, three or four substituents independently selected from halogen, amino, hydroxy, alkoxy, cycloalkyl, heterocyclyl, aryl or hereroaryl; and each $R^8$ and $R^9$ is independently H or alkyl, and wherein the alkyl is independently and optionally substituted with one, two, three or four substituents independently selected from halogen, amino, hydroxy, alkoxy, cycloalkyl, heterocyclyl, aryl or hereroaryl.

In certain embodiments, k is 1, 2, 3 or 4.

In certain embodiments, each m is independently 1, 2, 3 or 4.

In certain embodiments, each n is independently 0, 1 or 2.

In certain embodiments, each p and q is independently 0, 1, 2, 3 or 4.

In certain embodiments, the compound disclosed herein, wherein each L is independently —(CR$^{11}$R$^{12}$)$_m$—, —(CR$^{11}$R$^{12}$)$_p$—O—, —(CR$^{11}$R$^{12}$)$_p$—S(=O)—, —(CR$^{11}$R$^{12}$)$_p$—N(R$^{13}$)—, —(CR$^{11}$R$^{12}$)$_p$—C(=X—, (CR$^{11}$R$^{12}$)$_p$—C(=X)N(R$^{13}$)—(CR$^{11}$R$^{12}$)$_q$—, —(CR$^{11}$R$^{12}$)$_p$—C(=X)O—(CR$^{11}$R$^{12}$)$_q$—, —(CR$^{11}$R$^{12}$)$_p$—OC(=X)N(R$^{13}$)—(CR$^{11}$R$^{12}$)$_q$—, —(CR$^{11}$R$^{12}$)$_p$—N(R$^{13}$)C(=X)N(R$^{13}$)—(CR$^{11}$R$^{12}$)$_q$—, —(CR$^{11}$R$^{12}$)$_p$—S(=O)$_2$N(R$^{13}$)—(CR$^{11}$R$^{12}$)$_q$—, —(CR$^{11}$R$^{12}$)$_p$—S(=O)$_2$O—(CR$^{11}$R$^{12}$)$_q$—, C$_{3-10}$ cycloalkylene, C$_{2-9}$ heterocyclylene or C$_{1-9}$ heteroarylene, and wherein optionally each of the C$_{3-10}$ cycloalkylene, C$_{2-9}$ heterocyclylene and C$_{1-9}$ heteroarylene is independently substituted with one, two, three or four substituents independently selected from oxo (=O), hydroxy, mercapto, amino, nitro, cyano, halogen, C$_{1-6}$ alkyl, C$_{1-6}$ haloalkyl, C$_{1-6}$ alkoxy, C$_{1-6}$ haloalkoxy, acyl, sulfonyl, C$_{3-10}$ cycloalkyl, C$_{2-9}$ heterocyclyl, C$_{6-10}$ aryl or C$_{1-9}$ hereroaryl;

wherein each X is independently O or S; and R$^{11}$, R$^{12}$, R$^{13}$, m, n, p and q are as defined herein.

In other embodiments, each R$^{11}$ and R$^{12}$ is independently H, halogen, cyano, hydroxy, mercapto, amino, C$_{1-6}$ alkyl, C$_{1-6}$ haloalkyl, C$_{1-6}$ alkoxy, C$_{1-6}$ haloalkoxy, C$_{3-10}$ cycloalkyl, C$_{2-9}$ heterocyclyl, C$_{6-10}$ aryl or C$_{1-9}$ heteroaryl, and wherein optionally each of the hydroxy, mercapto, amino, C$_{1-6}$ alkyl, C$_{1-6}$ haloalkyl, C$_{1-6}$ alkoxy, C$_{1-6}$ haloalkoxy, C$_{3-10}$ cycloalkyl, C$_{2-9}$ heterocyclyl, C$_{6-10}$ aryl and C$_{1-9}$ heteroaryl is independently substituted with one, two, three or four substituents independently selected from oxo (=O), halogen, hydroxy, amino, C$_{1-6}$ alkyl, C$_{1-6}$ haloalkyl, C$_{1-6}$ alkoxy, C$_{1-6}$ haloalkoxy, acyl, sulfonyl, C$_{3-8}$ cycloalkyl, C$_{2-7}$ heterocyclyl, C$_{6-10}$ aryl or C$_{1-9}$ heteroaryl.

In other embodiments, each R$^{13}$ is independently H, C$_{1-6}$ alkyl, C$_{3-10}$ cycloalkyl, C$_{2-9}$ heterocyclyl, C$_{6-10}$ aryl or C$_{1-9}$ heteroaryl, and wherein optionally each of the C$_{1-6}$ alkyl, C$_{3-10}$ cycloalkyl, C$_{2-9}$ heterocyclyl, C$_{6-10}$ aryl and C$_{1-9}$ heteroaryl is independently substituted with one, two, three or four substituents independently selected from oxo (=O), cyano, nitro, halogen, hydroxy, amino, mercapto, C$_{1-6}$ alkyl, C$_{1-6}$ haloalkyl, C$_{1-6}$ alkoxy, C$_{1-6}$ haloalkoxy, acyl, sulfonyl, C$_{3-8}$ cycloalkyl, C$_{2-7}$ heterocyclyl, C$_{6-10}$ aryl and C$_{1-9}$ heteroaryl.

In certain embodiments, each L is independently —(CR$^{11}$R$^{12}$)$_m$—, —(CR$^{11}$R$^{12}$)$_p$—O—, —(CR$^{11}$R$^{12}$)$_p$—S(O)—, —(CR$^{11}$R$^{12}$)$_p$—N(R$^{13}$)—, —(CR$^{11}$R$^{12}$)$_p$—C(O)N(R$^{13}$)—(CR$^{11}$R$^{12}$)$_q$—, C$_{3-8}$ cycloalkylene, C$_{2-7}$ heterocyclylene or C$_{1-5}$ heteroarylene, and wherein optionally each of the C$_{3-8}$ cycloalkylene, C$_{2-7}$ heterocyclylene and C$_{1-5}$ heteroarylene is independently substituted with one, two, three or four substituents independently selected from oxo (=O), hydroxy, mercapto, —NH$_2$, methylamino, dimethylamino, nitro, cyano, fluorine, chlorine, bromine, methyl, ethyl, propyl, n-butyl, t-butyl, trifluoromethyl, methoxy, ethoxy, trifluoromethoxy, acetyl, methoxycarbonyl, carbamoyl, methyl sulfonyl, aminosulfonyl, methoxysulfonyl, cyclopropyl, cyclohexyl, piperidyl, morpholinyl, phenyl, naphthyl, pyrrolyl, thienyl or pyridyl; and wherein R$^{11}$, R$^{12}$, R$^{13}$, m, n, p and q are as defined herein.

In other embodiments, each R$^{11}$ and R$^{12}$ is independently H, fluorine, chlorine, bromine, C$_{1-4}$ alkyl, C$_{1-4}$ haloalkyl, C$_{3-6}$ cycloalkyl, C$_{2-5}$ heterocyclyl, C$_{6-10}$ aryl or C$_{1-5}$ heteroaryl, and wherein optionally each of the C$_{1-4}$ alkyl, C$_{1-4}$ haloalkyl, C$_{3-6}$ cycloalkyl, C$_{2-5}$ heterocyclyl, C$_{6-10}$ aryl and C$_{1-5}$ heteroaryl is independently substituted with one, two, three or four substituents independently selected from oxo (=O), fluorine, chlorine, bromine, hydroxy, —NH$_2$, methylamino, dimethylamino, methyl, ethyl, propyl, n-butyl, t-butyl, trifluoromethyl, methoxy, trifluoromethoxy, cyclopropyl, cyclopentyl, cyclohexyl, pyrrolidyl, piperidyl, morpholinyl, phenyl, naphthyl, pyrrolyl, thienyl or pyridyl.

In other embodiments, each R$^{13}$ is independently H, C$_{1-4}$ alkyl, C$_{3-6}$ cycloalkyl, C$_{2-5}$ heterocyclyl, C$_{6-10}$ aryl or C$_{1-5}$ heteroaryl, and wherein optionally each of the C$_{1-4}$ alkyl, C$_{3-6}$ cycloalkyl, C$_{2-5}$ heterocyclyl, C$_{6-10}$ aryl and C$_{1-5}$ heteroaryl is independently substituted with one, two, three or four substituents independently selected from oxo (=O), cyano, nitro, fluorine, chlorine, bromine, hydroxy, —NH$_2$, methylamino, dimethylamino, methyl, ethyl, propyl, n-butyl, t-butyl, trifluoromethyl, methoxy, trifluoromethoxy, acetyl, methyl sulfonyl, cyclopropyl, cyclopentyl, cyclohexyl, pyrrolidyl, piperidyl, morpholinyl, phenyl or pyridyl.

In certain embodiments, the compound disclosed herein, wherein each L is independently —(CR$^{11}$R$^{12}$)$_m$—, —O—, —S(=O)—, —N(R$^{13}$)—, —(CR$^{11}$R$^{12}$)$_p$—C(=O)N(R$^{13}$)—(CR$^{11}$R$^{12}$)$_q$—, C$_{3-6}$ cycloalkylene, C$_{2-5}$ heterocyclylene or C$_{1-5}$ heteroarylene, and wherein optionally each of the C$_{3-6}$ cycloalkylene, C$_{2-5}$ heterocyclylene and C$_{1-5}$ heteroarylene is independently substituted with one, two, three or four substituents independently selected from oxo (=O), hydroxy, mercapto, —NH$_2$, methylamino, dimethylamino, nitro, cyano, fluorine, chlorine, bromine, methyl, ethyl, propyl, n-butyl, t-butyl, trifluoromethyl, methoxy, ethoxy, trifluoromethoxy, acetyl, carbamoyl, methyl sulfonyl, aminosulfonyl or methoxysulfonyl; and wherein R$^{11}$, R$^{12}$, R$^{13}$, m, n, p and q are as defined herein.

In certain embodiments, each R$^{10}$ is independently —OR$^{14}$, —NR$^{15}$R$^{16}$, —C(=O)NR$^{15}$R$^{16}$, —N(R$^{15}$)C(=O)R$^{17}$, —C(=O)R$^{17}$, —S(=O)$_n$R$^{18}$, —S(=O)$_2$NR$^{15}$R$^{16}$, —N(R$^{15}$)S(O)$_2$R$^{18}$, C$_{3-10}$ cycloalkyl, C$_{3-10}$ cycloalkyl-C$_{1-6}$-alkyl, C$_{2-9}$ heterocyclyl, C$_{2-9}$ heterocyclyl-C$_{1-6}$-alkyl, C$_{6-10}$ aryl, C$_{6-10}$ aryl-C$_{1-6}$-alkyl, C$_{1-9}$ heteroaryl or C$_{1-9}$ heteroaryl-C$_{1-6}$-alkyl, and wherein optionally each of the C$_{3-10}$ cycloalkyl, C$_{3-10}$ cycloalkyl-C$_{1-6}$-alkyl, C$_{2-9}$ heterocyclyl, C$_{2-9}$ heterocyclyl-C$_{1-6}$-alkyl, C$_{6-10}$ aryl, C$_{6-10}$ aryl-C$_{1-6}$-alkyl, C$_{1-9}$ heteroaryl and C$_{1-9}$ heteroaryl-C$_{1-6}$-alkyl is independently substituted with one, two, three or four substituents independently selected from oxo (=O), halogen, hydroxy, mercapto, amino, nitro, cyano, C$_{1-6}$ alkyl, C$_{1-6}$ haloalkyl, C$_{1-6}$ alkoxy, C$_{1-6}$ haloalkoxy, acyl, sulfonyl, C$_{3-10}$ cycloalkyl, C$_{2-9}$ heterocyclyl, C$_{6-10}$ aryl or C$_{1-9}$ heteroaryl; and wherein R$^{14}$, R$^{15}$, R$^{16}$, R$^{17}$ and R$^{18}$ are as defined herein.

In certain embodiments, each R$^{14}$, R$^{16}$, R$^{17}$ and R$^{18}$ is independently C$_{3-10}$ cycloalkyl, C$_{3-10}$ cycloalkyl-C$_{1-6}$-alkyl, C$_{2-9}$ heterocyclyl, C$_{2-9}$ heterocyclyl-C$_{1-6}$-alkyl, C$_{6-10}$ aryl, C$_{6-10}$ aryl-C$_{1-6}$-alkyl, C$_{1-9}$ heteroaryl or C$_{1-9}$ heteroaryl-C$_{1-6}$-alkyl, and wherein optionally each of the C$_{3-10}$ cycloalkyl, C$_{3-10}$ cycloalkyl-C$_{1-6}$-alkyl, C$_{2-9}$ heterocyclyl, C$_{2-9}$ heterocyclyl-C$_{1-6}$-alkyl, C$_{6-10}$ aryl, C$_{6-10}$ aryl-C$_{1-6}$-alkyl, C$_{1-9}$ heteroaryl and C heteroaryl-C$_{1-6}$-alkyl is independently substituted with one, two, three or four substituents independently selected from oxo (=O), halogen, hydroxy, amino, nitro, cyano, C$_{1-4}$ alkyl, C$_{1-4}$ haloalkyl, C$_{1-4}$ alkoxy, C$_{1-4}$ haloalkoxy, acyl and sulfonyl;

each R$^{15}$ is independently H or C$_{1-6}$ alkyl, and wherein C$_{1-6}$ alkyl is independently and optionally substituted with one, two, three or four substituents independently selected from oxo (=O), halogen, C$_{1-4}$ alkyl, C$_{1-4}$ haloalkyl, amino, C$_{1-4}$ alkoxy, C$_{1-4}$ haloalkyl, C$_{3-6}$ cycloalkyl, C$_{2-5}$ heterocyclyl, C$_{6-10}$ aryl or C$_{1-5}$ heteroaryl.

In certain embodiments, each R$^{10}$ is independently C$_{3-8}$ cycloalkyl, C$_{3-8}$ cycloalkyl-C$_{1-4}$-alkyl, C$_{2-7}$ heterocyclyl, C$_{2-7}$ heterocyclyl-C$_{1-4}$-alkyl, C$_{6-10}$ aryl, C$_{6-10}$ aryl-C$_{1-4}$-alkyl, C$_{1-9}$ heteroaryl or C$_{1-9}$ heteroaryl-C$_{1-4}$-alkyl, and wherein optionally each of the $C_{3-8}$ cycloalkyl, $C_{3-8}$ cycloalkyl-$C_{1-4}$-alkyl, $C_{2-7}$ heterocyclyl, $C_{2-7}$ heterocyclyl-$C_{1-4}$-alkyl, $C_{6-10}$ aryl, $C_{6-10}$ aryl-$C_{1-4}$-alkyl, $C_{1-9}$ heteroaryl and C heteroaryl-$C_{1-4}$-alkyl is independently substituted with one, two, three or four substituents independently selected from oxo (=O), fluorine, chlorine, bromine, hydroxy, —$NH_2$, methylamino, dimethylamino, nitro, cyano, $C_{1-4}$ alkyl, $C_{1-4}$ haloalkyl, $C_{1-4}$ alkoxy, $C_{1-4}$ haloalkoxy, acyl, sulfonyl, $C_{3-6}$ cycloalkyl, $C_{2-5}$ heterocyclyl, $C_{6-10}$ aryl or $C_{1-9}$ heteroaryl.

In certain embodiments, the compound disclosed herein, wherein each $R^{10}$ is independently $C_{3-6}$ cycloalkyl, $C_{3-6}$ cycloalkyl-$C_{1-3}$-alkyl, $C_{2-5}$ heterocyclyl, $C_{2-5}$ heterocyclyl-$C_{1-3}$-alkyl, $C_{6-10}$ aryl, $C_{6-10}$ aryl-$C_{1-3}$-alkyl, $C_{1-9}$ heteroaryl or $C_{1-9}$ heteroaryl-$C_{1-3}$-alkyl, and wherein optionally each of the $C_{3-6}$ cycloalkyl, $C_{3-6}$ cycloalkyl-$C_{1-3}$-alkyl, $C_{2-5}$ heterocyclyl, $C_{2-5}$ heterocyclyl-$C_{1-3}$-alkyl, $C_{6-10}$ aryl, $C_{6-10}$ aryl-$C_{1-3}$-alkyl, $C_{1-9}$ heteroaryl and $C_{1-9}$ heteroaryl-$C_{1-3}$-alkyl is independently substituted with one, two, three or four substituents independently selected from oxo (=O), fluorine, chlorine, bromine, hydroxy, —$NH_2$, methylamino, dimethylamino, nitro, cyano, methyl, ethyl, propyl, n-butyl, t-butyl, trifluoromethyl, methoxy, ethoxy, trifluoromethoxy, acetyl, methoxycarbonyl, carbamoyl, methyl sulfonyl, aminosulfonyl, methoxysulfonyl, cyclopropyl, cyclohexyl, pyrrolidyl, piperidyl, morpholinyl, oxomorpholinyl, phenyl, naphthyl, pyrrolyl, thienyl, pyridyl, pyrimidinyl or quinolinyl.

In other embodiments, the compound disclosed herein, wherein $R^1$ is H, $C_{1-4}$ alkyl, $C_{3-8}$ cycloalkyl, $C_{2-5}$ heterocyclyl, $C_{6-10}$ aryl or $C_{1-9}$ heteroaryl; and wherein $C_{1-4}$ alkyl described in $R^1$ is optionally substituted with one, two, three or four substituents independently selected from oxo (=O), halogen, amino, hydroxy, mercapto, cyano, $C_{1-4}$ alkyl, $C_{2-4}$ alkenyl, $C_{1-4}$ haloalkyl, $C_{1-4}$ alkoxy, acyl, sulfonyl, $C_{3-6}$ cycloalkyl, $C_{2-5}$ heterocyclyl or $C_{1-5}$ hereroaryl; wherein optionally each of the $C_{3-8}$ cycloalkyl, $C_{2-5}$ heterocyclyl, $C_{6-10}$ aryl and $C_{1-9}$ heteroaryl described in $R^1$ is independently substituted with one, two, three or four substituents independently selected from oxo (=O), nitro, cyano, halogen, $C_{1-6}$ alkyl, $C_{2-6}$ alkenyl, $C_{1-6}$ haloalkyl, amino, hydroxy, mercapto, $C_{1-6}$ alkoxy, acyl, sulfonyl, $C_{3-8}$ cycloalkyl, $C_{2-7}$ heterocyclyl, $C_{6-10}$ aryl or $C_{1-9}$ heteroaryl.

In certain embodiments, $R^1$ is H, methyl, ethyl, propyl or butyl, and wherein optionally each of the methyl, ethyl, propyl and butyl is independently substituted with one, two, three or four substituents independently selected from fluorine, chlorine, bromine, —$NH_2$, hydroxy, methyl, ethyl, benzoyl, phenylsulfonyl, cyclopropyl, cyclobutyl, cyclopentyl, cyclohexyl, oxiranyl, azetidinyl, tetrahydrofuranyl, pyrrolidinyl, piperidyl, piperazinyl, morpholinyl, oxomorpholinyl, pyrrolyl, furyl, thienyl, pyridyl or pyrimidinyl.

In certain embodiments, wherein, $R^6$ is H or hydroxy;

$R^7$ is H, methyl, ethyl, propyl or butyl; and each $R^8$ and $R^9$ is independently H, methyl, ethyl, propyl or butyl.

In certain embodiments, provided herein is a compound having Formula (II) or a stereoisomer, a geometric isomer, a tautomer, an N-oxide, a hydrate, a solvate, a metabolite, a ester, a pharmaceutically acceptable salt or a prodrug thereof,

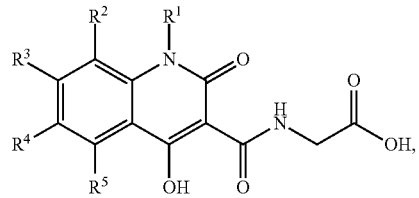

(II)

wherein $R^1$, $R^2$, $R^3$, $R^4$ and $R^5$ are as defined herein.

In certain embodiments, each L is independently —($CR^{11}R^{12}$)—, —($CR^{11}R^{12}$)$_2$—, —O—, —S(=O)$_2$—, —C(=O)N($R^{13}$)—, —($CR^{11}R^{12}$)—C(=O)N($R^{13}$)—, —C(=O)N($R^{13}$)—($CR^{11}R^{12}$)—, —($CR^{11}R^{12}$)—C(=O)N ($R^{13}$)—($CR^{11}R^{12}$)—, cyclopentylene, cyclohexylene, pyrrolidylene, pyrazolidylene, oxazolidinylene, piperidylene, tetrahydropyrimidinylene, oxotetrahydropyrimidylene, piperazinylene, oxazinanylene, thiazolylene, pyrrolylene, thienylene, furylene, pyrazolylene, imidazolylene, pyridinylene, pyrimidinylene or pyrazinylene, and wherein optionally each of the cyclopentylene, cyclohexylene, pyrrolidylene, pyrazolidylene, oxazolidinylene, piperidylene, tetrahydropyrimidinylene, oxotetrahydropyrimidylene, piperazinylene, oxazinanylene, thiazolylene, pyrrolylene, thienylene, furylene, pyrazolylene, imidazolylene, pyridinylene, pyrimidinylene and pyrazinylene is independently substituted with one, two, three or four substituents independently selected from oxo (=O), hydroxy, —$NH_2$, methylamino, dimethylamino, nitro, cyano, fluorine, chlorine, bromine, methyl, ethyl, propyl, n-butyl, t-butyl, trifluoromethyl, methoxy, ethoxy, trifluoromethoxy, acetyl, carbamoyl, methyl sulfonyl, aminosulfonyl or methoxysulfonyl; and wherein $R^{11}$, $R^{12}$ and $R^{13}$ are as defined herein.

In other embodiments, each $R^{11}$ and $R^{12}$ is independently H, methyl, ethyl, propyl, butyl, cyclopropyl, cyclopentyl, cyclohexyl, pyrrolidyl, piperidyl, morpholinyl, phenyl or pyridyl, and wherein optionally each of the methyl, ethyl, propyl, butyl, cyclopropyl, cyclopentyl, cyclohexyl, pyrrolidyl, piperidyl, morpholinyl, phenyl and pyridyl is independently substituted with one, two, three or four substituents independently selected from fluorine, chlorine, bromine, hydroxy, —$NH_2$, methylamino, dimethylamino, methyl, ethyl, trifluoromethyl, methoxy or trifluoromethoxy.

In other embodiments, each $R^{13}$ is independently H, methyl, ethyl, propyl or butyl, and wherein optionally each of the methyl, ethyl, propyl and butyl is independently substituted with one, two, three or four substituents independently selected from fluorine, chlorine, bromine, hydroxy, —$NH_2$, methylamino, dimethylamino, methyl, ethyl, trifluoromethyl, methoxy, trifluoromethoxy, acetyl or methyl sulfonyl.

In certain embodiments, the compound disclosed herein, wherein each $R^{10}$ is independently cyclopropyl, cyclopentyl, cyclohexyl, cyclopropylmethyl, cyclopropylethyl, cyclopentylmethyl, cyclohexylmethyl, cyclohexylethyl, cyclohexylpropyl, oxiranyl, pyrrolidyl, pyrazolidyl, oxazolidinyl, piperidyl, morpholinyl, tetrahydropyrimidinyl, piperazinyl, oxazinanyl, pyrrolidinylmethyl, piperdinylmethyl, phenyl, 2,3-dihydro-1H-indenyl, naphthyl, benzyl, naphthylmethyl, phenylethyl, pyrrolyl, pyrazolyl, furyl, imidazolyl, oxazolyl, thienyl, thiazolyl, pyridinyl, pyrimidinyl, indolyl, dihydroindolyl, quinolyl, isoquinolyl, quinazolinyl, imidazopyridinyl, benzimidazolyl, benzofuranyl, benzothienyl, pyridinylmethyl or quinolylmethyl, and wherein optionally each of the cyclopropyl, cyclopentyl, cyclohexyl, cyclopropylmethyl, cyclopropyl ethyl, cyclopentyl m ethyl, cyclohexylmethyl, cyclohexyl ethyl, cyclohexylpropyl, oxiranyl, pyrrolidyl, pyrazolidyl, oxazolidinyl, piperidyl, morpholinyl, tetrahydropyrimidinyl, piperazinyl, oxazinanyl, pyrrolidinylmethyl, piperdinylmethyl, phenyl, 2,3-dihydro-1H-indenyl, naphthyl, benzyl, naphthylmethyl, phenylethyl, pyrrolyl, pyrazolyl, furyl, imidazolyl, oxazolyl, thienyl, thiazolyl, pyridinyl, pyrimidinyl, indolyl, dihydroindolyl, quinolyl, isoquinolyl, quinazolinyl, imidazopyridinyl, benzimidazolyl, benzofuranyl, benzothienyl, pyridinylmethyl and quinolylmethyl is independently substituted with one, two, three or four substituents independently selected from oxo (=O), fluorine, chlorine, bromine, hydroxy, —NH$_2$, methylamino, dimethylamino, nitro, cyano, methyl, ethyl, propyl, n-butyl, t-butyl, trifluoromethyl, methoxy, ethoxy, trifluoromethoxy, acetyl, methoxycarbonyl, carbamoyl, methyl sulfonyl, aminosulfonyl, methoxysulfonyl, cyclopropyl, cyclohexyl, pyrrolidyl, piperidyl, morpholinyl, oxomorpholinyl, phenyl, pyrrolyl, thienyl or pyridyl.

In certain embodiments, provided herein is a compound having one of the following structures, (1)

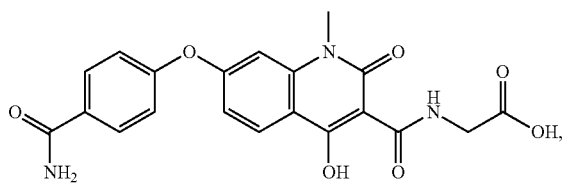

(2)

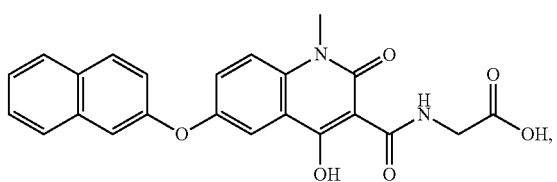

(3)

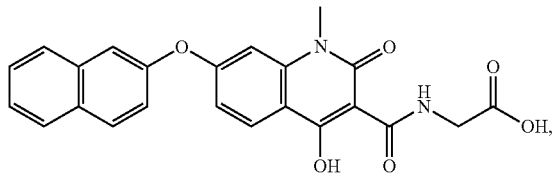

(4)

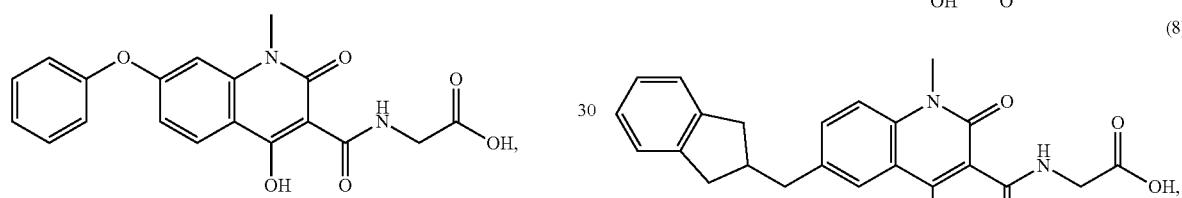

(5)

(6)

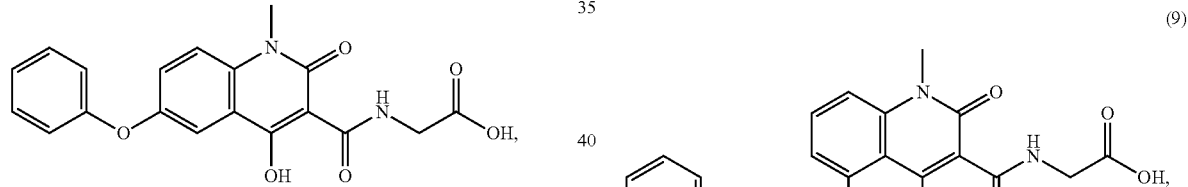

(7)

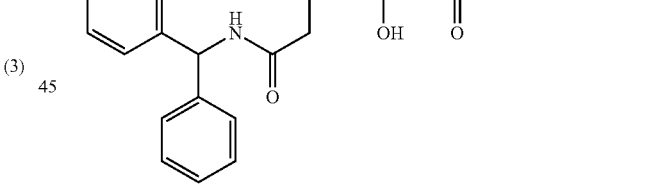

(8)

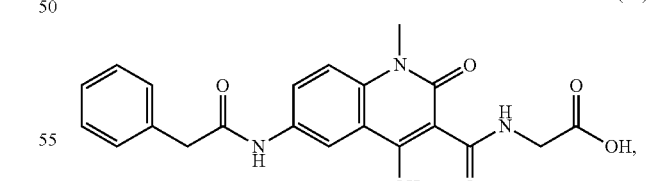

(9)

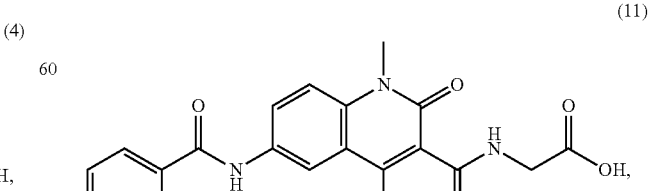

(10)

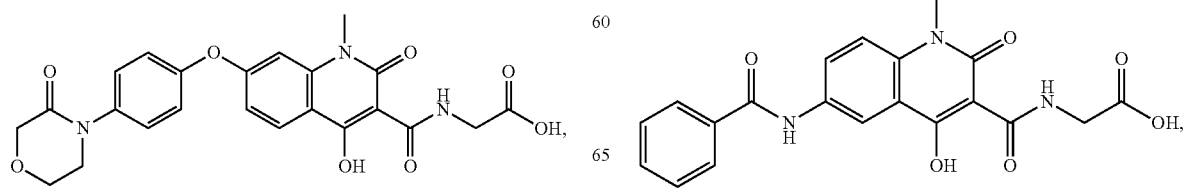

(11)

(12) 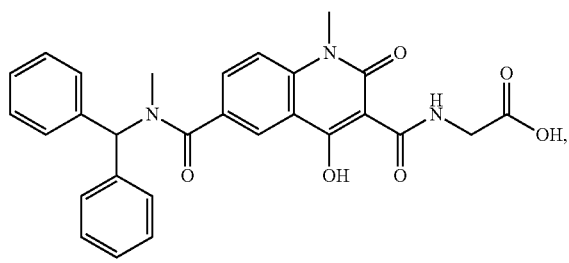
(13) 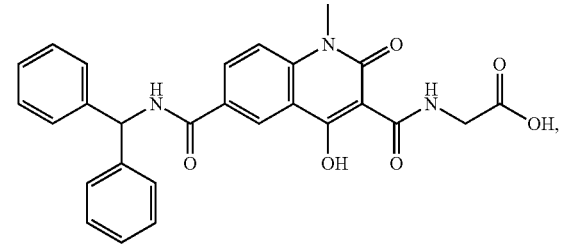
(14) 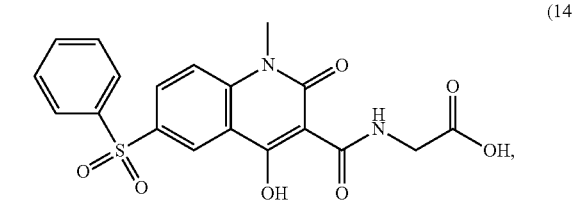
(15) 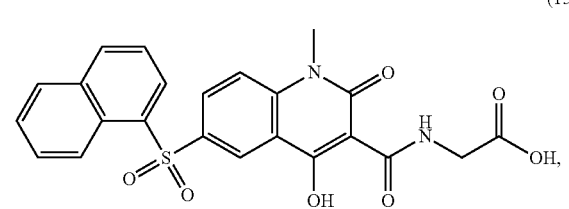
(16) 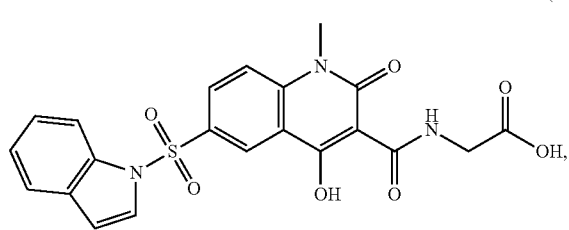
(17) 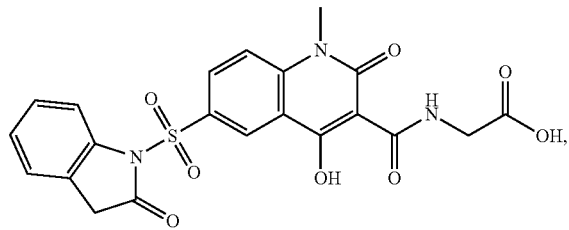
(18) 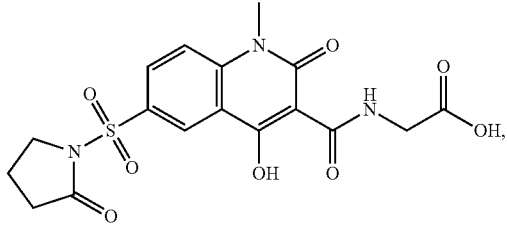
(19) 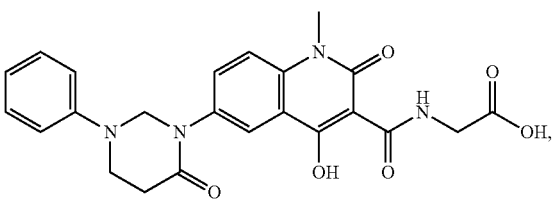
(20) 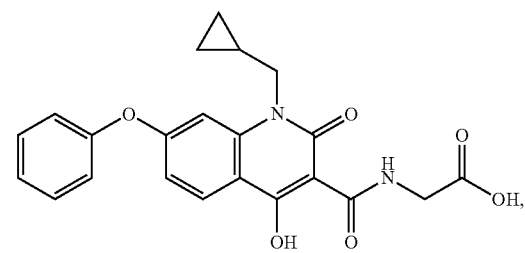
(21) 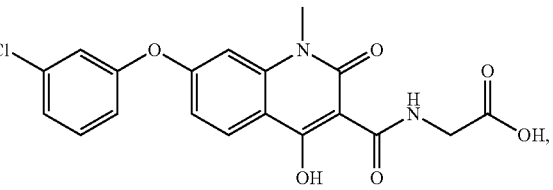
(22) 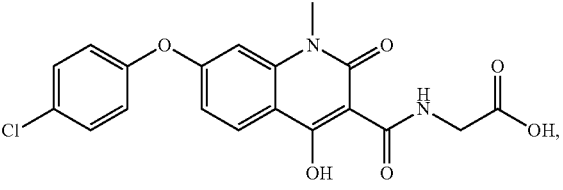
(23) 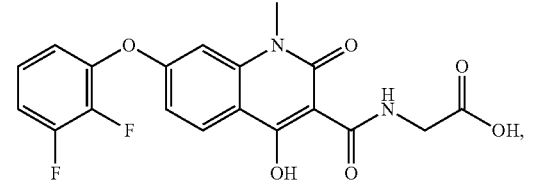
(24) 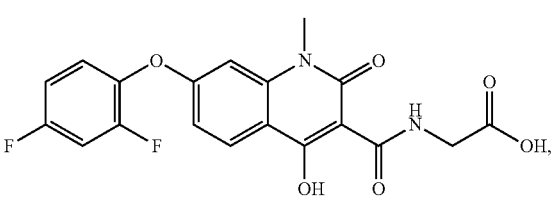

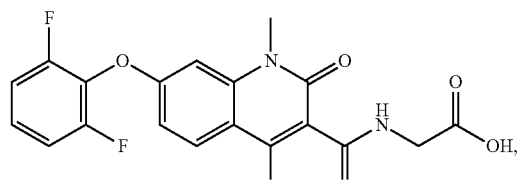
(25)
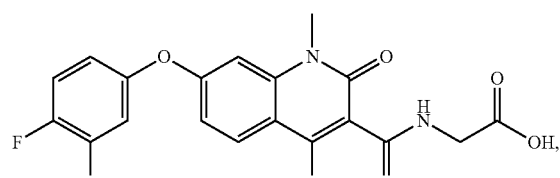
(26)
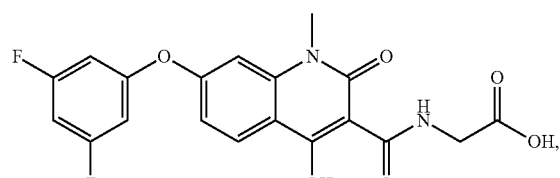
(27)
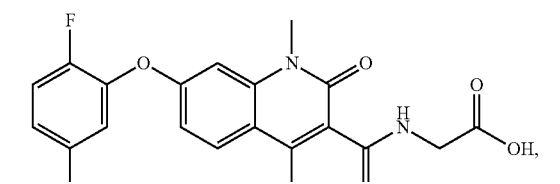
(28)
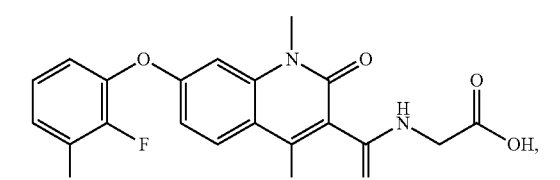
(29)
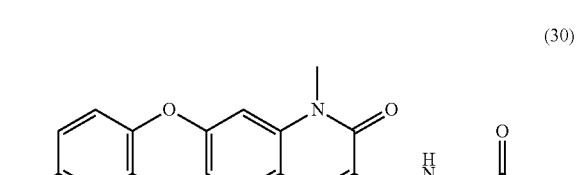
(30)
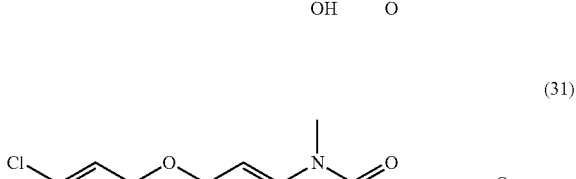
(31)
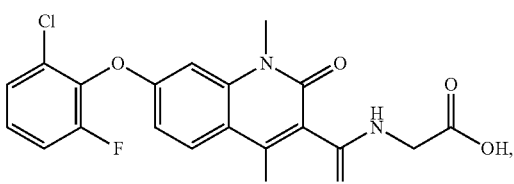
(32)
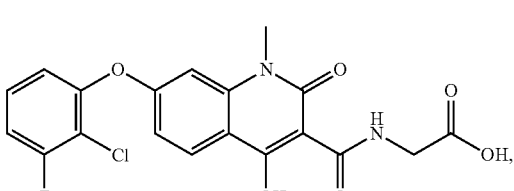
(33)
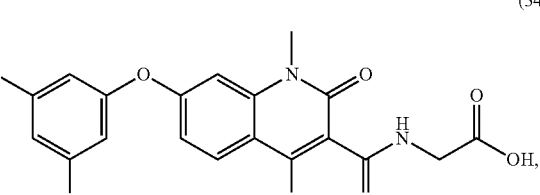
(34)
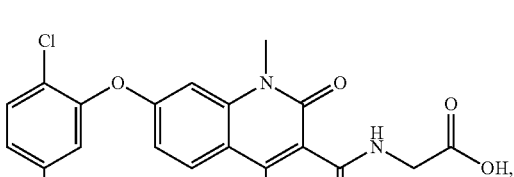
(35)
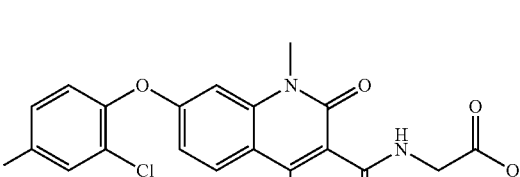
(36)
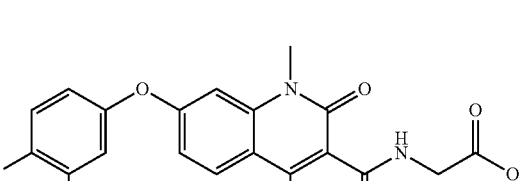
(37)
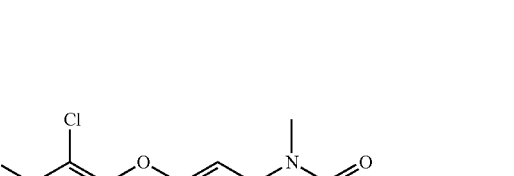
(38)

(39) 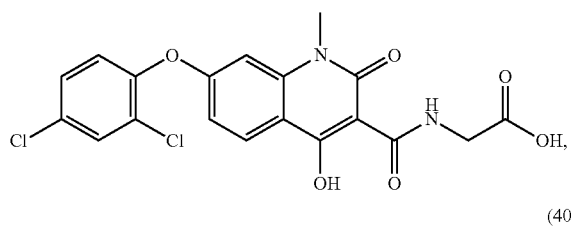
(40) 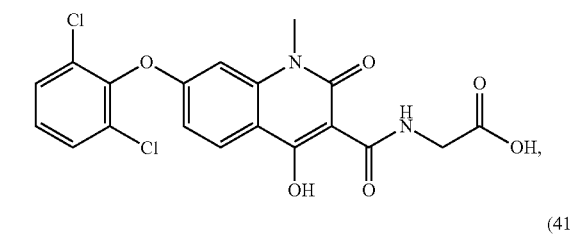
(41) 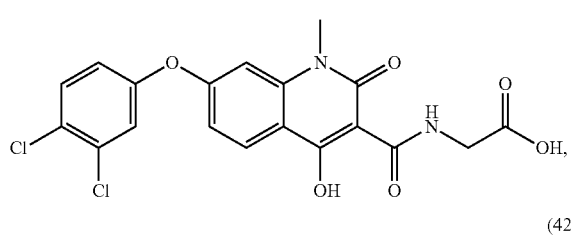
(42) 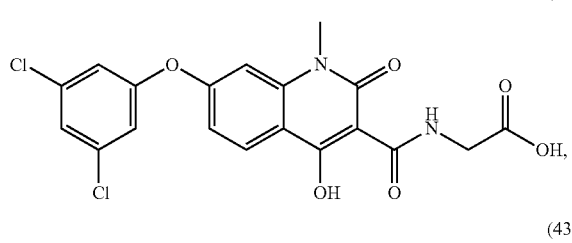
(43) 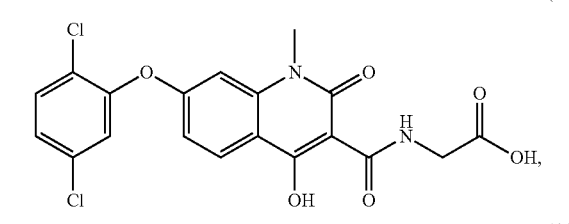
(44) 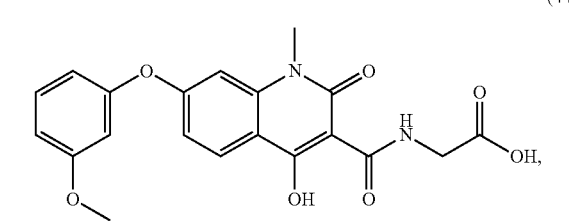
(45) 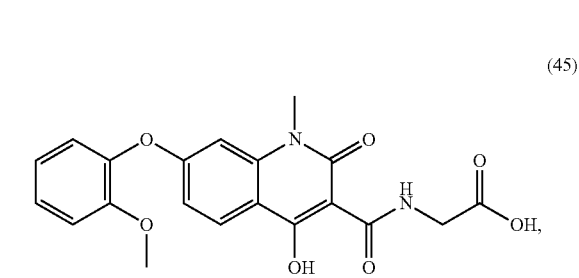
(46) 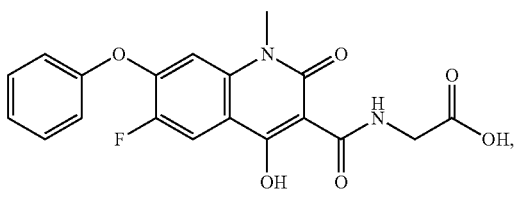
(47) 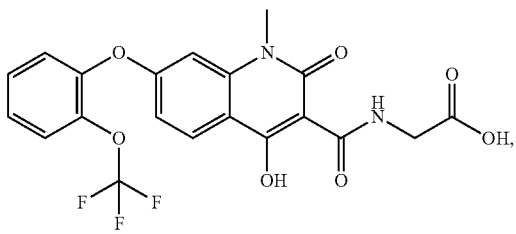
(48) 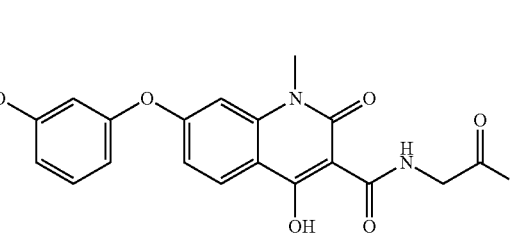
(49) 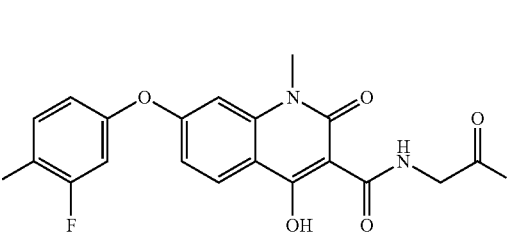
(50) 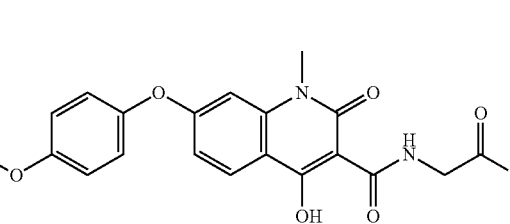
(51) 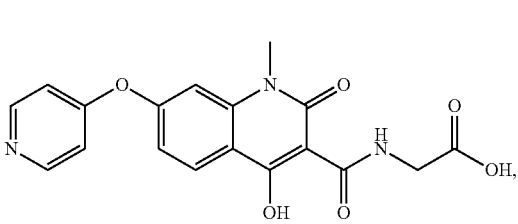
(52) 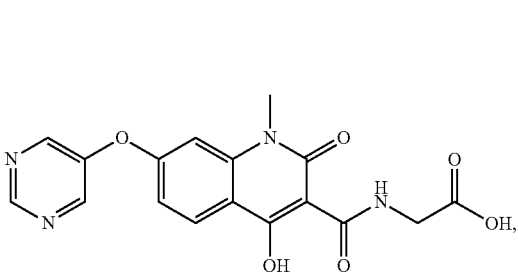

(53)

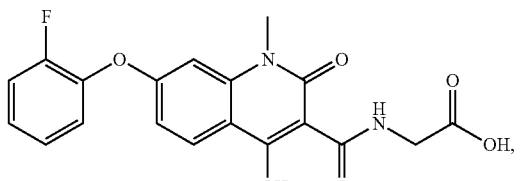

(54)

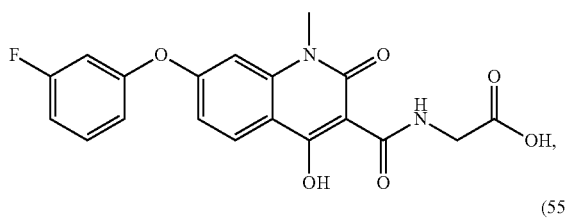

(55)

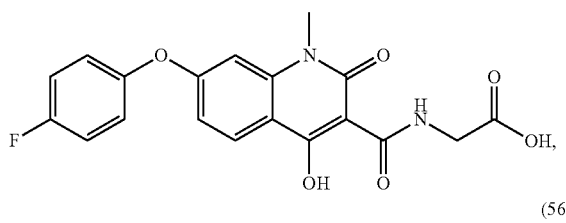

(56)

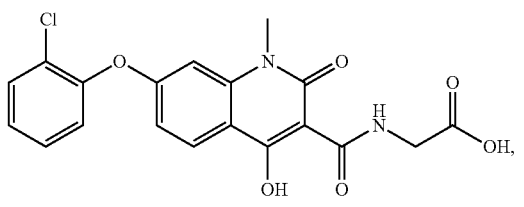

or a stereoisomer, a geometric isomer, a tautomer, an N-oxide, a hydrate, a solvate, a metabolite, an ester, a pharmaceutically acceptable salt or a prodrug thereof.

In other aspect, provided herein is a pharmaceutical composition comprising the compound disclosed herein.

In certain embodiments, the pharmaceutical composition disclosed herein further comprises at least one of pharmaceutically acceptable carriers, excipients, diluents, adjuvants and vehicles.

In one aspect, provided herein is use of the compound or the pharmaceutical composition disclosed herein in the manufacture a medicament, and wherein the medicament is used for preventing, managing, treating or lessening a disease in a patient wherein the disease is related to hypoxia inducible factor (HIF) and/or erythropoietin (EPO).

In certain embodiments, the use disclosed herein, wherein the medicament is used for preventing, managing, treating or lessening disease in a patient wherein the disease is mediated at least in part by HIF prolyl hydroxylase.

In certain embodiments, the use disclosed herein, wherein the disease is anemia, ischemia, a vascular disease, angina pectoris, myocardial ischemia, myocardial infarction, a metabolic disorder or wound healing.

In other embodiments, the use disclosed herein, wherein the disease is anemia; and wherein the anemia comprises acute or chronic kidney disease, infection, inflammation, cancer, radiation, toxins, diabetes or surgically induced anemia.

In another aspect, provided herein is the compound or the pharmaceutical composition disclosed herein for use in preventing, managing, treating or lessening a disease in a patient wherein the disease is related to hypoxia inducible factor and/or erythropoietin.

In certain embodiments, the compound or the composition disclosed herein is for use in preventing, managing, treating or lessening a disease in a patient wherein the disease is mediated at least in part by hypoxia inducible factor prolyl hydroxylase in a patient.

In other embodiments, the compound or pharmaceutical compositions disclosed herein, wherein the disease is anemia, ischemia, a vascular disease, angina pectoris, myocardial ischemia, myocardial infarction, a metabolic disorder or wound healing.

In other embodiments, the compound or pharmaceutical compositions disclosed herein, wherein the disease is anemia; and wherein the anemia comprises an acute or chronic kidney disease, infection, inflammation, cancer, radiation, toxins, diabetes or surgically induced anemia.

In another aspect, provided herein is a method for preventing, managing, treating or lessening a disease in a patient wherein the disease is related to hypoxia inducible factor and/or erythropoietin comprising administering to the patient a therapeutically effective amount of the compound or the pharmaceutical composition disclosed herein.

In certain embodiments, the method disclosed herein is a method for preventing, managing, treating or lessening a disease in a patient wherein the disease is mediated at least in part by hypoxia inducible factor (HIF) prolyl hydroxylase.

In other embodiments, the method disclosed herein, wherein the disease is anemia, ischemia, a vascular disease, angina pectoris, myocardial ischemia, myocardial infarction, a metabolic disorder or wound healing.

In other embodiments, the method disclosed herein, wherein the disease is anemia; and wherein the anemia comprises an acute or chronic kidney disease, infection, inflammation, cancer, radiation, toxins, diabetes or surgically induced anemia.

The present invention also comprises uses of the compound and pharmaceutically acceptable salts thereof in the manufacture of a medicament for treating a disease in a patient wherein the disease is related to hypoxia-inducible factor (HIF) and/or erythropoietin (EPO), including those described in the invention. Also provided herein is a pharmaceutical composition comprising a therapeutically effective amount of a compound of Formula (I) or Formula (II) in association with at least one pharmaceutically acceptable carriers, excipients, diluents, adjuvants and vehicles.

The present invention also provides a method of treating or lessening a disease in a patient wherein the disease is related to HIF and/or EPO, or a method which is sensitive to these diseases, comprising administering to the patient a therapeutically effective amount of the compound of Formula (I) or (II).

Unless otherwise stated, all hydrates, solvates and pharmaceutically acceptable salts of the compounds disclosed herein are within the scope of the invention.

In certain embodiments, the salt is a pharmaceutically acceptable salt. The phrase "pharmaceutically acceptable" refers to that the substance or composition must be compatible chemically and/or toxicologically, with the other ingredients comprising a formulation, and/or the mammal being treated therewith.

The compounds disclosed herein also include salts of the compounds which are not necessarily pharmaceutically acceptable salts, and which may be useful as intermediates for preparing and/or purifying compounds of Formula (I) or (II), and/or for separating enantiomers of compounds of Formula (I) or (II).

The salt of the compound of the invention may be prepared by any suitable method available in the art, for example, treatment of the free base with an inorganic acid, such as hydrochloric acid, hydrobromic acid, sulfuric acid, nitric acid, phosphoric acid, and the like, or with an organic acid, such as acetic acid, maleic acid, succinic acid, mandelic acid, fumaric acid, malonic acid, pyruvic acid, oxalic acid, glycolic acid and salicylic acid; a pyranosidyl acid, such as glucuronic acid and galacturonic acid; an alpha-hydroxy acid, such as citric acid and tartaric acid; an amino acid, such as aspartic acid and glutamic acid; an aromatic acid, such as benzoic acid and cinnamic acid; a sulfonic acid, such as p-toluenesulfonic acid, ethanesulfonic acid, and the like.

The activity of the compound of the invention can be assessed by using any conventionally known method. Appropriate assay methods are well known in the art. For example, the activity of inducing EPO production, HIF prolyl hydroxylase inhibitory activity, pharmacokinetic activity and/or liver microsomal stability of the compound of the present invention can be detected by an appropriate conventional method. The detection method of the invention is merely as an embodiment but does not restrict the invention. The compound of the invention has activity in at least one of the assays provided herein.

The compound of the invention having good activity of inducing erythropoietin (EPO) production in vivo or vitro can effectively induce the production of hemopoietin; meanwhile, the compound of the invention has good in vivo pharmacokinetic activities, such as good absorption, high exposure level and high bioavailability. The compound of the invention also has good liver microsomal stability and HIF Prolyl hydroxylase inhibitory activity.

Pharmaceutical Composition of the Compound of the Invention, Preparation, Administration and Use According to other aspect, the pharmaceutical composition disclosed herein is characterized by comprising the quinolinone compound having Formula (I) or (II), the compound listed in the invention, or any compound of examples 1-52, and a pharmaceutically acceptable carrier, excipient, or adjuvant. The amount of the compound in the composition disclosed herein can effectively treat or lessen a disease in a patient wherein the disease is related to HIF and/or EPO.

As described above, the pharmaceutically acceptable compositions disclosed herein further comprise a pharmaceutically acceptable carrier, an adjuvant, or a vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. As the following described: Troy et al., *Remington: The Science and Practice of Pharmacy*, 21st ed., 2005, Lippincott Williams & Wilkins, Philadelphia, and Swarbrick et al., *Encyclopedia of Pharmaceutical Technology*, eds. 1988-1999, Marcel Dekker, New York, both of which are herein incorporated by reference in their entireties, and discloses various carriers used in formulating pharmaceutically acceptable compositions and known techniques for the preparation thereof. Except insofar as any conventional carrier medium incompatible with the compounds disclosed herein, such as by producing any undesirable biological effect or otherwise interacting in a deleterious manner with any other components of the pharmaceutically acceptable composition, its use is contemplated to be within the scope of this invention.

Some non-limiting examples of materials which can serve as pharmaceutically acceptable carriers include ion exchangers; aluminium; aluminum stearate; lecithin; serum proteins such as human serum albumin; buffer substances such as phosphates; glycine; sorbic acid; potassium sorbate; partial glyceride mixtures of saturated vegetable fatty acids; water; salts or electrolytes such as protamine sulfate, disodium hydrogen phosphate, potassium hydrogen phosphate, sodium chloride and zinc salts; colloidal silica; magnesium trisilicate; polyvinyl pyrrolidone; polyacrylates; waxes; polyethylene-polyoxypropylene-block polymers; wool fat; sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol and polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants.

The compositions of the present invention can be delivered directly or in pharmaceutical compositions or medicaments along with suitable carriers or excipients, as is well known in the art. Present methods of treatment can comprise administration of an effective amount of a compound of the invention to a subject in need; e.g., a subject having or at risk for anemia due to, e.g., chronic renal failure, diabetes, cancer, AIDS, radiation therapy, chemotherapy, kidney dialysis, or surgery; or, e.g., a subject having or at risk for ischemia due to, e.g., myocardial infarction, congestive heart failure, cardiac cirrhosis, pulmonary insufficiency, atherosclerosis, peripheral vascular disease, or the like. In a preferred embodiment, the subject is a mammalian subject, and in a most preferred embodiment, the subject is a human subject.

An effective amount of such compound, pharmaceutical composition, or medicament can readily be determined by routine experimentation, as can the most effective and convenient route of administration, and the most appropriate formulation.

Suitable routes of administration may, for example, include oral, rectal, transmucosal, nasal, or intestinal administration and parenteral delivery, including intramuscular, subcutaneous, intramedullary injections, as well as intrathecal, direct intraventricular, intravenous, intraperitoneal, intranasal, or intraocular injections. The agent or composition thereof may be administered in a local rather than a systemic manner. For example, a suitable agent can be delivered via injection or in a targeted drug delivery system, such as a depot or sustained release formulation.

Pharmaceutical dosage forms of a compound of the invention may be provided in an instant release, controlled release, sustained release, or target drug-delivery system. Commonly used dosage forms include, for example, solutions and suspensions, (micro-) emulsions, ointments, gels and patches, liposomes, tablets, dragees, soft or hard shell capsules, suppositories, ovules, implants, amorphous or crystalline powders, aerosols, and lyophilized formulations. Depending on route of administration used, special devices may be required for application or administration of the drug, such as, for example, syringes and needles, inhalers, pumps, injection pens, applicators, or special flasks. Pharmaceutical dosage forms are often composed of the drug, an excipient(s), and a container/closure system. One or multiple excipients, also referred to as inactive ingredients, can be added to a compound of the invention to improve or facilitate manufacturing, stability, administration, and safety of the drug, and can provide a means to achieve a desired drug release profile. Therefore, the type of excipient(s) to be added to the drug can depend on various factors, such as, for example, the physical and chemical properties of the drug, the route of administration, and the manufacturing procedure. Pharmaceutically acceptable excipients are available in the art and include those listed in various pharmacopoeias. (See, e.g., the U.S. Pharmacopeia (USP), Japanese Pharmacopoeia (JP), European Pharmacopoeia (EP), and British pharmacopeia (BP); the U.S. Food and Drug Administration (www.fda.gov) Center for Drug Evaluation and Research (CEDR) publications, e.g., Inactive Ingredient Guide (1996); Ash and Ash, Eds. (2002) *Handbook of Pharmaceutical Additives*, Synapse Information Resources, Inc., Endicott, N.Y.; etc.)

The pharmaceutical compositions of the present invention may be manufactured by any of the methods well-known in the art, such as by conventional mixing, sieving, dissolving, melting, granulating, dragee-making, tabletting, suspending, extruding, spray-drying, levigating, emulsifying, (nano/micro-) encapsulating, entrapping, or lyophilization processes. As noted above, the compositions of the present invention can include one or more physiologically acceptable inactive ingredients that facilitate processing of active molecules into preparations for pharmaceutical use.

Proper formulation is dependent upon the desired route of administration. For intravenous injection, for example, the composition may be formulated in aqueous solution, if necessary using physiologically compatible buffers, including, for example, phosphate, histidine, or citrate for adjustment of the formulation pH, and a tonicity agent, such as, for example, sodium chloride or dextrose. For transmucosal or nasal administration, semisolid, liquid formulations, or patches may be preferred, possibly containing penetration enhancers. Such penetrants are generally known in the art. For oral administration, the compounds can be formulated in liquid or solid dosage forms, and as instant or controlled/sustained release formulations. Suitable dosage forms for oral ingestion by a subject include tablets, pills, dragees, hard and soft shell capsules, liquids, gels, syrups, slurries, suspensions, and emulsions. The compounds may also be formulated in rectal compositions, such as suppositories or retention enemas, e.g., containing conventional suppository bases such as cocoa butter or other glycerides.

Solid oral dosage forms can be obtained using excipients, which may include fillers, disintegrants, binders (dry and wet), dissolution retardants, lubricants, glidants, anti-adherants, cationic exchange resins, wetting agents, antioxidants, preservatives, coloring, and flavoring agents. These excipients can be of synthetic or natural source. Examples of such excipients include cellulose derivatives, citric acid, dicalcium phosphate, gelatine, magnesium carbonate, magnesium/sodium lauryl sulfate, mannitol, polyethylene glycol, polyvinyl pyrrolidone, silicates, silicium dioxide, sodium benzoate, sorbitol, starches, stearic acid or a salt thereof, sugars (i.e., dextrose, sucrose, lactose, etc.), talc, tragacanth mucilage, vegetable oils (hydrogenated), and waxes. Ethanol and water may serve as granulation aides. In certain instances, coating of tablets with, for example, a taste-masking film, a stomach acid resistant film, or a release-retarding film is desirable. Natural and synthetic polymers, in combination with colorants, sugars, and organic solvents or water, are often used to coat tablets, resulting in dragees. When a capsule is preferred over a tablet, the drug powder, suspension, or solution thereof can be delivered in a compatible hard or soft shell capsule.

In one embodiment, the compounds of the present invention can be administered topically, such as through a skin patch, a semi-solid, or a liquid formulation, for example a gel, a (micro-) emulsion, an ointment, a solution, a (nano/micro)-suspension, or a foam. The penetration of the drug into the skin and underlying tissues can be regulated, for example, using penetration enhancers; the appropriate choice and combination of lipophilic, hydrophilic, and amphiphilic excipients, including water, organic solvents, waxes, oils, synthetic and natural polymers, surfactants, emulsifiers; by pH adjustment; and use of complexing agents. Other techniques, such as iontophoresis, may be used to regulate skin penetration of a compound of the invention. Transdermal or topical administration would be preferred, for example, in situations in which local delivery with minimal systemic exposure is desired.

For administration by inhalation, or administration to the nose, the compounds for use according to the present invention are conveniently delivered in the form of a solution, suspension, emulsion, or semisolid aerosol from pressurized packs, or a nebuliser, usually with the use of a propellant, e.g., halogenated carbons derived from methane and ethane, carbon dioxide, or any other suitable gas. For topical aerosols, hydrocarbons like butane, isobutene, and pentane are useful. In the case of a pressurized aerosol, the appropriate dosage unit may be determined by providing a valve to deliver a metered amount. Capsules and cartridges of, for example, gelatin, for use in an inhaler or insufflator, may be formulated. These typically contain a powder mix of the compound and a suitable powder base such as lactose or starch.

Compositions formulated for parenteral administration by injection are usually sterile and can be presented in unit dosage forms, e.g., in ampoules, syringes, injection pens, or in multi-dose containers, the latter usually containing a preservative. The compositions may take such forms as suspensions, solutions, or emulsions in oily or aqueous vehicles, and may contain formulatory agents, such as buffers, tonicity agents, viscosity enhancing agents, surfactants, suspending and dispersing agents, antioxidants, biocompatible polymers, chelating agents, and preservatives. Depending on the injection site, the vehicle may contain water, a synthetic or vegetable oil, and/or organic co-solvents. In certain instances, such as with a lyophilized product or a concentrate, the parenteral formulation would be reconstituted or diluted prior to administration. Depot formulations, providing controlled or sustained release of a compound of the invention, may include injectable suspensions of nano/micro particles or nano/micro or non-micronized crystals. Polymers such as poly(lactic acid), poly(glycolic acid), or copolymers thereof, can serve as controlled/sustained release matrices, in addition to others well known in the art. Other depot delivery systems may be presented in form of implants and pumps requiring incision.

Suitable carriers for intravenous injection for the compounds of the invention are well-known in the art and include water-based solutions containing a base, such as, for example, sodium hydroxide, to form an ionized compound; sucrose or sodium chloride as a tonicity agent; and a buffer, for example, a buffer that contains phosphate or histidine. Co-solvents, such as, for example, polyethylene glycols, may be added. These water-based systems are effective at dissolving compounds of the invention and produce low toxicity upon systemic administration. The proportions of the components of a solution system may be varied considerably, without destroying solubility and toxicity characteristics. Furthermore, the identity of the components may be varied. For example, low-toxicity surfactants, such as polysorbates or poloxamers, may be used, as can polyethylene glycol or other co-solvents, biocompatible polymers such as polyvinyl pyrrolidone may be added, and other sugars and polyols may substitute for dextrose.

A therapeutically effective dose can be estimated initially using a variety of techniques well-known in the art. Initial doses used in animal studies may be based on effective concentrations established in cell culture assays. Suitable dosage range for human can be obtained from such as the data of animal studies and cell culture assays. In certain embodiments, the compounds of the present invention may be prepared as medicament for oral administration. The oral exemplary dose of the compound disclosed herein used in medicament is from about 0.1 to about 10 mg/kg (wherein kg represents the body weight of the subject). In some embodiments, the dosage of compound in medicament is from about 0.5 to about 10 mg/kg (wherein kg represents the body weight of the subject), or optionally from about 0.7 to about 5.0 mg/kg (wherein kg represents the body weight of the subject), or optionally from about 1.0 to about 2.5 mg/kg (wherein kg represents the body weight of the subject). Dosage regimen for oral administration agent typically is three times a week, twice a week, once a week, three times daily, twice daily or once daily.

An effective amount, or a therapeutically effective amount, or dose of the medicament (e.g., compound of the invention) refers to the amount of the medicament or compound which ameliorates the disease symptoms in subject or prolongs survival of the subject. Toxicity and therapeutic efficacy of such molecules can be determined by standard pharmaceutical procedures in cell cultures or experimental animals, e.g., by determining the $LD_{50}$ (the dose lethal to 50% of the population) and the $ED_{50}$ (the dose therapeutically effective in 50% of the population). The dose ratio of toxic to therapeutic effects is the therapeutic index, which can be expressed as the ratio $LD_{50}/ED_{50}$. Agents that exhibit high therapeutic indices are preferred.

The effective amount or therapeutically effective amount is the amount of the compound or pharmaceutical composition that will elicit the biological or medical response of a tissue, system, animal or human that is being sought by the researcher, veterinarian, medical doctor or other clinician. Dosages particularly fall within a range of circulating concentrations that includes the $ED_{50}$ with little or no toxicity. Dosages may vary within this range depending upon the dosage form employed and/or the route of administration utilized. The exact formulation, route of administration, dosage, and dosage interval should be chosen according to methods known in the art, in view of the specifics of a subject's condition.

Dosage amount and interval may be adjusted individually to provide plasma levels of the active moiety that are sufficient to achieve the desired effects; i.e., the minimal effective concentration (MEC). The MEC will vary for each compound but can be estimated from, for example, in vitro data and animal experiments. Dosages necessary to achieve the MEC will depend on individual characteristics and route of administration. In cases of local administration or selective uptake, the effective local concentration of the drug may not be related to plasma concentration.

The amount of compound or composition administered may be dependent on a variety of factors, including the sex, age, and weight of the subject being treated, the severity of the affliction, the manner of administration, and the judgment of the prescribing physician.

The present compositions may, if desired, be presented in a pack or dispenser device containing one or more unit dosage forms containing the active ingredient. Such a pack or device may, for example, comprise metal or plastic foil, such as a blister pack; or glass and rubber stoppers such as in vials. The pack or dispenser device may be accompanied by instructions for administration. Compositions comprising a compound of the invention formulated in a compatible pharmaceutical carrier may also be prepared, placed in an appropriate container, and labeled for treatment of an indicated condition.

The compounds according to the invention can be employed by themselves or, if required, in combination with other active compounds. The present invention moreover provides medicaments comprising at least one of the compounds according to the invention and one or more further active compounds, in particular for treatment and/or prevention of the above mentioned diseases. Suitable active compounds in the combination which may be mentioned by way of example and preferably are: ACE inhibitors, angiotensin II receptor antagonists, beta receptor blockers, calcium antagonists, PDE inhibitors, mineralocorticoid receptor antagonists, diuretics, aspirin, iron supplements, vitamin B12 and folic acid supplements, statins, digitalis (digoxin) derivatives, tumor chemotherapeutics and antibiotics.

The compounds of the present invention can be used to inhibit HIF hydroxylase activity, thereby modulating the stability and/or activity of HIF and activating HIF-regulated gene expression. The compound, or composition or medicament thereof, can be used in methods to treat, pretreat, or delay progression or onset of conditions mediated at least in part by HIF, including, but not limited to, anemia and various aspects of ischemic and hypoxic conditions.

In one embodiment, the compound can be administered after diagnosis of disease related to ischemic condition, such as, myocardial infarction, pulmonary embolism, intestinal infarction, ischemic stroke, renal ischemic-reperfusion injury, cardiac cirrhosis, macular degeneration, pulmonary embolism, chronic kidney disease, transient cerebral ischemia, peripheral vascular disease, acute respiratory failure, neonatal respiratory distress syndrome, congestive heart failure, etc. In yet another embodiment, the compound is administered immediately after a trauma or injury. In other embodiments, the compound, or composition or medicament thereof, can be administered to a subject based on predisposing conditions, e.g., hypertension, diabetes, occlusive arterial disease, chronic venous insufficiency, Raynaud's disease, chronic skin ulcers, cirrhosis, congestive heart failure, and systemic sclerosis. In still other embodiments, compounds may be administered to a subject to decrease or prevent the development of tissue damage associated with ischemia or hypoxia.

In a particular embodiment, the compounds of the present invention can be used to increase endogenous erythropoietin (EPO). The compounds disclosed herein can be used for preventing, pretreating, or treating EPO-associated conditions, including, e.g., conditions associated with anemia and neurological disorders. Conditions associated with anemia include disorders such as acute or chronic kidney disease, diabetes, cancer, ulcers, infection with virus, e.g., HIV, bacteria, or parasites; inflammation, etc. Anemic conditions can further include those associated with procedures or treatments including, e.g., radiation therapy, chemotherapy, dialysis, and surgery. Disorders associated with anemia additionally include abnormal hemoglobin and/or erythrocytes, such as found in disorders such as microcytic anemia, hypochromic anemia, aplastic anemia, etc.

The compound of the invention can be used to increase endogenous EPO in a subject undergoing a specific treatment or procedure, prophylactically or concurrently, for example, an HIV-infected anemic patient being treated with azidothymidine (zidovudine) or other reverse transcriptase inhibitors, an anemic cancer patient receiving cyclic cisplatin- or non-cisplatin-containing chemotherapeutics, or an anemic or non-anemic patient scheduled to undergo surgery. Additionally, the compounds can be used to increase endogenous EPO level in an anemic or non-anemic patient scheduled to undergo surgery to reduce the need for allogenic blood transfusions or to facilitate banking of blood prior to surgery.

General Synthetic Procedures

In the present specification, if the chemical name of the compound doesn't match the corresponding structure, the compound is characterized by the corresponding structure.

Generally, the compounds disclosed herein may be prepared by methods described herein, wherein the substituents are as defined for Formula (I) above, except where further noted. The following non-limiting schemes and examples are presented to further exemplify the invention.

Persons skilled in the art will recognize that the chemical reactions described may be readily adapted to prepare a number of other compounds disclosed herein, and alternative methods for preparing the compounds disclosed herein are deemed to be within the scope disclosed herein. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds disclosed herein.

In the examples described below, unless otherwise indicated, all temperatures are set forth in degrees Celsius. Unless otherwise specified, the agents were purchased from Aldrich Chemical Company, Arco Chemical Company and Alfa Chemical Company, which were used directly without further purification. Common solvents were purchased from commercial suppliers such as Shantou XiLong Chemical Factory, Guangdong Guanghua Reagent Chemical Factory Co. Ltd., Guangzhou Reagent Chemical Factory, Tianjin YuYu Fine Chemical Ltd., Qingdao Tenglong Reagent Chemical Ltd., and Qingdao Ocean Chemical Factory.

Anhydrous tetrahydrofuran, dioxane, toluene and ether were obtained by refluxing the solvent with sodium. Anhydrous dichloromethane and chloroform were obtained by refluxing the solvent with calcium hydride. Ethyl acetate, petroleum ether, n-hexane, N,N-dimethylacetamide and N,N-dimethylforamide were treated with anhydrous sodium sulfate prior use.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was conducted using a silica gel column. Silica gel (300-400 mesh) was purchased from Qingdao Ocean Chemical Factory. $^1$H NMR spectra were recorded by a Bruker Avance 400 MHz spectrometer or Bruker Avance III HD 600 spectrometer, using $CDCl_3$, DMSO-$d_6$, $CD_3OD$ or acetone-$d_6$ (reported in ppm) as solvent, and using TMS (0 ppm) or chloroform (7.25 ppm) as the reference standard. When peak multiplicities are reported, the following abbreviations are used: s (singlet), d (doublet), t (triplet), m (multiplet), br (broadened), br (doublet of doublets), dt (doublet of triplets), ddd (doublet of doublet of doublets), ddt (doublet of doublet of triplets), dddd (doublet of doublet of doublet of doublets). Coupling constants, when given, were reported in Hertz (Hz).

Low-resolution mass spectral (MS) data were determined by an Agilent 6320 Series LC-MS spectrometer equipped with a G1312A binary pump and a G1316A TCC (column was operated at 30° C.). G1329A autosampler and G1315B DAD detector were applied in the analysis, and an ESI source was used in the LC-MS spectrometer.

Low-resolution mass spectral (MS) data were determined by an Agilent 6120 Series LC-MS spectrometer equipped with a G1311A quaternary pump and a G1316A TCC (column was operated at 30° C.). G1329A autosampler and G1315D DAD detector were applied in the analysis, and an ESI source was used on the LC-MS spectrometer.

Both LC-MS spectrometers were equipped with an Agilent Zorbax SB-C18, 2.1×30 mm, 5 μm column. Injection volume was decided by the sample concentration. The flow rate was 0.6 mL/min. The HPLC peaks were recorded by UV-Vis wavelength at 210 nm and 254 nm. The mobile phase was 0.1% formic acid in acetonitrile (phase A) and 0.1% formic acid in ultrapure water (phase B). The gradient elution conditions were shown in Table 1:

TABLE 1

The gradient condition of the mobile phase in Low-resolution mass spectrum analysis

| Time (min) | A ($CH_3CN$, 0.1% HCOOH) | B ($H_2O$, 0.1% HCOOH) |
|---|---|---|
| 0-3 | 5-100 | 95-0 |
| 3-6 | 100 | 0 |
| 6-6.1 | 100-5 | 0-95 |
| 6.1-8 | 5 | 95 |

The following abbreviations are used throughout the specification:
$CDCl_3$ deuterated chloroform
DMF-$d_7$ deuterated N,N-dimethylformamide
DMSO-$d_6$ deuterated dimethyl sulfoxide Acetone-$d_6$ deuterated acetone
EA, EtOAc ethyl acetate
DMF N,N-dimethylformamide
g gram
mg milligram
mol mole
mmol millimole
h hour, hours
min minute, minutes
mL milliliter μL microliter EPO erythropoietin ATCC American Type Culture Collection The following schemes describe the preparation procedure of the compound disclosed herein. wherein, unless otherwise specified, $R^a$ is H, Cl or Br; each $R^{a1}$ is independently H, F, Cl or Br; each $R^b$ is independently methyl or ethyl; $R^c$ is OH, Cl or Br; $Hal^1$ is I, Br or Cl; each $Hal^2$ and $Hal^3$ is independently Br or Cl; Y is Cl, Br, I or OH; $L^a$ is —$(CR^{11}R^{12})_q$—; $L^b$ is —O— or —$N(R^{13})$—; r is 0, 1, 2 or 3; $R^1$, $R^2$, $R^3$, $R^4$, $R^5$, $R^{10}$, $R^{11}$, $R^{12}$, $R^{13}$, L and q are as defined herein.

Schemes

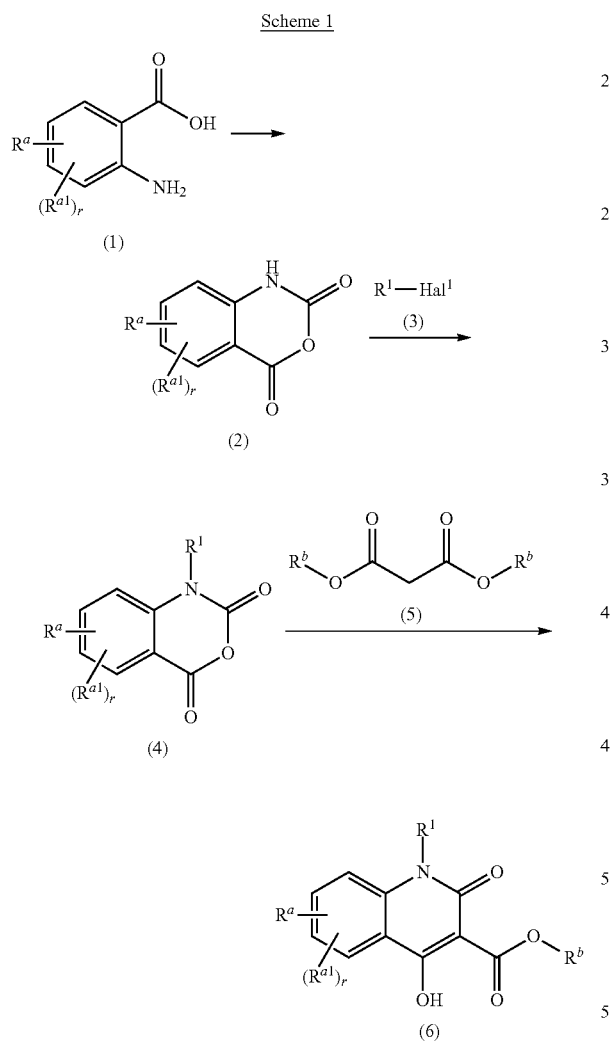

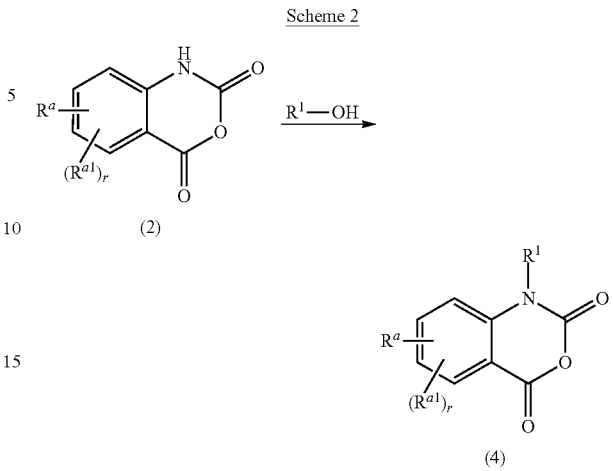

Compound (4) as an intermediate disclosed herein can be prepared by the procedure illustrated in scheme 2. Compound (2) can undergo substitution reaction with $R^1OH$ in the presence of triphenylphosphine and diisopropyl azodiformate to give compound (4).

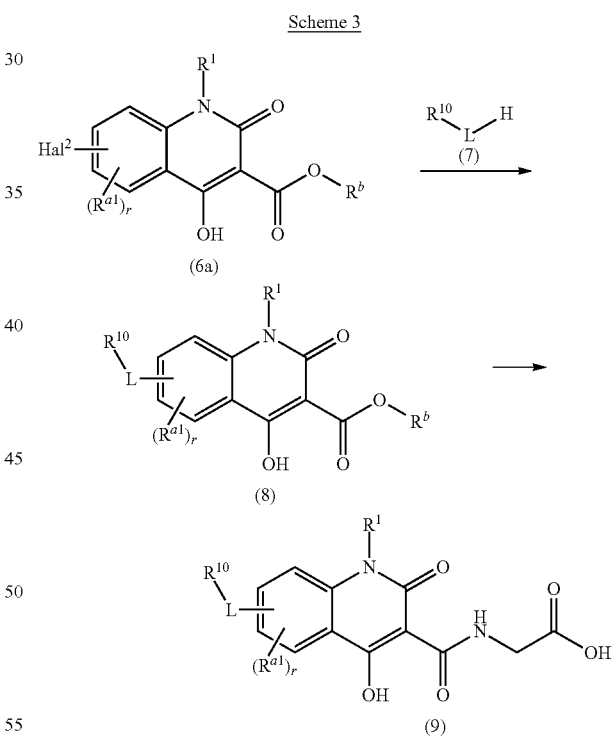

Compound (6) as an intermediate can be prepared by the procedure illustrated in scheme 1. Compound (1) can react with triphosgene in a solvent (e.g., THF, etc.) to give compound (2). Compound (2) can undergo substitution reaction with compound (3) in the presence of a base (such as sodium hydride, potassium carbonate, etc.) to give compound (4). Compound (4) can react with compound (5) in the presence of a base (e.g., sodium tert-butoxide, etc.) to give compound (6).

Compound (9) can be prepared by the procedure illustrated in scheme 3. Compound (6a) can undergo coupling reaction with compound (7) under a base condition (e.g., potassium carbonate, cesium carbonate, etc.) in the presence of a catalyst (e.g., cuprous iodide, cuprous chloride, etc.) and a ligand (e.g., (1R,2R)—N,N'-dimethyl-1,2-cyclohexanediamine, $N^1,N^2$-dimethylhexanediamine, N,N-dimethylglycine, etc.) to give compound (8). Compound (8) can react with sodium glycinate under heating condition to give compound (9).

Scheme 4

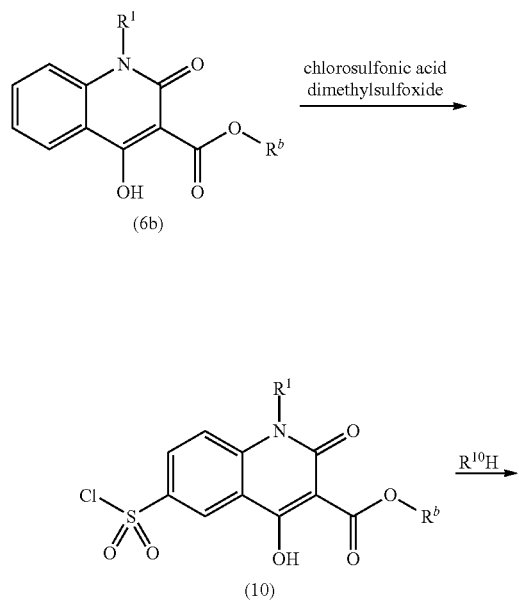

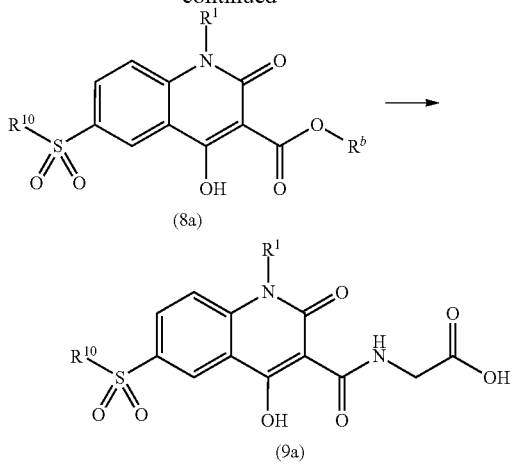

Compound (9a) as an intermediate can be prepared by the procedure illustrated in scheme 4. Compound (6a) can react with chlorosulfonic acid and dimethyl sulfoxide to give compound (10). Compound (10) can undergo substitution reaction with $R^{10}H$ in the presence of a base (e.g., sodium hydroxide, potassium carbonate, etc.) to give compound (8a). Compound (8a) can react with sodium glycinate under a heating condition to give compound (9a).

Scheme 5
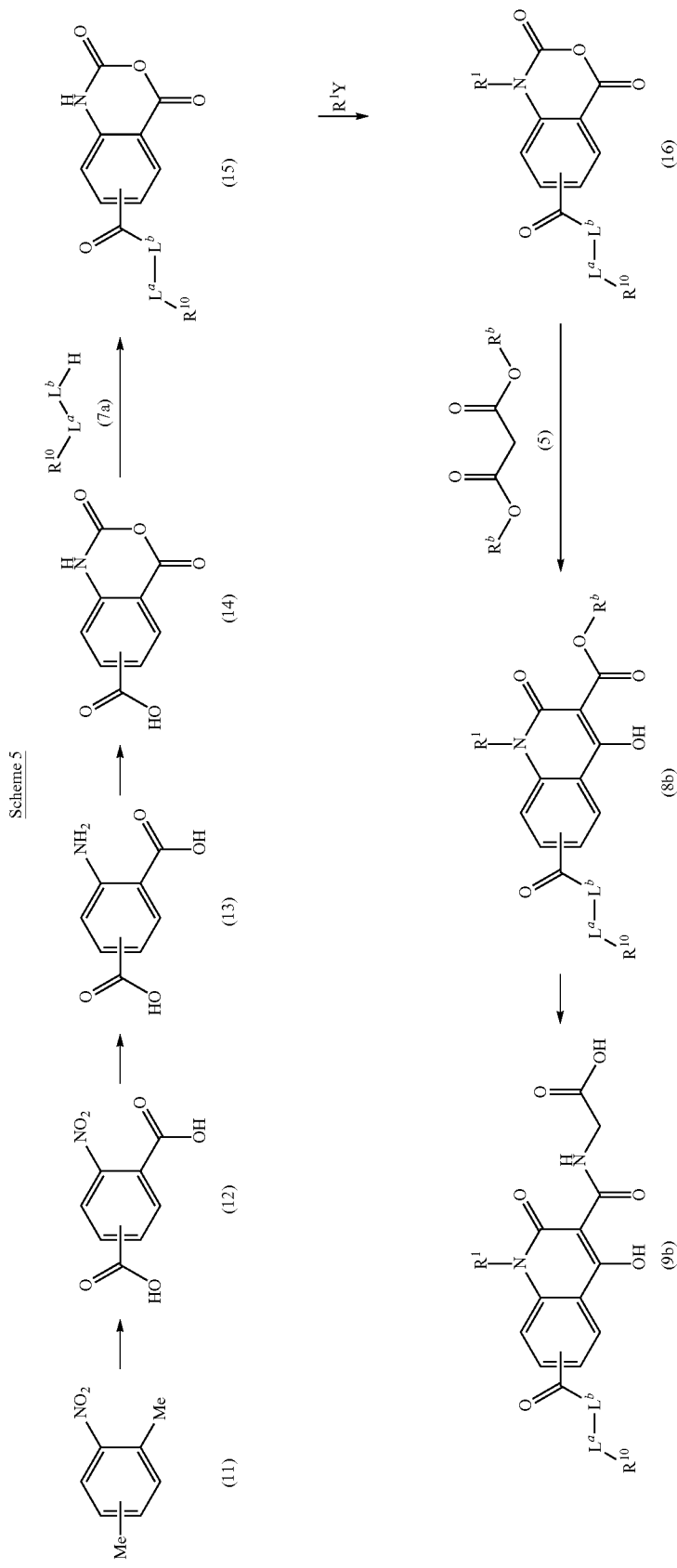

Compound (9b) as an intermediate can be prepared by the procedure illustrated in scheme 5. Compound (11) can undergo oxidizing reaction in the presence of an oxidizing agent (e.g., potassium permanganate, etc.) to give compound (12). The nitro group of compound (12) can be reduced in the presence of an appropriate reducing agent (such as hydrazine hydrate, etc.) to give compound (13). Compound (13) can react with triphosgene in a solvent (e.g., THF) to give compound (14). Compound (14) can undergo condensation reaction with compound (7a) in the presence of a condensation reagent (such as HATU, etc.) and a base (such as N,N-diisopropylethylamine, etc.) to give compound (15). Compound (15) can undergo substitution reaction with WY under a suitable condition (such as in the presence of a base, e.g. sodium hydroxide or potassium carbonate, etc., or reagents, e.g. triphenylphosphine and diisopropyl azodiformate, etc.) to give compound (16). Compound (16) can react with compound (5) in the presence of a base (e.g., sodium tert-butoxide, etc.) to give compound (8b). Compound (8b) can react with sodium glycinate under heating condition to give compound (9b).

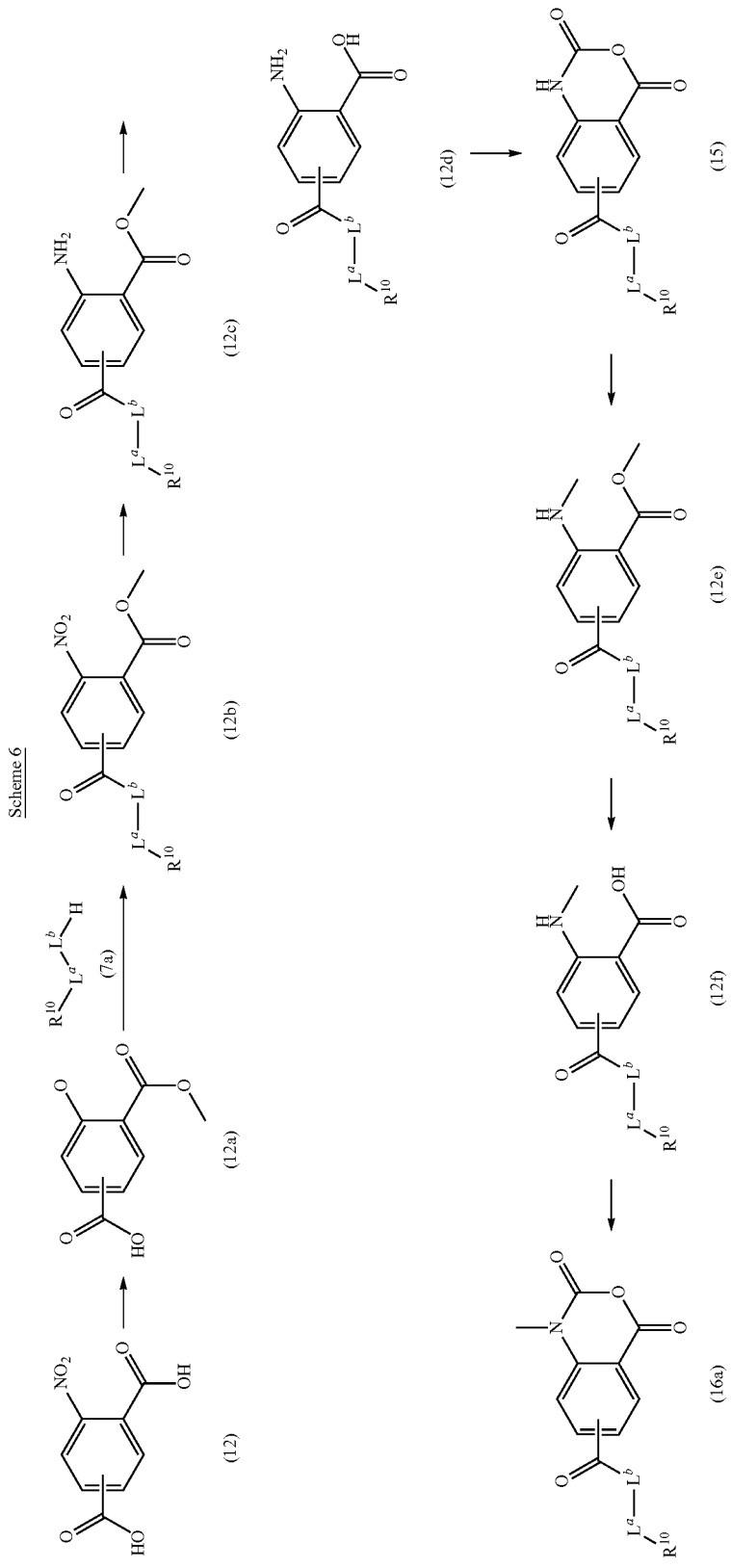
Scheme 6

Compound (15) as an intermediate disclosed herein can be prepared by the procedure illustrated in scheme 6. Compound (12) can convert to a dimethyl ester in methanol in the presence of concentrated sulfuric acid, following by hydrolysis in the presence of a base (such as sodium hydroxide, etc.) to give a monoester compound (12a). Compound (12a) can react with compound (7a) under an appropriate condition (such as in the presence of a base, e.g., triethylamine, pyridine, etc., or in the presence of both a condensation reagent, e.g., HATU, etc., and a base e.g., N,N-diisopropylethylamine, etc.). The nitro group of compound (12b) can be reduced under an appropriate condition (for example, the reaction can occur in a hydrogen atmosphere in the presence of Pd/C, etc.) to give compound (12c). Compound (12c) can be hydrolyzed in the presence of a base (such as sodium hydroxide, etc.) to give compound (12d). Compound (12d) can react with triphosgene in a solvent (e.g., THF, etc.) to give compound (15). Compound (15) can convert to compound (12e) in the presence of a base (such as potassium carbonate, etc.) and iodomethane. Compound (12e) can be hydrolyzed in the presence of a base (such as lithium hydroxide, etc.) to give compound (121). Compound (12f) can react with triphosgene in a solvent (e.g., THF, etc.) to give compound (16a).

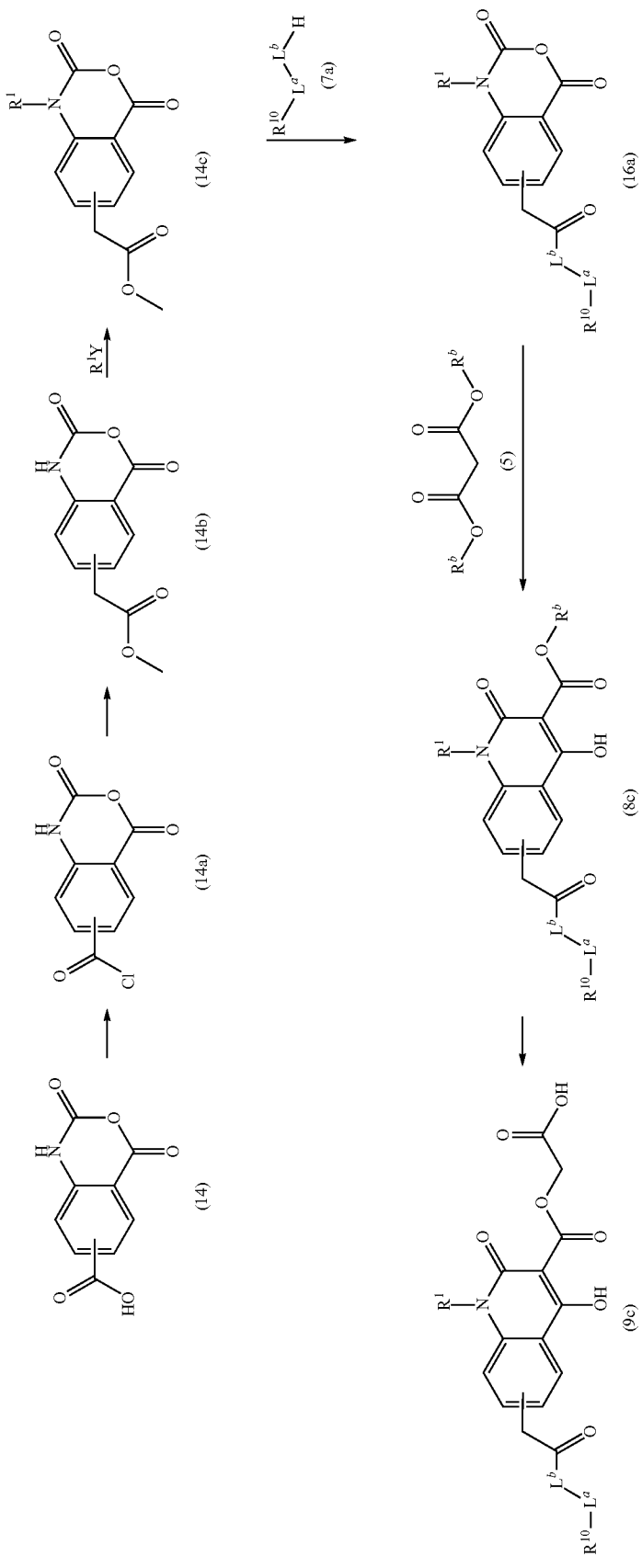

Compound (9c) as an intermediate can be prepared by the procedure illustrated in scheme 7. Compound (14) can undergo halogenating reaction in the presence of a suitable reagent (such as thionyl chloride, oxalyl chloride, etc.) to give compound (14a). Compound (14a) can undergo Arndt-Eister reaction in the presence of a suitable reagent (such as diazomethane, trimethylsilylmethyl azide or 1-trimethylsilylmethyl-benzotriazole) to give compound (14b). Compound (14b) can undergo substitution reaction with $R^1Y$ under a suitable condition (such as in the presence of a base, e.g., sodium hydroxide or potassium carbonate, or reagents, e.g., triphenylphosphine and diisopropyl azodiformate) to give compound (14c). Compound (14c) can undergo condensation reaction with compound (7a) in the presence of a condensation reagent (such as HATU, etc.) and a base (such as N,N-diisopropylethylamine, etc.) to give compound (16a). Compound (16a) can react with compound (5) in the presence of a base (e.g., sodium tert-butoxide) to give compound (8c). Compound (8c) can react with sodium glycinate under a heating condition to give compound (9c).

The following examples disclosed herein are presented to further describe the invention. However, these examples should not be used to limit the scope of the invention.

EXAMPLES

Example 1: 2-(4-hydroxy-1-methyl-2-oxo-7-phenoxy-1,2-dihydroquinoline-3-carboxamido)acetic acid

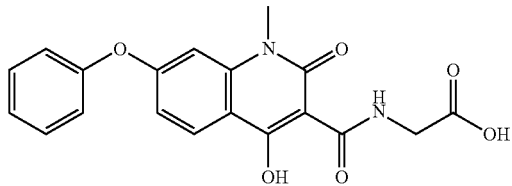 [SMILES: Cn1c(=O)c(C(=O)NCC(=O)O)c(O)c2ccc(Oc3ccccc3)cc21]

Step 1: 7-bromo-1H-benzo[d][1,3]oxazine-2,4-dione

To a solution of 2-amino-4-bromobenzoic acid (10.0 g, 46.3 mmol) in tetrahydrofuran (100 mL) was added triphosgene (4.54 g, 15.3 mmol). The mixture was stirred at 80° C. overnight under nitrogen protection. The reaction mixture was cooled to room temperature and poured into ice-water (120 mL), then the resulting mixture was filtered. The filter cake was washed with water and ethyl ether in turn, and dried in oven to give a brown solid (7.60 g, 68.0%).

MS (ESI, neg.ion) m/z: 240.1 (M−1);
$^1$H NMR (400 MHz, DMSO-$d_6$) δ (ppm): 11.94 (s, 1H), 7.81 (d, J=8.0 Hz, 1H), 7.48-7.26 (m, 2H).

Step 2: 7-bromo-1-methyl-1H-benzo[d][1,3]oxazine-2,4-dione

To a three-neck round-bottom flask were added sodium hydride (0.54 g, 13.50 mmol) and N,N-dimethylformamide (20 mL) in turn under nitrogen protection. The mixture was cooled to 0° C., and 7-bromo-1H-benzo[d][1,3]oxazine-2,4-dione (2.70 g, 11.00 mmol) was added. The resulting mixture was stirred at room temperature for 1 h, then iodomethane (760 μL, 12.00 mmol) was added dropwise, and the mixture was stirred for 16 h at room temperature. The reaction mixture was poured into ice-water (50 mL), then the resulting mixture was filtered. The filter cake was washed with water and ethyl ether in turn, and dried in oven to give a brown solid (1.36 g, 47.5%).

MS (ESI, pos.ion) m/z: 255.9 (M+1).

Step 3: methyl 7-bromo-4-hydroxy-1-methyl-2-oxo-1,2-dihydroquinoline-3-carboxylate To a stirred solution of 7-bromo-1-methyl-1H-benzo[d][1,3]oxazine-2,4-dione (0.50 g, 1.95 mmol) in N,N-dimethylformamide (15 mL) was added a solution of sodium tert-butoxide (0.38 g, 3.95 mmol) and dimethyl malonate (450 μL, 3.90 mmol) in N,N-dimethylformamide (5 mL). The mixture was heated to 100° C. and stirred for 2 h under nitrogen protection. The mixture was cooled to room temperature and concentrated in vacuo to remove the solvent. The residue was acidified with diluted hydrochloric acid (2 M) to pH 4, and the resulting mixture was extracted with dichloromethane (20 mL×2). The combined organic layers were washed with saturated brine (20 mL), dried over anhydrous sodium sulfate, filtered and concentrated in vacuo to remove the solvent. The residue was purified by column chromatography (ethyl acetate/dichloromethane (v/v)=1/2) to give a light yellow solid (208 mg, 34.1%).

$^1$H NMR (400 MHz, CDCl$_3$) δ (ppm): 14.10 (s, 1H), 8.04 (d, J=8.6 Hz, 1H), 7.50 (d, J=1.2 Hz, 1H), 7.39 (dd, J=8.6, 1.4 Hz, 1H), 4.05 (s, 3H), 3.63 (s, 3H).

Step 4: methyl 4-hydroxy-1-methyl-2-oxo-7-phenoxy-1,2-dihydroquinoline-3-carboxylate To a two-neck round-bottom flask were added methyl 7-bromo-4-hydroxy-1-methyl-2-oxo-1,2-dihydroquinoline-3-carboxylate (208 mg, 0.67 mmol), phenol (0.1 mL, 1.00 mmol), cesium carbonate (550 mg, 1.69 mmol), cuprous iodide (26 mg, 0.14 mmol), N,N-dimethylglycine (28 mg, 0.27 mmol) and dimethyl sulfoxide (10 mL) in turn under nitrogen protection. The mixture was stirred at 120° C. overnight. The mixture was cooled to room temperature and acidified with diluted hydrochloric acid (1 M) to pH 4, then the resulting mixture was extracted with ethyl acetate (25 mL×3). The combined organic layers were washed with water (20 mL×2) and saturated brine (40 mL), dried over anhydrous sodium sulfate, filtered and concentrated in vacuo to remove the solvent. The residue was purified by column chromatography (petroleum ether/ethyl acetate (v/v)=1/1) to give a light yellow solid (126.1 mg, 58.2%).

MS (ESI, pos.ion) m/z: 326.2 (M+1).

Step 5: 2-(4-hydroxy-1-methyl-2-oxo-7-phenoxy-1,2-dihydroquinoline-3-carboxamido)acetic acid To a solution of methyl 4-hydroxy-1-methyl-2-oxo-7-phenoxy-1,2-dihydroquinoline-3-carboxylate (126.1 mg, 0.39 mmol) in ethylene glycol monomethyl ether (20 mL) was added sodium glycinate (80 mg, 0.82 mmol). The mixture was stirred at 130° C. for 2 h under nitrogen protection. The mixture was cooled to room temperature and concentrated in vacuo to remove the solvent. To the residue was added water (25 mL), and the mixture was washed with ethyl acetate (15 mL×3). The aqueous layer was acidified with hydrochloric acid (1 M) to pH 1, and the resulting mixture was extracted with ethyl acetate (25 mL×3). The combined organic layers were washed with saturated brine (30 mL), dried over anhydrous sodium sulfate, and filtered. The filtrate was concentrated in vacuo to dry to give a yellow solid (57.8 mg, 40.5%).

MS (ESI, pos.ion) m/z: 369.0 (M+1);
$^1$H NMR (400 MHz, Acetone-$d_6$) δ (ppm): 8.14 (s, 1H), 7.51 (s, 2H), 7.21 (t, J=35.4 Hz, 4H), 6.94 (s, 1H), 4.26 (s, 2H), 3.61 (s, 3H).

Example 2: 2-(1-(cyclopropylmethyl)-4-hydroxy-2-oxo-7-phenoxy-1,2-dihydroquinoline-3-carboxamido)acetic acid

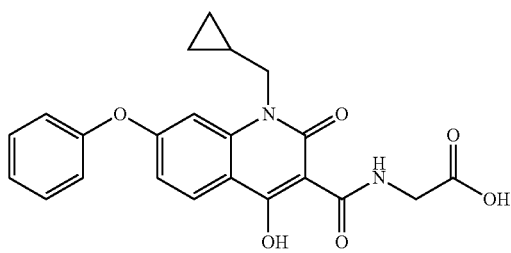 [SMILES: O=C(O)CNC(=O)c1c(O)c2ccc(Oc3ccccc3)cc2n(CC2CC2)c1=O]

Step 1: 7-bromo-1-(cyclopropylmethyl)-1H-benzo[d][1,3]oxazine-2,4-dione

To a stirred solution of 7-bromo-1H-benzo[d][1,3]oxazine-2,4-dione (2.39 g, 9.87 mmol), cyclopropanemethanol (0.782 g, 10.8 mmol) and triphenylphosphine (3.88 g, 14.8 mmol) in tetrahydrofuran (80 mL) at 0° C. was added dropwise diisopropyl azodicarboxylate (2.99 g, 14.8 mmol) under nitrogen protection. After the addition, the mixture was stirred at 0° C. for 1 h, then further stirred at room temperature for 4 h. The reaction mixture was concentrated in vacuo or remove the solvent. The residue was purified by column chromatography (petroleum ether/ethyl acetate (v/v)=40/1) to give a white solid (1.30 g, 44.5%).

MS (ESI, pos.ion) m/z: 295.9 (M+1).

Step 2: methyl 7-bromo-1-(cyclopropylmethyl)-4-hydroxy-2-oxo-1,2-dihydroquinoline-3-carboxylate To a stirred solution of 7-bromo-1-(cyclopropylmethyl)-1H-benzo[d][1,3]oxazine-2,4-dione (1.30 g, 4.39 mmol) in N,N-dimethylformamide (15 mL) was added a solution of sodium tert-butoxide (0.675 g, 7.02 mmol) and dimethyl malonate (1.16 g, 8.78 mmol) in N,N-dimethylformamide (5 mL). The mixture was stirred at 100° C. for 2 h. The mixture was cooled to room temperature and concentrated in vacuo to remove the solvent. The residue was acidified with diluted hydrochloric acid (2 M) to pH 5, and the resulting mixture was extracted with dichloromethane (20 mL×2). The combined organic layers were washed with saturated brine (20 mL), dried over anhydrous sodium sulfate and filtered. The filtrate was concentrated in vacuo to remove the solvent. The residue was purified by column chromatography (petroleum ether/ethyl acetate (v/v)=10/1) to give a white solid (0.60 g, 38.8%).

MS (ESI, pos.ion) m/z: 352.1 (M+1).

Step 3: methyl 1-(cyclopropylmethyl)-4-hydroxy-2-oxo-7-phenoxy-1,2-dihydroquinoline-3-carboxylate To a round-bottom flask were added methyl 7-bromo-1-(cyclopropylmethyl)-4-hydroxy-2-oxo-1,2-dihydroquinoline-3-carboxylate (0.60 g, 1.70 mmol), phenol (0.192 g, 2.04 mmol), N,N-dimethylglycine (0.053 g, 0.51 mmol), cuprous iodide (0.065 g, 0.34 mmol), cesium carbonate (1.40 g, 4.30 mmol) and dimethyl sulfoxide (12 mL) in turn under nitrogen protection. The mixture was stirred at 140° C. for 18 h. The mixture was cooled to room temperature. The mixture was acidified with diluted hydrochloric acid (1 M) to pH 5, and the resulting mixture was extracted with dichloromethane (30 mL×3). The combined organic layers were washed with water (15 mL×3) and saturated brine (20 mL), dried over anhydrous sodium sulfate. The reaction mixture was filtered and the filtrate was concentrated in vacuo to remove the solvent. The residue was purified by column chromatography (petroleum ether/ethyl acetate (v/v)=4/1) to give a white solid (0.37 g, 59.4%).

MS (ESI, pos.ion) m/z: 366.3 (M+1).

Step 4: 2-(1-(cyclopropylmethyl)-4-hydroxy-2-oxo-7-phenoxy-1,2-dihydroquinoline-3-carboxamido) acetic acid To a round-bottom flask were added methyl 1-(cyclopropylmethyl)-4-hydroxy-2-oxo-7-phenoxy-1,2-dihydroquinoline-3-carboxylate (0.37 g, 1.01 mmol), ethylene glycol monomethyl ether (20 mL) and sodium glycinate (0.158 g, 1.63 mmol) in turn. The mixture was stirred at 130° C. for 2 h. The mixture was cooled to room temperature and concentrated in vacuo to remove the solvent. To the residue was added water (20 mL), and the mixture was washed with ethyl acetate (20 mL×3). The aqueous layer was acidified with diluted hydrochloric acid (2 M) to pH 3, and the resulting mixture was extracted with ethyl acetate (25 mL×3). The combined organic layers were washed with saturated brine (30 mL), dried over anhydrous sulfate, and filtered. The filtrate was concentrated in vacuo to remove the solvent and give a white solid (82 mg, 20%).

MS (ESI, pos.ion) m/z: 409.0 (M+1);
$^1$H NMR (400 MHz, DMSO-$d_6$) δ (ppm): 12.91 (s, 1H), 10.45 (t, J=5.2 Hz, 1H), 8.16-8.04 (m, J=8.6, 5.8 Hz, 1H), 7.50 (t, J=7.7 Hz, 2H), 7.29 (t, J=7.3 Hz, 1H), 7.21 (d, J=8.3 Hz, 3H), 7.02-6.88 (m, 1H), 4.20-4.01 (m, J=6.2 Hz, 4H), 1.18-1.02 (m, 1H), 0.44 (d, J=7.8 Hz, 2H), 0.36 (d, J=4.3 Hz, 2H).

Example 3: 2-(4-hydroxy-1-methyl-2-oxo-6-(2-phenylacetamido)-1,2-dihydroquinoline-3-carboxamido) acetic acid

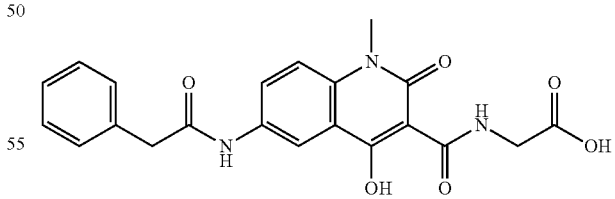

Step 1: 6-bromo-1H-benzo[d][1,3]oxazine-2,4-dione

2-Amino-5-bromobenzoic acid (10.00 g, 46.29 mmol) was dissolved in tetrahydrofuran (100 mL), then to the solution was added triphosgene (9.80 g, 33.00 mmol). The mixture was stirred at 80° C. for 4 h under nitrogen protection. The reaction mixture was cooled to room temperature and poured into ice-water (120 mL), then the resulting mixture was filtered. The filter cake was washed with water and ethyl ether in turn, and dried in oven to give a white solid (10.6 g, 94.6%).

MS (ESI, pos.ion) m/z: 242.1 (M+1);
$^1$H NMR (400 MHz, DMSO-d$_6$) δ (ppm): 11.86 (s, 1H), 8.05-7.83 (m, 2H), 7.11 (d, J=8.7 Hz, 1H).

Step 2: 6-bromo-1-methyl-1H-benzo[d][1,3]oxazine-2,4-dione

To a three-neck round-bottom flask were added successively sodium hydride (0.54 g, 13.50 mmol) and N,N-dimethylformamide (25 mL) under nitrogen protection. The mixture was cooled to 0° C., and 6-bromo-1H-benzo[d][1,3]oxazine-2,4-dione (2.70 g, 11.00 mmol) was added. The resulting mixture was stirred at room temperature for 1 h, then iodomethane (760 μL, 12.00 mmol) was added, and the mixture was stirred for 16 h at room temperature. The reaction mixture was poured into ice-water (50 mL), then the resulting mixture was filtered. The filter cake was washed with water and ethyl ether in turn, and dried in oven to give a pale solid (1.29 g, 45.10%).

MS (ESI, pos.ion) m/z: 255.9 (M+1);
$^1$H NMR (400 MHz, DMSO-d$_6$) δ (ppm): 8.10-7.96 (m, 2H), 7.41 (d, J=8.8 Hz, 1H), 3.45 (s, 3H).

Step 3: methyl 6-bromo-4-hydroxy-1-methyl-2-oxo-1,2-dihydroquinoline-3-carboxylate To a stirred solution of 6-bromo-1-methyl-1H-benzo[d][1,3]oxazine-2,4-dione (1.29 g, 5.04 mmol) in N,N-dimethylformamide (20 mL) was added a solution of sodium tert-butoxide (1.00 g, 10.4 mmol) and dimethyl malonate (1.2 mL, 10.0 mmol) in N,N-dimethylformamide (10 mL). The mixture was stirred at 100° C. for 2 h. The mixture was cooled to room temperature and concentrated in vacuo to remove the solvent. The residue was acidified with diluted hydrochloric acid (1 M) to pH 5, and the resulting mixture was extracted with dichloromethane (20 mL×2). The combined organic layers were washed with saturated brine (20 mL), dried over anhydrous sodium sulfate, filtered and concentrated in vacuo to remove the solvent. The residue was purified by column chromatography (ethyl acetate/dichloromethane (v/v)=1/2) to give a light yellow solid (777 mg, 49.6%).

MS (ESI, pos.ion) m/z: 312.1 (M+1).

Step 4: methyl 4-hydroxy-1-methyl-2-oxo-6-(2-phenylacetamido)-1,2-dihydroquinoline-3-carboxylate To a microwave tube were added methyl 6-bromo-4-hydroxy-1-methyl-2-oxo-1,2-dihydroquinoline-3-carboxylate (300 mg, 0.96 mmol), 2-phenylacetamide (156 mg, 1.15 mmol), cuprous iodide (37 mg, 0.19 mmol), cesium carbonate (783 mg, 2.40 mmol), N,N-dimethylformamide (5 mL) and (1R,2R)—N$^1$,N$^2$-dimethyl-1,2-cyclohexanediamine (61 μL, 0.38 mmol) in turn. The mixture was stirred at 220° C. for 30 min under microwave irradiation and under nitrogen protection. The mixture was cooled to room temperature and quenched with water (10 mL). The mixture was acidified with diluted hydrochloric acid (2 M) to pH 3, and the resulting mixture was extracted with ethyl acetate (20 mL×2). The combined organic layers were washed with water (10 mL) and saturated brine (20 mL), dried over anhydrous sodium sulfate, and filtered. The filtrate was concentrated in vacuo to give a yellow solid (190 mg, 54.0%).

MS (ESI, pos.ion) m/z: 367.0 (M+1).

Step 5: 2-(4-hydroxy-1-methyl-2-oxo-6-(2-phenylacetamido)-1,2-dihydroquinoline-3-carboxamido) acetic acid Methyl 4-hydroxy-1-methyl-2-oxo-6-(2-phenylacetamido)-1,2-dihydroquinoline-3-carboxylate (190 mg, 0.519 mmol) was dissolved in ethylene glycol monomethyl ether (25 mL), then to the solution was added sodium glycinate (101 mg, 1.04 mmol). The mixture was stirred at 130° C. for 2 h under nitrogen protection. The mixture was cooled to room temperature and concentrated in vacuo to remove the solvent. To the residue was added water (25 mL), and the mixture was washed with ethyl acetate (15 mL×3). The aqueous layer was acidified with hydrochloric acid (1 M) to pH 1, and the resulting mixture was extracted with ethyl acetate (25 mL×3). The combined organic layers were washed with saturated brine (40 mL), dried over anhydrous sodium sulfate, and filtered. The filtrate was concentrated in vacuo to remove solvent and give a yellow solid (35.4 mg, 16.7%).

MS (ESI, neg.ion) m/z: 408.3 (M−1);
$^1$H NMR (400 MHz, DMF-d$_7$) δ (ppm): 10.99 (s, 1H), 10.68 (s, 1H), 8.76 (d, J=2.1 Hz, 1H), 8.26 (d, J=9.3 Hz, 1H), 7.81 (d, J=9.1 Hz, 1H), 7.62 (d, J=7.3 Hz, 2H), 7.54 (t, J=7.5 Hz, 2H), 7.45 (t, J=7.2 Hz, 1H), 4.47 (d, J=5.5 Hz, 2H), 3.96 (s, 2H), 3.87 (s, 3H).

Example 4: 2-(4-hydroxy-1-methyl-2-oxo-7-(4-(3-oxomorpholino)phenoxy)-1,2-dihydroquinoline-3-carboxamido)acetic acid

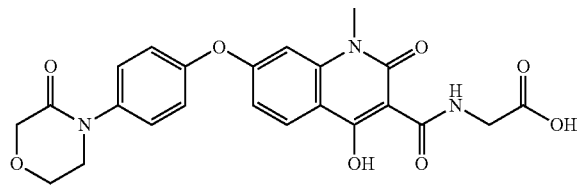 [SMILES: Cn1c(=O)c(C(=O)NCC(=O)O)c(O)c2ccc(Oc3ccc(N4CCOCC4=O)cc3)cc21]

Step 1: 1-(benzyloxy)-4-bromobenzene

4-Bromophenol (3.55 g, 20.5 mmol) was dissolved in acetonitrile (40 mL), then to the stirred solution were added potassium carbonate (3.86 g, 27.9 mmol) and benzyl bromide (2.4 mL, 20.0 mmol) in turn. The mixture was stirred at room temperature for 6 h under nitrogen protection, then filtered. The filtrate was concentrated in vacuo to give a yellow solid (5.14 g, 95.2%).

$^1$H NMR (400 MHz, CDCl$_3$) δ (ppm): 7.49-7.30 (m, 7H), 6.93-6.84 (m, 2H), 5.06 (s, 2H).

Step 2: 4-(4-(benzyloxy)phenyl)morpholin-3-one

To a round-bottom flask were added 1-(benzyloxy)-4-bromobenzene (2.00 g, 7.60 mmol), morpholin-3-one (1.15 g, 11.37 mmol), cuprous iodide (290 mg, 1.52 mmol), N,N'-dimethylethanediamine (0.4 mL, 4.00 mmol), potassium carbonate (2.11 g, 15.3 mmol) and toluene (20 mL) in turn. The mixture was stirred at 110° C. for 20 h. The mixture was cooled to room temperature and quenched with saturated aqueous ammonium chloride (20 mL). The resulting mixture was extracted with ethyl acetate (50 mL×3). The combined organic layers were washed with saturated brine (50 mL), dried over anhydrous sodium sulfate and filtered. The filtrate was concentrated in vacuo to remove the solvent. The residue was purified by column chromatography (petroleum ether/ethyl acetate (v/v)=1/2) to give a white solid (1.81 g, 84.0%).

$^1$H NMR (400 MHz, CDCl$_3$) δ (ppm): 7.47-7.32 (m, 5H), 7.27-7.22 (m, 2H), 7.06-7.00 (m, 2H), 5.09 (s, 2H), 4.35 (s, 2H), 4.06-4.02 (m, 2H), 3.76-3.71 (m, 2H).

Step 3: 4-(4-hydroxyphenyl)morpholin-3-one

To a solution of 4-(4-(benzyloxy)phenyl)morpholin-3-one (1.81 g, 6.39 mmol) in methanol (50 mL) was added 10% Pd/C (200 mg). The mixture was stirred at room temperature overnight in hydrogen atmosphere, then filtered by suction. The filtrate was concentrated in vacuo to remove the solvent and give a white solid (1.20 g, 97.0%).

MS (ESI, pos.ion) m/z: 194.1 (M+1).

Step 4: methyl 4-hydroxy-1-methyl-2-oxo-7-(4-(3-oxomorpholino)phenoxy)-1,2-dihydroquinoline-3-carboxylate To a microwave tube were added methyl 7-bromo-4-hydroxy-1-methyl-2-oxo-1,2-dihydroquinoline-3-carboxylate (350 mg, 1.12 mmol), 4-(4-hydroxyphenyl)morpholin-3-one (260 mg, 1.35 mmol), cuprous iodide (43 mg, 0.226 mmol), cesium carbonate (914 mg, 2.81 mmol), N,N-dimethylformamide (6 mL) and (1R,2R)—N$^1$,N$^2$-dimethyl-1,2-cyclohexanediamine (72 μL, 0.45 mmol) in turn. The mixture was stirred at 220° C. for 30 min under microwave irradiation and under nitrogen protection. The reaction mixture was cooled to room temperature and quenched with water (10 mL). The resulting mixture was acidified with diluted hydrochloric acid (2 M) to pH 3, and the mixture was extracted with ethyl acetate (20 mL). The organic layer was washed with water (10 mL) and saturated brine (20 mL) in turn, dried over anhydrous sodium sulfate. and filtered. The filtrate was concentrated in vacuo to give a yellow solid (263 mg, 55.3%).

MS (ESI, pos.ion) m/z: 424.9 (M+1).

Step 5: 2-(4-hydroxy-1-methyl-2-oxo-7-(4-(3-oxomorpholino)phenoxy)-1,2-dihydroquinoline-3-carboxamido)acetic acid Methyl 4-hydroxy-1-methyl-2-oxo-7-(4-(3-oxomorpholino)phenoxy)-1,2-dihydroquinoline-3-carboxylate (263 mg, 0.62 mmol) in ethylene glycol monomethyl ether (20 mL) was added sodium glycinate (120 mg, 1.24 mmol). The mixture was stirred at 130° C. for 2 h under nitrogen protection. The mixture was cooled to room temperature and concentrated in vacuo to remove the solvent. The residue was acidified with hydrochloric acid (1 M) to pH 1, and the resulting mixture was extracted with ethyl acetate (30 mL×2). The combined organic layers were washed with saturated brine (20 mL), dried over anhydrous sodium sulfate and filtered. The filtrate was concentrated in vacuo to remove the solvent and give a yellow solid (35 mg, 12.1%).

MS (ESI, neg.ion): m/z: 466.1 (M−1);

$^1$H NMR (400 MHz, DMF-d$_7$) δ (ppm): 10.68 (s, 1H), 8.18 (d, J=8.8 Hz, 1H), 7.60 (d, J=8.1 Hz, 2H), 7.29 (M, 3H), 7.02 (d, J=8.3 Hz, 1H), 4.31 (d, J=5.2 Hz, 2H), 4.28 (s, 2H), 4.13-4.06 (m, 2H), 3.91-3.84 (m, 2H), 3.67 (s, 3H).

Example 5: 2-(4-hydroxy-1-methyl-2-oxo-6-phenoxy-1,2-dihydroquinoline-3-carboxamido)acetic acid

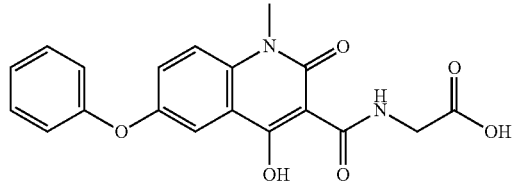 [SMILES: Cn1c(=O)c(C(=O)NCC(=O)O)c(O)c2cc(Oc3ccccc3)ccc21]

Step 1: methyl 4-hydroxy-1-methyl-2-oxo-6-phenoxy-1,2-dihydroquinoline-3-carboxylate To a microwave tube were added methyl 6-bromo-4-hydroxy-1-methyl-2-oxo-1,2-dihydroquinoline-3-carboxylate (250 mg, 0.801 mmol), phenol (91 mg, 0.967 mmol), cuprous iodide (31 mg, 0.163 mmol), cesium carbonate (653 mg, 2.00 mmol), N,N-dimethylformamide (5 mL) and (1R, 2R)—N$^1$,N$^2$-dimethyl-1,2-cyclohexanediamine (51 μL, 0.32 mmol) in turn. The mixture was stirred at 220° C. for 15 min under microwave irradiation and under nitrogen protection. The mixture was cooled to room temperature and quenched with water (10 mL). The mixture was acidified with diluted hydrochloric acid (2 M) to pH 3, and the resulting mixture was extracted with ethyl acetate (20 mL×2). The combined organic layers were washed successively with water (10 mL) and saturated brine (20 mL), dried over anhydrous sodium sulfate, filtered and concentrated in vacuo. The residue was purified by column chromatography (petrol ether/ethyl acetate (v/v)=2/3) to give a yellow solid (97 mg, 37.23%).

MS (ESI, pos.ion) m/z: 326.0 (M+1).

Step 2: 2-(4-hydroxy-1-methyl-2-oxo-6-phenoxy-1,2-dihydroquinoline-3-carboxamido)acetic acid methyl 4-hydroxy-1-methyl-2-oxo-6-phenoxy-1,2-dihydroquinoline-3-carboxylate (97 mg, 0.298 mmol) was dissolved in ethylene glycol monomethyl ether (15 mL), then to the solution was added sodium glycinate (60 mg, 0.618 mmol). The mixture was stirred at 130° C. for 2 h under nitrogen protection. The mixture was cooled to room temperature and concentrated in vacuo to remove the solvent. The residue was acidified with hydrochloric acid (1 M) to pH 1, and the resulting mixture was extracted with ethyl acetate (15 mL×2). The combined organic layers were washed with saturated brine (20 mL), dried over anhydrous sodium sulfate and filtered. The filtrate was concentrated in vacuo to give a light yellow solid (36.2 mg, 33.0%).

MS (ESI, neg.ion) m/z: 367.1 (M−1);

$^1$H NMR (400 MHz, DMSO-d$_6$) δ (ppm): 12.92 (s, 1H), 10.59 (s, 1H), 7.69 (d, J=9.1 Hz, 1H), 7.60-7.48 (m, 2H), 7.44 (t, J=7.7 Hz, 2H), 7.20 (t, J=7.3 Hz, 1H), 7.09 (d, J=7.9 Hz, 2H), 4.13 (d, J=5.4 Hz, 2H), 3.65 (s, 3H).

Example 6: 2-(6-benzamido-4-hydroxy-1-methyl-2-oxo-1,2-dihydroquinoline-3-carboxamido)acetic acid

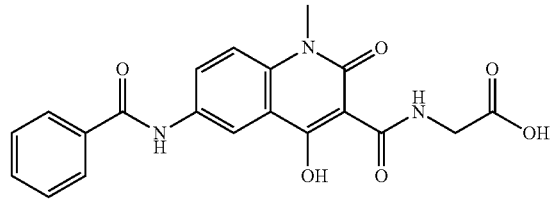 [SMILES: Cn1c(=O)c(C(=O)NCC(=O)O)c(O)c2cc(NC(=O)c3ccccc3)ccc21]

Step 1: methyl 6-benzamido-4-hydroxy-1-methyl-2-oxo-1,2-dihydroquinoline-3-carboxylate To a microwave tube were added methyl 6-bromo-4-hydroxy-1-methyl-2-oxo-1,2-dihydroquinoline-3-carboxylate (300 mg, 0.961 mmol), benzamide (140 mg, 1.16 mmol), cuprous iodide (37 mg, 0.194 mmol), cesium carbonate (783 mg, 2.40 mmol), N,N-dimethylformamide (5 mL) and (1R,2R)—$N^1$,$N^2$-dimethyl-1,2-cyclohexanediamine (61 µL, 0.38 mmol) in turn. The mixture was stirred at 220° C. for 15 min under microwave irradiation and under nitrogen protection. The mixture was cooled to room temperature and quenched with water (10 mL). The mixture was acidified with diluted hydrochloric acid (2 M) to pH 3, and the resulting mixture was extracted with ethyl acetate (20 mL×2). The combined organic layers were washed with water (10 mL) and saturated brine (20 mL), dried over anhydrous sodium sulfate, and filtered. The filtrate was concentrated in vacuo to give a yellow solid (178 mg, 52.57%).

MS (ESI, pos.ion) m/z: 353.0 (M+1).

Step 2: 2-(6-benzamido-4-hydroxy-1-methyl-2-oxo-1,2-dihydroquinoline-3-carboxamido)acetic acid Methyl 6-benzamido-4-hydroxy-1-methyl-2-oxo-1,2-dihydroquinoline-3-carboxylate (178 mg, 0.505 mmol) was dissolved in ethylene glycol monomethyl ether (15 mL), then to the solution was added sodium glycinate (99 mg, 1.02 mmol). The mixture was stirred at 130° C. for 2 h under nitrogen protection. The mixture was cooled to room temperature and concentrated in vacuo to remove the solvent. The residue was acidified with hydrochloric acid (1 M) to pH 1, and the resulting mixture was extracted with ethyl acetate (15 mL×2). The combined organic layers were washed with saturated brine (20 mL), dried over anhydrous sodium sulfate and filtered. The filtrate was concentrated in vacuo to give a light yellow solid (66 mg, 33.04%).

MS (ESI, neg.ion) m/z: 394.2 (M−1);

$^1$H NMR (400 MHz, DMF-$d_7$) δ (ppm): 10.84 (s, 1H), 10.59 (s, 1H), 8.80 (d, J=1.2 Hz, 1H), 8.36 (d, J=8.2 Hz, 1H), 8.14 (d, J=7.3 Hz, 2H), 7.65 (ddd, J=23.9, 19.3, 8.1 Hz, 4H), 4.32 (d, J=4.9 Hz, 2H), 3.75 (s, 3H).

Example 7: 2-(6-((1H-indol-1-yl)sulfonyl)-4-hydroxy-1-methyl-2-oxo-1,2-dihydroquinoline-3-carboxamido)acetic acid

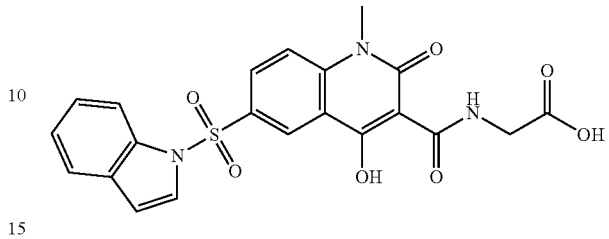

Step 1: 1-methyl-1H-benzo[d][1,3]oxazine-2,4-dione

To a three-neck round-bottom flask were added sodium hydride (885 mg, 22.13 mmol) and N,N-dimethylformamide (40 mL) in turn under nitrogen protection. The mixture was cooled to 0° C., and then 1H-benzo[d][1,3]oxazine-2,4-dione (3.00 g, 18.39 mmol) was added. The resulting mixture was stirred at room temperature for 1 h, then iodomethane (1.26 mL, 20.2 mmol) was added dropwise, and the mixture was stirred for 16 h at room temperature. The reaction mixture was poured into ice-water (50 mL), then the resulting mixture was filtered. The filter cake was washed with water and ethyl ether in turn, and dried in oven to give a brown solid (1.21 g, 37.1%).

MS (ESI, pos.ion) m/z: 178.1 (M+1).

Step 2: methyl 4-hydroxy-1-methyl-2-oxo-1,2-dihydroquinoline-3-carboxylate

To a stirred solution of 1-methyl-1H-benzo[d][1,3]oxazine-2,4-dione (2.00 g, 11.29 mmol) in N,N-dimethylformamide (15 mL) was added a solution of sodium tert-butoxide (2.17 g, 22.6 mmol) and dimethyl malonate (2.6 mL, 23.0 mmol) in N,N-dimethylformamide (10 mL). The mixture was stirred at 100° C. for 2 h under nitrogen protection. The mixture was cooled to room temperature and concentrated in vacuo to remove the solvent. The residue was acidified with diluted hydrochloric acid to pH 5, and the resulting mixture was extracted with dichloromethane (20 mL×2). The combined organic layers were washed with saturated brine (20 mL), dried over anhydrous sodium sulfate, filtered and concentrated in vacuo. The residue was purified by column chromatography (EtOAc/PE (v/v)=3/2) to give a light yellow solid (1.20 g, 46.0%).

MS (ESI, pos.ion) m/z: 234.1 (M+1).

Step 3: methyl 6-(chlorosulfonyl)-4-hydroxy-1-methyl-2-oxo-1,2-dihydroquinoline-3-carboxylate To a round-bottom flask were added methyl 4-hydroxy-1-methyl-2-oxo-1,2-dihydroquinoline-3-carboxylate (500 mg, 2.14 mmol) and chlorosulfonic acid (10 mL, 148.9 mmol). The mixture was stirred at 60° C. overnight under nitrogen protection. The mixture was cooled to rt, and thionyl chloride (15 mL, 205 mmol) was added. The resulting mixture was stirred at room temperature for 24 h. After the reaction was complete, the reaction mixture was poured into ice-water (10 g). The resulting mixture was extracted with EtOAc (50 mL×2). The combined organic layers were washed successively with water (20 mL) and saturated brine (30 mL), dried over anhydrous sodium sulfate, and filtered. The filtrate was concentrated in vacuo to give a brown solid (436 mg, 61.31%).

MS (ESI, pos.ion) m/z: 331.9 (M+1);

Step 4: methyl 6-((1H-indol-1-yl)sulfonyl)-4-hydroxy-1-methyl-2-oxo-1,2-dihydroquinoline-3-carboxylate To a solution of 1H-indole (137 mg, 1.17 mmol) in toluene (10 mL) were added tetrabutylammonium hydrogen sulfate (34 mg, 0.10 mmol), 50% aqueous potassium hydroxide solution (6 mL) and a solution of methyl 6-(chlorosulfonyl)-4-hydroxy-1-methyl-2-oxo-1,2-dihydroquinoline-3-carboxylate (316 mg, 0.953 mmol) in toluene (10 mL) in turn. The mixture was stirred at room temperature for 4 h, then quenched with water (20 mL). The resulting mixture was extracted with ethyl acetate (30 mL×3). The combined organic lays were washed successively with water (50 mL×2) and saturated brine (50 mL), dried over anhydrous sodium sulfate, and filtered. The filtrate was concentrated in vacuo to give a light red solid (130 mg, 33.1%).

MS (ESI, pos.ion) m/z: 413.1 (M+1).

Step 5: 2-(6-((1H-indol-1-yl)sulfonyl)-4-hydroxy-1-methyl-2-oxo-1,2-dihydroquinoline-3-carboxamido) acetic acid Methyl 6-((1H-indol-1-yl)sulfonyl)-4-hydroxy-1-methyl-2-oxo-1,2-dihydroquinoline-3-carboxylate (130 mg, 0.315 mmol) was dissolved in ethylene glycol monomethyl ether (20 mL), then to the solution was added sodium glycinate (92 mg, 0.948 mmol). The mixture was stirred at 130° C. for 2 h under nitrogen protection. The mixture was cooled to room temperature and concentrated in vacuo to remove the solvent. The residue was acidified with hydrochloric acid (1 M) to pH 1, and the resulting mixture was extracted with ethyl acetate (15 mL×2). The combined organic layers were washed with saturated brine (20 mL), dried over anhydrous sodium sulfate and filtered. The filtrate was concentrated in vacuo to give a yellow solid (80 mg, 55.7%).

MS (ESI, neg.ion) m/z: 454.2 (M−1);

$^1$H NMR (400 MHz, DMSO-$d_6$) δ (ppm): 10.31 (t, J=5.1 Hz, 1H), 8.51 (d, J=1.8 Hz, 1H), 8.23 (dd, J=9.1, 2.3 Hz, 1H), 7.98 (d, J=8.3 Hz, 1H), 7.89 (d, J=3.7 Hz, 1H), 7.72 (d, J=9.2 Hz, 1H), 7.60 (d, J=7.8 Hz, 1H), 7.37 (t, J=7.8 Hz, 1H), 7.25 (t, J=7.5 Hz, 1H), 6.87 (d, J=3.2 Hz, 1H), 4.13 (d, J=5.5 Hz, 2H), 3.56 (s, 3H).

Example 8: 2-(4-hydroxy-1-methyl-7-(naphthalen-2-yloxy)-2-oxo-1,2-dihydroquinoline-3-carboxamido) acetic acid

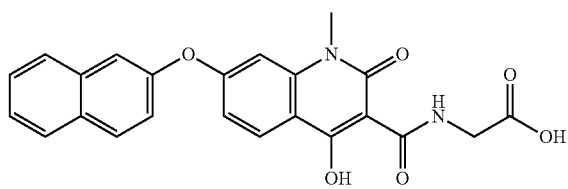 [SMILES: Cn1c(=O)c(C(=O)NCC(=O)O)c(O)c2ccc(Oc3ccc4ccccc4c3)cc21]

Step 1: methyl 4-hydroxy-1-methyl-7-(naphthalen-2-yloxy)-2-oxo-1,2-dihydroquinoline-3-carboxylate To a two-neck round-bottom flask were added methyl 7-bromo-4-hydroxy-1-methyl-2-oxo-1,2-dihydroquinoline-3-carboxylate (1.00 g, 3.20 mmol), 2-naphthol (0.55 g, 3.80 mmol), cesium carbonate (2.60 g, 8.00 mmol), cuprous iodide (0.12 g, 0.63 mmol), (1R,2R)—$N^1$,$N^2$-dimethyl-1,2-cyclohexanediamine (182 µL, 1.15 mmol) and N,N-dimethylformamide (20 mL) in turn under nitrogen protection. The mixture was stirred at 150° C. for 6 h. The mixture was cooled to room temperature and concentrated in vacuo to remove the solvent. The residue was acidified with diluted hydrochloric acid (2 M) to pH 3, and the resulting mixture was extracted with ethyl acetate (30 mL×3). The combined organic layers were washed with water (20 mL×2) and saturated brine (40 mL), dried over anhydrous sodium sulfate, filtered, and the filtrate was concentrated in vacuo. The residue was purified by column chromatography (petroleum ether/ethyl acetate (v/v)=1/1) to give a yellow solid (180 mg, 15.0%).

MS (ESI, pos.ion) m/z: 376.9 (M+1).

Step 2: 2-(4-hydroxy-1-methyl-7-(naphthalen-2-yloxy)-2-oxo-1,2-dihydroquinoline-3-carboxamido) acetic acid Methyl 4-hydroxy-1-methyl-7-(naphthalen-2-yloxy)-2-oxo-1,2-dihydroquinoline-3-carboxylate (200 mg, 0.533 mmol) was dissolved in ethylene glycol monomethyl ether (10 mL), then to the solution was added sodium glycinate (100 mg, 1.03 mmol). The mixture was stirred at 130° C. for 2 h under nitrogen protection. The mixture was cooled to room temperature and concentrated in vacuo to remove the solvent. The residue was acidified with hydrochloric acid (1 M) to pH 1, and the resulting mixture was extracted with ethyl acetate (20 mL×2). The combined organic layers were washed with saturated brine (20 mL), dried over anhydrous sodium sulfate and filtered. The filtrate was concentrated in vacuo to give a yellow solid (200 mg, 89.7%).

MS (ESI, pos.ion) m/z: 419.8 (M+1);

$^1$H NMR (400 MHz, DMSO-$d_6$) δ (ppm): 10.47 (s, 1H), 8.07 (dd, J=15.9, 8.8 Hz, 2H), 7.98 (d, J=7.7 Hz, 1H), 7.91 (d, J=7.6 Hz, 1H), 7.67 (s, 1H), 7.53 (t, J=7.8 Hz, 2H), 7.40 (d, J=8.8 Hz, 1H), 7.27 (s, 1H), 6.97 (d, J=8.8 Hz, 1H), 4.13 (d, J=2.9 Hz, 2H), 3.55 (s, 3H).

Example 9: 2-(4-hydroxy-1-methyl-6-(naphthalen-2-yloxy)-2-oxo-1,2-dihydroquinoline-3-carboxamido) acetic acid

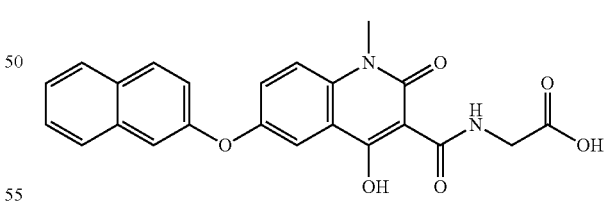

Step 1: methyl 4-hydroxy-1-methyl-6-(naphthalen-2-yloxy)-2-oxo-1,2-dihydroquinoline-3-carboxylate To a two-neck round-bottom flask were added methyl 6-bromo-4-hydroxy-1-methyl-2-oxo-1,2-dihydroquinoline-3-carboxylate (1.50 g, 4.80 mmol), 2-naphthol (0.83 g, 5.80 mmol), cesium carbonate (3.90 g, 12.0 mmol), cuprous iodide (0.18 g, 0.95 mmol), (1R,2R)—$N^1$,$N^2$-dimethyl-1,2-cyclohexanediamine (300 µL, 1.90 mmol) and N,N-dimethylformamide (30 mL) in turn under nitrogen protection. The mixture was stirred at 150° C. for 5 h. The mixture was cooled to room temperature and concentrated in vacuo to remove the solvent. The residue was acidified with diluted hydrochloric acid (2 M) to pH 3, and the resulting mixture was extracted with ethyl acetate (40 mL×3). The combined organic layers were washed with water (20 mL×2) and saturated brine (40 mL), dried over anhydrous sodium sulfate, filtered and concentrated in vacuo. The residue was purified by column chromatography (petroleum ether/ethyl acetate (v/v)=1/1) to give a yellow solid (200 mg, 11.0%).

MS (ESI, pos.ion) m/z: 377.2 (M+1).

Step 2: 2-(4-hydroxy-1-methyl-6-(naphthalen-2-yloxy)-2-oxo-1,2-dihydroquinoline-3-carboxamido) acetic acid Methyl 4-hydroxy-1-methyl-6-(naphthalen-2-yloxy)-2-oxo-1,2-dihydroquinoline-3-carboxylate (200 mg, 0.533 mmol) was dissolved in ethylene glycol monomethyl ether (10 mL), then to the solution was added sodium glycinate (103 mg, 1.06 mmol). The mixture was stirred at 130° C. for 2 h under nitrogen protection. The mixture was cooled to room temperature and concentrated in vacuo to remove the solvent. The residue was acidified with hydrochloric acid (1 M) to pH 1, and the resulting mixture was extracted with ethyl acetate (20 mL×2). The combined organic layers were washed successively with water (10 mL) and saturated brine (20 mL), dried over anhydrous sodium sulfate and filtered. The filtrate was concentrated in vacuo to give a yellow solid (90 mg, 40.4%).

MS (ESI, pos.ion) m/z: 419.15 (M+1);

$^1$H NMR (400 MHz, DMSO-d$_6$) δ (ppm): 10.59 (t, J=5.4 Hz, 1H), 8.01 (d, J=8.9 Hz, 1H), 7.94 (d, J=7.9 Hz, 1H), 7.84 (d, J=7.9 Hz, 1H), 7.72 (d, J=9.2 Hz, 1H), 7.65 (dd, J=9.2, 2.7 Hz, 1H), 7.60 (d, J=2.6 Hz, 1H), 7.54-7.43 (m, 3H), 7.36 (dd, J=8.9, 2.4 Hz, 1H), 4.13 (d, J=5.5 Hz, 2H), 3.67 (s, 3H).

Example 10: 2-(6-(benzhydrylcarbamoyl)-4-hydroxy-1-methyl-2-oxo-1,2-dihydroquinoline-3-carboxamido)acetic acid

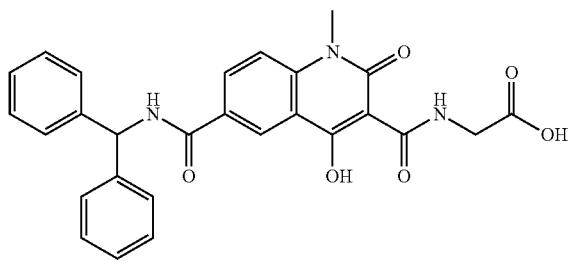 [SMILES: Cn1c(=O)c(C(=O)NCC(=O)O)c(O)c2cc(C(=O)NC(c3ccccc3)c3ccccc3)ccc21]

Step 1: 4-nitroisophthalic acid

To a solution of 2,4-dimethylnitrobenzene (15.0 g, 99.2 mmol) in water (500 mL) was added slowly potassium permanganate (78.5 g, 497 mmol). The mixture was stirred at 100° C. for 30 h. The mixture was cooled to room temperature and filtered through a celite pad. The filtrate was acidified with diluted hydrochloric acid (2 M) to pH 4, and there was a solid precipitated out, then the mixture was filtered. The filter cake was washed with water and dried in vacuo to give a white solid (11.2 g, 53.5%).

MS (ESI, neg.ion) m/z: 421.1 (2M-1).

Step 2: dimethyl 4-nitroisophthalate

To a solution of 4-nitroisophthalic acid (10.0 g, 47.4 mmol) in methanol (60 mL) was added dropwise slowly concentrated sulphuric acid (10 mL) at 0° C. After the addition, the mixture was stirred at 90° C. for 8 h. The reaction mixture was cooled to room temperature and poured into ice-water, and there was a solid precipitated out, then the mixture was filtered. The filter cake was washed with methanol and dried in vacuo to give a white solid (7.52 g, 66.4%).

MS (ESI, pos.ion) m/z: 240.0 (M+1).

Step 3: 3-(methoxycarbonyl)-4-nitrobenzoic acid

To a solution of dimethyl 4-nitroisophthalate (500 mg, 2.09 mmol) in methanol (20.0 mL) was added a solution of sodium hydroxide (130 mg, 3.25 mmol) in water (3 mL). The mixture was stirred at 25° C. for 30 min, then acidified with concentrated hydrochloric acid to pH 4. The reaction mixture was concentrated in vacuo to remove the solvent. The residue was purified by column chromatography (dichloromethane/methanol (v/v)=10/1) to give a white solid (410 mg, 87.1%).

MS (ESI, neg.ion) m/z: 223.90 (M−1).

Step 4: methyl 5-(benzhydrylcarbamoyl)-2-nitrobenzoate

The solution of 3-(methoxycarbonyl)-4-nitrobenzoic acid (3.00 g, 13.3 mmol) in thionyl chloride (10.0 mL) was stirred at 85° C. for 2 h. The solution was concentrated in vacuo to remove the solvent and the residue was dissolved in dichloromethane (30.0 mL). To the resulting mixture were added aminodiphenylmethane (2.40 g, 13.1 mmol) and triethylamine (4.00 mL, 30 mmol) in turn at 0° C., and the mixture was stirred at 25° C. for 4 h. To the mixture was added water (50 mL), and there was a solid precipitated out, then the mixture was filtered. The filter cake was washed with water and dried in vacuo to give a white solid (3.58 g, 68.8%).

MS (ESI, pos.ion) m/z: 390.90 (M+1).

Step 5: methyl 2-amino-5-(benzhydrylcarbamoyl)benzoate

To a solution of methyl 5-(benzhydrylcarbamoyl)-2-nitrobenzoate (3.58 g, 9.17 mmol) in ethanol (150 mL) was added 10% Pd/C (0.97 g). The mixture was stirred at room temperature for 24 h in a hydrogen atmosphere. The reaction mixture was filtered through a celite pad, and the filtrate was concentrated. The residue was purified by column chromatography (petroleum ether/ethyl acetate (v/v)=3/1) to give a white solid (2.01 g, 61.0%).

MS (ESI, pos.ion) m/z: 361.25 (M+1);

$^1$H NMR (400 MHz, DMSO-d$_6$) δ (ppm): 9.03 (d, J=8.8 Hz, 1H), 8.37 (d, J=2.1 Hz, 1H), 7.87 (dd, J=8.8, 2.1 Hz, 1H), 7.34 (d, J=4.3 Hz, 8H), 7.29-7.23 (m, 2H), 7.07 (s, 2H), 6.80 (d, J=8.8 Hz, 1H), 6.39 (d, J=8.7 Hz, 1H), 3.82 (s, 3H).

Step 6: 2-amino-5-(benzhydrylcarbamoyl)benzoic acid

To a solution of methyl 2-amino-5-(benzhydrylcarbamoyl)benzoate (2.00 g, 5.50 mmol) in methanol (100 mL) was added a solution of sodium hydroxide (0.890 g, 22.3 mmol) in water (5 mL). The mixture was stirred at 80° C. for 4 h. The mixture was cooled to room temperature and acidified with diluted hydrochloric acid (2 M) to pH 4, then the mixture was concentrated in vacuo to remove some of the solvent. The residue was filtered. The filter cake was washed with water and dried in vacuo to give a white solid (1.72 g, 89.0%).

MS (ESI, pos.ion) m/z: 346.95 (M+1).

Step 7: N-benzhydryl-2,4-dioxo-2,4-dihydro-1H-benzo[d][1,3]oxazine-6-carboxamide To a solution of 2-amino-5-(benzhydrylcarbamoyl)benzoic acid (1.16 g, 3.35 mmol) in tetrahydrofuran (40 mL) was added triphosgene (0.497 g, 1.67 mmol). The mixture was stirred at 70° C. for 24 h. The mixture was cooled to room temperature and quenched with water (40 mL). The resulting mixture was extracted with ethyl acetate (20 mL×2). The combined organic layers were washed successively with water (30 mL) and saturated brine (20 mL), dried over anhydrous sodium sulfate and filtered. The filtrate was concentrated in vacuo to give a yellow solid (1.19 g, 95.4%).

MS (ESI, pos.ion) m/z: 373.20 (M+1).

Step 8: methyl 5-(benzhydrylcarbamoyl)-2-(dimethylamino)benzoate

To a three-neck round-bottom flask were added potassium carbonate (0.290 g, 2.10 mmol) and N,N-dimethylformamide (5.00 mL) in turn. The mixture was cooled to 0° C., and N-benzhydryl-2,4-dioxo-2,4-dihydro-1H-benzo[d][1,3]oxazine-6-carboxamide (100 mg, 0.269 mmol) was added. The resulting mixture was stirred at room temperature for 1 h, then iodomethane (20.0 μL, 0.321 mmol) was added, and the mixture was stirred for further 24 h. To the mixture was added water (20 mL), and there was a solid precipitated out, then the mixture was filtered. The filter cake was washed with water and dried in vacuo to give a white solid (40.0 mg, 39.8%).

MS (ESI, pos.ion) m/z: 374.95 (M+1);
$^1$H NMR (600 MHz, DMSO-$d_6$) δ (ppm): 9.09 (d, J=8.8 Hz, 1H), 8.46 (d, J=2.1 Hz, 1H), 8.05 (dd, J=8.9, 2.0 Hz, 1H), 7.90 (d, J=4.9 Hz, 1H), 7.35 (d, J=4.3 Hz, 8H), 7.27 (dd, J=8.3, 4.5 Hz, 2H), 6.77 (d, J=9.0 Hz, 1H), 6.41 (d, J=8.8 Hz, 1H), 3.83 (s, 3H), 2.91 (d, J=5.0 Hz, 3H).

Step 9: 5-(benzhydrylcarbamoyl)-2-(dimethylamino)benzoic acid

To a solution of methyl 5-(benzhydrylcarbamoyl)-2-(dimethylamino)benzoate (40.0 mg, 0.107 mmol) in methanol (10 mL) was added a solution of lithium hydroxide (100 mg, 4.18 mmol) in water (1 mL). The mixture was stirred at 70° C. for 2 h. The mixture was cooled to room temperature and acidified with diluted hydrochloric acid (2 M) to pH 4, and there was a solid precipitated out, then the mixture was filtered. The filter cake was washed with water and dried in vacuo to give a yellow solid (35.0 mg, 90.9%).

MS (ESI, pos.ion) m/z: 361.25 (M+1).

Step 10: N-benzhydryl-1-methyl-2,4-dioxo-2,4-dihydro-1H-benzo[d][1,3]oxazine-6-carboxamide To a solution of 5-(benzhydrylcarbamoyl)-2-(dimethylamino)benzoic acid (0.720 g, 1.98 mmol) in tetrahydrofuran (30 mL) was added triphosgene (0.420 g, 1.40 mmol). The mixture was stirred at 75° C. for 10 h. The reaction mixture was cooled to room temperature and poured into ice-water, and there was a solid precipitated out, then the mixture was filtered. The filter cake was washed with methanol and dried in vacuo to give a white solid (0.720 g, 93.5%).

MS (ESI, pos.ion) m/z: 386.9 (M+1).

Step 11: methyl 6-(benzhydrylcarbamoyl)-4-hydroxy-1-methyl-2-oxo-1,2-dihydroquinoline-3-carboxylate To a solution of N-benzhydryl-1-methyl-2,4-dioxo-2,4-dihydro-1H-benzo[d][1,3]oxazine-6-carboxamide (386 mg, 0.999 mmol) in N,N-dimethylformamide (5 mL) were added sodium tert-butoxide (192 mg, 2.00 mmol) and a solution of dimethyl malonate (230 μL, 2.01 mmol) in N,N-dimethylformamide (4 mL). The mixture was stirred at 100° C. for 3 h. The reaction mixture was acidified with diluted hydrochloric acid (2 M) to pH 4, and the mixture was extracted with ethyl acetate (50 mL×2). The combined organic layers were washed with water (20 mL×2) and saturated brine (30 mL), dried over anhydrous sodium sulfate and filtered. The filtrate was concentrated in vacuo to give a white solid (320 mg, 72.39%).

MS (ESI, pos.ion) m/z: 443.25 (M+1).

Step 12: 2-(6-(benzhydrylcarbamoyl)-4-hydroxy-1-methyl-2-oxo-1,2-dihydroquinoline-3-carboxamido) acetic acid A mixture of methyl 6-(benzhydrylcarbamoyl)-4-hydroxy-1-methyl-2-oxo-1,2-dihydroquinoline-3-carboxylate (300 mg, 0.678 mmol) and sodium glycinate (0.197 g, 2.03 mmol) in ethylene glycol monomethyl ether (15 mL) was refluxed for 3 h. The mixture was cooled to room temperature and filtered. The filter cake was dissolved in water (10 mL), and the mixture was acidified with diluted hydrochloric acid (2 M) to pH 4, then the resulting mixture was filtered. The filter cake was washed with water and dried in vacuo to give a white solid (150 mg, 45.6%).

MS (ESI, pos.ion) m/z: 485.8 (M+1);
$^1$H NMR (400 MHz, DMSO-$d_6$) δ (ppm): 10.50 (d, J=5.4 Hz, 1H), 9.58 (d, J=8.7 Hz, 1H), 8.73 (d, J=1.7 Hz, 1H), 8.34 (dd, J=8.9, 1.9 Hz, 1H), 7.71 (d, J=9.0 Hz, 1H), 7.42-7.33 (m, 8H), 7.28 (t, J=6.4 Hz, 2H), 6.46 (d, J=8.6 Hz, 1H), 4.15 (d, J=5.5 Hz, 2H), 3.67 (s, 3H).

Example 11: 2-(6-(benzhydryl(methyl)carbamoyl)-4-hydroxy-1-methyl-2-oxo-1,2-dihydroquinoline-3-carboxamido)acetic acid

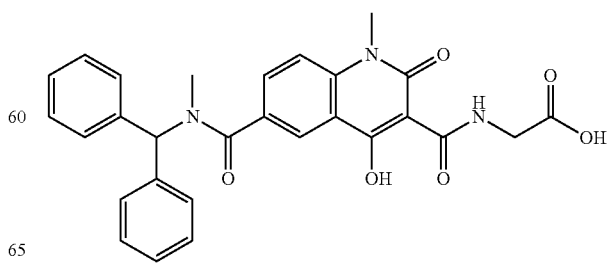

Step 1: methyl 6-(benzhydryl(methyl)carbamoyl)-4-hydroxy-1-methyl-2-oxo-1,2-dihydroquinoline-3-carboxylate To a two-neck flask were added methyl 6-(benzhydryl-carbamoyl)-4-hydroxy-1-methyl-2-oxo-1,2-dihydroquinoline-3-carboxylate (350 mg, 0.791 mmol), N,N-dimethylformamide (10 mL) and sodium hydride (75 mg, 3.1 mmol). The mixture was stirred at room temperature for 1 h, and then iodomethane (100 μL, 1.61 mmol) was added. After the addition, the mixture was stirred for 24 h at room temperature. The reaction mixture was quenched with water (10 mL), and there was a white solid precipitated out, then the mixture was filtered. The filter cake was dried in vacuo to give a white solid (210 mg, 58.2%).

MS (ESI, pos.ion) m/z: 457.3 (M+1).

Step 2: 2-(6-(benzhydryl(methyl)carbamoyl)-4-hydroxy-1-methyl-2-oxo-1,2-dihydroquinoline-3-carboxamido)acetic acid To a single-neck flask were added methyl 6-(benzhydryl(methyl)carbamoyl)-4-hydroxy-1-methyl-2-oxo-1,2-dihydroquinoline-3-carboxylate (200 mg, 0.438 mmol), sodium glycinate (130 mg, 1.34 mmol) and ethylene glycol monomethyl ether (10 mL). The mixture was stirred at 130° C. for 3 h under nitrogen protection. The mixture was cooled to room temperature and filtered by suction. The filter cake was dissolved in water (20 mL) and the mixture was acidified with diluted hydrocloric acid (2 M) to pH 4. The resulting mixture was filtered, and the filter cake was dried in vacuo to give a gray-white solid (130 mg, 59.4%).

MS (ESI, neg.ion) m/z: 498.25 (M−1);
$^1$H NMR (600 MHz, DMSO-$d_6$) δ (ppm): 10.49 (s, 1H), 8.08 (s, 1H), 7.87 (s, 1H), 7.69 (d, J=8.8 Hz, 1H), 7.40 (dt, J=38.7, 7.4 Hz, 6H), 7.21 (s, 5H), 4.14 (d, J=5.4 Hz, 2H), 3.65 (s, 3H), 2.76 (s, 3H).

Example 12: 2-(7-(3-chlorophenoxy)-4-hydroxy-1-methyl-2-oxo-1,2-dihydroquinoline-3-carboxamido) acetic acid

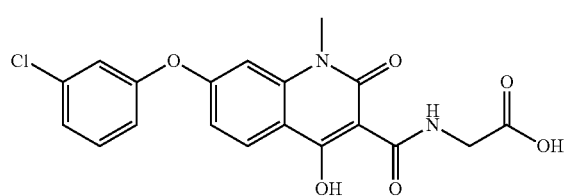 [SMILES: Cn1c(=O)c(C(=O)NCC(=O)O)c(O)c2ccc(Oc3cccc(Cl)c3)cc21]

Step 1: methyl 7-(3-chlorophenoxy)-4-hydroxy-1-methyl-2-oxo-1,2-dihydroquinoline-3-carboxylate To a two-neck flask were added methyl 7-bromo-4-hydroxy-1-methyl-2-oxo-1,2-dihydroquinoline-3-carboxylate (1.00 g, 3.20 mmol), 3-chlorophenol (0.536 g, 4.17 mmol), cuprous iodide (0.123 g, 0.646 mmol), N,N-dimethylglycine (0.100 g, 0.970 mmol), cesium carbonate (2.61 g, 8.01 mmol) and dimethyl sulfoxide (20 mL) in turn under nitrogen protection. The mixture was stirred at 140° C. for 20 hours. The mixture was cooled to room temperature and acidified with diluted hydrochloric acid (1 M) to pH 4, and the resulting mixture was extracted with ethyl acetate (50 mL×3). The combined organic layers were washed with water (30 mL×2) and saturated brine (30 mL), dried over anhydrous sodium sulfate. The reaction mixture was filtered and the filtrate was concentrated in vacuo to remove the solvent. The residue was purified by column chromatography (petroleum ether/ethyl acetate (v/v)=1/2) to give a white solid (70.99 g, 85.9%).

MS (ESI, pos.ion) m/z: 359.8 (M+1).

Step 2: 2-(7-(3-chlorophenoxy)-4-hydroxy-1-methyl-2-oxo-1,2-dihydroquinoline-3-carboxamido) acetic acid A mixture of methyl 7-(3-chlorophenoxy)-4-hydroxy-1-methyl-2-oxo-1,2-dihydroquinoline-3-carboxylate (0.99 g, 2.75 mmol) and sodium glycinate (0.534 g, 5.50 mmol) in ethylene glycol monomethyl ether (50 mL) was refluxed for 1 h. The mixture was cooled to room temperature and concentrated in vacuo to remove the solvent, and then water (20 mL) was added. The resulting mixture was acidified with diluted hydrochloric acid (1 M) to pH 3, and then filtered. The filter cake was washed with water and dried, which was recrystallized from (petroleum ether/ethyl acetate (v/v)=1/3) to give a white solid (0.750 g, 67.7%).

MS (ESI, pos.ion) m/z: 402.8 (M+1);
$^1$H NMR (400 MHz, DMSO-$d_6$) δ (ppm): 10.47 (s, 1H), 8.09 (d, J=8.8 Hz, 1H), 7.49 (t, J=8.1 Hz, 1H), 7.32 (d, J=8.0 Hz, 1H), 7.29 (d, J=2.0 Hz, 1H), 7.25 (d, J=1.9 Hz, 1H), 7.15 (dd, J=8.2, 2.0 Hz, 1H), 6.94 (dd, J=8.9, 2.0 Hz, 1H), 4.03 (d, J=5.3 Hz, 2H), 3.56 (s, 3H).

Example 13: 2-(7-(4-chlorophenoxy)-4-hydroxy-1-methyl-2-oxo-1,2-dihydroquinoline-3-carboxamido) acetic acid

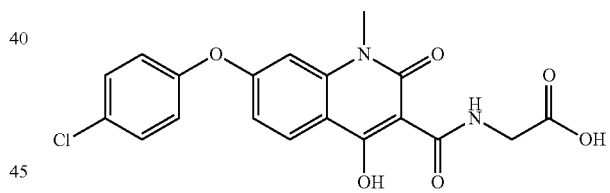

Step 1: methyl 7-(4-chlorophenoxy)-4-hydroxy-1-methyl-2-oxo-1,2-dihydroquinoline-3-carboxylate To a two-neck round-bottom flask were added methyl 7-bromo-4-hydroxy-1-methyl-2-oxo-1,2-dihydroquinoline-3-carboxylate (0.268 g, 2.08 mmol), 4-chlorophenol (0.268 g, 2.08 mmol), cuprous iodide (0.062 g, 0.33 mmol), N,N-dimethylglycine (0.050 g, 0.48 mmol), cesium carbonate (1.30 g, 3.99 mmol) and dimethyl sulfoxide (20 mL) in turn under nitrogen protection. The mixture was stirred at 140° C. for 18 h. The mixture was cooled to room temperature and acidified with diluted hydrochloric acid (1 M) to pH 4, and the resulting mixture was extracted with ethyl acetate (50 mL×3). The combined organic layers were washed successively with water (50 mL×2) and saturated brine (40 mL), dried over anhydrous sodium sulfate, and filtered. The filtrate was concentrated in vacuo. The residue was purified by column chromatography (petroleum ether/ethyl acetate (v/v)=1/2) to give a white solid (0.250 g, 43.4%).

Step 2: 2-(7-(4-chlorophenoxy)-4-hydroxy-1-methyl-2-oxo-1,2-dihydroquinoline-3-carboxamido)acetic acid A mixture of methyl 7-(4-chlorophenoxy)-4-hydroxy-1-methyl-2-oxo-1,2-dihydroquinoline-3-carboxylate (0.250 g, 0.695 mmol) and sodium glycinate (0.134 g, 1.38 mmol) in ethylene glycol monomethyl ether (10 mL) was refluxed for 2 h. The mixture was cooled to room temperature and concentrated in vacuo to remove the solvent, and then water (20 mL) was added. The resulting mixture was acidified with diluted hydrochloric acid (1 M) to pH 3, then filtered. The filter cake was washed with water and dried, which was recrystallized from (ethyl acetate/petroleum ethere (v/v)=1/3) to give a white solid (0.120 g, 42.9%).

MS (ESI, pos.ion) m/z: 403.2 (M+1);

$^1$H NMR (400 MHz, DMSO-$d_6$) δ (ppm): 10.48 (s, 1H), 8.08 (d, J=8.8 Hz, 1H), 7.52 (d, J=8.6 Hz, 2H), 7.31-7.07 (m, 3H), 6.91 (d, J=8.8 Hz, 1H), 3.89 (d, J=4.6 Hz, 2H), 3.54 (s, 3H).

Example 14: 2-(7-(2,3-difluorophenoxy)-4-hydroxy-1-methyl-2-oxo-1,2-dihydroquinoline-3-carboxamido)acetic acid

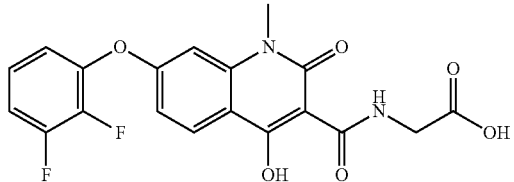 [SMILES: Cn1c(=O)c(C(=O)NCC(=O)O)c(O)c2ccc(Oc3cccc(F)c3F)cc21]

Step 1: methyl 7-(2,3-difluorophenoxy)-4-hydroxy-1-methyl-2-oxo-1,2-dihydroquinoline-3-carboxylate To a two-neck flask were added methyl 7-bromo-4-hydroxy-1-methyl-2-oxo-1,2-dihydroquinoline-3-carboxylate (500 mg, 1.60 mmol), 2,3-difluorophenol (271 mg, 2.08 mmol), cuprous iodide (61 mg, 0.320 mmol), N,N-dimethylglycine (50 mg, 0.485 mmol), cesium carbonate (1.30 g, 3.99 mmol) and dimethyl sulfoxide (20 mL) in turn under nitrogen protection. The mixture was stirred at 140° C. for 20 h. The mixture was cooled to room temperature and acidified with diluted hydrochloric acid (1 M) to pH 4, and the resulting mixture was extracted with ethyl acetate (20 mL×3). The combined organic layers were washed successively with water (30 mL×2) and saturated brine (30 mL), dried over anhydrous sodium sulfate, and filtered. The filtrate was concentrated in vacuo. The residue was purified by column chromatography (PE/EtOAc (v/v)=2/1) to give a white solid (310 mg, 53.6%).

MS (ESI, pos.ion) m/z: 361.9 (M+1).

Step 2: 2-(7-(2,3-difluorophenoxy)-4-hydroxy-1-methyl-2-oxo-1,2-dihydroquinoline-3-carboxamido)acetic acid A mixture of methyl 7-(2,3-difluorophenoxy)-4-hydroxy-1-methyl-2-oxo-1,2-dihydroquinoline-3-carboxylate (310 mg, 0.858 mmol) and sodium glycinate (170 mg, 1.75 mmol) in ethylene glycol monomethyl ether (30 mL) was refluxed for 2 h. The mixture was cooled to room temperature and concentrated in vacuo to remove the solvent. The residue was dissolved in water (30 mL) and the mixture was acidified with diluted hydrochloric acid (1 M) to pH 4, then the resulting mixture was extracted with ethyl acetate (50 mL×3). The combined organic layers were washed successively with water (30 mL×2) and saturated brine (30 mL), dried over anhydrous sodium sulfate, and filtered. The filtrate was concentrated in vacuo to remove the solvent, and the residue was purified by preparative chromatography to give a white solid (22 mg, 6.09%).

MS (ESI, pos.ion) m/z: 404.8 (M+1);

$^1$H NMR (400 MHz, DMSO-$d_6$) δ (ppm): 10.47 (s, 1H), 8.10 (d, J=8.9 Hz, 1H), 7.46-7.25 (m, 3H), 7.19 (t, J=7.7 Hz, 1H), 6.97 (dd, J=8.9, 2.0 Hz, 1H), 4.12 (d, J=5.5 Hz, 2H), 3.57 (s, 3H).

Example 15: 2-(7-(2,4-difluorophenoxy)-4-hydroxy-1-methyl-2-oxo-1,2-dihydroquinoline-3-carboxamido)acetic acid

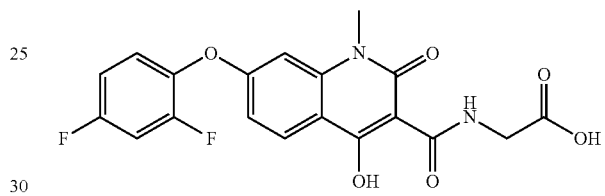

Step 1: methyl 7-(2,4-difluorophenoxy)-4-hydroxy-1-methyl-2-oxo-1,2-dihydroquinoline-3-carboxylate To a two-neck round-bottom flask were added methyl 7-bromo-4-hydroxy-1-methyl-2-oxo-1,2-dihydroquinoline-3-carboxylate (2.00 g, 6.41 mmol), 2,4-difluorophenol (1.25 g, 9.61 mmol), cuprous iodide (0.245 g, 1.29 mmol), N,N-dimethylglycine (0.200 g, 1.94 mmol), cesium carbonate (5.22 g, 16.0 mmol) and dimethyl sulfoxide (40 mL) in turn under nitrogen protection. The mixture was stirred at 140° C. for 30 h. The mixture was cooled to room temperature and acidified with diluted hydrochloric acid (1 M) to pH 4, and the resulting mixture was extracted with ethyl acetate (50 mL×3). The combined organic layers were washed successively with water (50 mL×2) and saturated brine (40 mL), dried over anhydrous sodium sulfate, and filtered. The filtrate was concentrated in vacuo to remove the solvent. The residue was purified by column chromatography (petroleum ether/ethyl acetate (v/v)=1/2) to give a white solid (0.570 g, 24.6%).

MS (ESI, pos.ion) m/z: 361.8 (M+1).

Step 2: 2-(7-(2,4-difluorophenoxy)-4-hydroxy-1-methyl-2-oxo-1,2-dihydroquinoline-3-carboxamido)acetic acid A mixture of methyl 7-(2,4-difluorophenoxy)-4-hydroxy-1-methyl-2-oxo-1,2-dihydroquinoline-3-carboxylate (0.570 g, 1.58 mmol) and sodium glycinate (0.306 g, 3.15 mmol) in ethylene glycol monomethyl ether (20 mL) was refluxed for 1 h. The mixture was cooled to room temperature and concentrated in vacuo to remove the solvent. To the residue was added water (20 mL) and the mixture was acidified with diluted hydrochloric acid (1 M) to pH 3, then the resulting mixture was filtered. The filter cake was washed with water and dried, which was recrystallized from ethyl acetate/petroleum ether ((v/v)=1/3) to give a white solid (0.330 g, 51.7%).

MS (ESI, neg.ion) m/z: 403.1 (M−1);

$^1$H NMR (400 MHz, DMSO-$d_6$) δ (ppm): 12.91 (s, 1H), 10.45 (t, J=5.5 Hz, 1H), 8.06 (d, J=8.9 Hz, 1H), 7.61-7.53 (m, 1H), 7.48 (td, J=9.2, 5.7 Hz, 1H), 7.22 (t, J=8.2 Hz, 1H), 7.17 (d, J=2.0 Hz, 1H), 6.86 (dd, J=8.9, 1.9 Hz, 1H), 4.13 (d, J=5.5 Hz, 2H), 3.55 (s, 3H).

Example 16: 2-(7-(2,6-difluorophenoxy)-4-hydroxy-1-methyl-2-oxo-1,2-dihydroquinoline-3-carboxamido)acetic acid

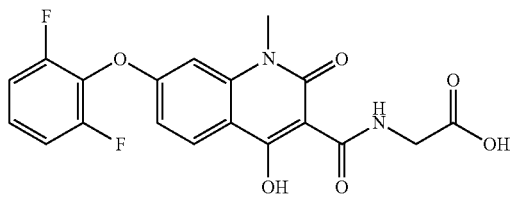 [SMILES: Cn1c(=O)c(C(=O)NCC(=O)O)c(O)c2ccc(Oc3c(F)cccc3F)cc21]

Step 1: 2,6-difluorophenol

To a solution of 2,6-difluoroanisole (4.00 mL, 33.9 mmol) and sodium iodide (15.0 g, 100 mmol) in acetonitrile (50 mL) was added trimethylchlorosilane (8.80 mL, 102 mmol). The mixture was stirred at 100° C. for 5 h. The mixture was cooled to room temperature and concentrated in vacuo to remove the solvent. To the residue was added water (40 mL), and the mixture was extracted with dichloromethane (30 mL×3). The combined organic layers were washed successively with water (40 mL) and saturated brine (40 mL), dried over anhydrous sodium sulfate, filtered and concentrated in vacuo to remove the solvent. The residue was purified by column chromatography (petroleum ether/ethyl acetate (v/v)=6/1) to give yellow oil (2.2 g, 50%).

$^1$H NMR (400 MHz, CDCl$_3$) δ (ppm): 6.90 (t, J=7.8 Hz, 2H), 6.80 (m, 1H), 5.82 (s, 1H).

Step 2: methyl 7-(2,6-difluorophenoxy)-4-hydroxy-1-methyl-2-oxo-1,2-dihydroquinoline-3-carboxylate To a two-neck flask were added methyl 7-bromo-4-hydroxy-1-methyl-2-oxo-1,2-dihydroquinoline-3-carboxylate (4.00 g, 12.8 mmol), 2,6-difluorophenol (2.20 g, 16.9 mmol), cuprous iodide (1.00 g, 5.25 mmol), N,N-dimethylglycine (900 mg, 8.73 mmol), cesium carbonate (10.5 g, 32.2 mmol) and dimethyl sulfoxide (100 mL) in turn under nitrogen protection. The mixture was stirred at 150° C. for 35 h. The mixture was cooled to room temperature and acidified with diluted hydrochloric acid (1 M) to pH 4, and the resulting mixture was extracted with ethyl acetate (50 mL×3). The combined organic layers were washed successively with water (50 mL×2) and saturated brine (50 mL), dried over anhydrous sodium sulfate, and filtered. The filtrate was concentrated in vacuo to remove the solvent. The residue was purified by column chromatography (PE/EtOAc (v/v)=3/1) to give a crude product, which were further purified by preparative chromatography to give a white solid (440 mg, 9.50%).

MS (ESI, pos.ion) m/z: 361.9 (M+1).

Step 3: 2-(7-(2,6-difluorophenoxy)-4-hydroxy-1-methyl-2-oxo-1,2-dihydroquinoline-3-carboxamido)acetic acid A solution of methyl 7-(2,6-difluorophenoxy)-4-hydroxy-1-methyl-2-oxo-1,2-dihydroquinoline-3-carboxylate (440 mg, 1.22 mmol) and sodium glycinate (240 mg, 2.47 mmol) in ethylene glycol monomethyl ether (50 mL) was refluxed for 2 h. The mixture was cooled to room temperature and filtered. The filter cake was washed with ethyl acetate and dissolved in water (20 mL), and the mixture was acidified with diluted hydrochloric acid (1 M) to pH 4, then the resulting mixture was filtered. The filter cake was washed with ethyl acetate and dried to give a white solid (330 mg, 67.02%).

MS (ESI, pos.ion) m/z: 404.8 (M+1);

$^1$H NMR (400 MHz, DMSO-$d_6$) δ (ppm): 10.46 (t, J=5.4 Hz, 1H), 8.08 (d, J=8.9 Hz, 1H), 7.52-7.33 (m, 3H), 7.24 (d, J=2.0 Hz, 1H), 6.86 (dd, J=8.9, 1.8 Hz, 1H), 4.13 (d, J=5.5 Hz, 2H), 3.57 (s, 3H).

Example 17: 2-(7-(3,4-difluorophenoxy)-4-hydroxy-1-methyl-2-oxo-1,2-dihydroquinoline-3-carboxamido)acetic acid

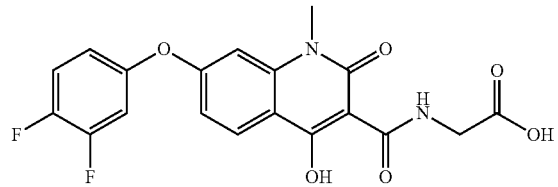 [SMILES: Cn1c(=O)c(C(=O)NCC(=O)O)c(O)c2ccc(Oc3ccc(F)c(F)c3)cc21]

Step 1: methyl 7-(3,4-difluorophenoxy)-4-hydroxy-1-methyl-2-oxo-1,2-dihydroquinoline-3-carboxylate To a two-neck round-bottom flask were added methyl 7-bromo-4-hydroxy-1-methyl-2-oxo-1,2-dihydroquinoline-3-carboxylate (1.00 g, 3.20 mmol), 3,4-difluorophenol (0.542 g, 4.17 mmol), cuprous iodide (0.123 g, 0.646 mmol), N,N-dimethylglycine (0.100 g, 0.970 mmol), cesium carbonate (2.61 g, 8.01 mmol) and dimethyl sulfoxide (20 mL) in turn under nitrogen protection. The mixture was stirred at 140° C. for 18 h. The mixture was cooled to room temperature and acidified with diluted hydrochloric acid (1 M) to pH 4, and the resulting mixture was extracted with ethyl acetate (50 mL×3). The combined organic layers were washed successively with water (50 mL×2) and saturated brine (50 mL), dried over anhydrous sodium sulfate, and filtered. The filtrate was concentrated in vacuo to remove the solvent. The residue was purified by column chromatography (petroleum ether/ethyl acetate (v/v)=1/2) to give a white solid (0.544 g, 47.0%).

MS (ESI, pos.ion) m/z: 361.8 (M+1).

Step 2: 2-(7-(3,4-difluorophenoxy)-4-hydroxy-1-methyl-2-oxo-1,2-dihydroquinoline-3-carboxamido)acetic acid A solution of methyl 7-(3,4-difluorophenoxy)-4-hydroxy-1-methyl-2-oxo-1,2-dihydroquinoline-3-carboxylate (0.544 g, 1.51 mmol) and sodium glycinate (0.294 g, 3.03 mmol) in ethylene glycol monomethyl ether (10 mL) was refluxed for 2 h. The mixture was cooled to room temperature and concentrated in vacuo. To the residue was added water (20 mL) and the mixture was acidified with diluted hydrochloric acid (1 M) to pH 3, then the resulting mixture was filtered. The filter cake was washed with water and dried, which was recrystallized from (ethyl acetate/petrol ether (v/v)=1/3) to give a white solid (0.110 g, 18.1%).

MS (ESI, pos.ion) m/z: 404.8 (M+1);

$^1$H NMR (400 MHz, DMSO-d$_6$) δ (ppm): 10.46 (s, 1H), 8.08 (d, J=8.9 Hz, 1H), 7.54 (dd, J=19.3, 9.4 Hz, 1H), 7.47-7.38 (m, 1H), 7.19 (s, 1H), 7.07 (d, J=8.3 Hz, 1H), 6.95 (dd, J=8.8, 1.6 Hz, 1H), 4.12 (d, J=5.4 Hz, 2H), 3.55 (s, 3H).

Example 18: 2-(7-(3,5-difluorophenoxy)-4-hydroxy-1-methyl-2-oxo-1,2-dihydroquinoline-3-carboxamido)acetic acid

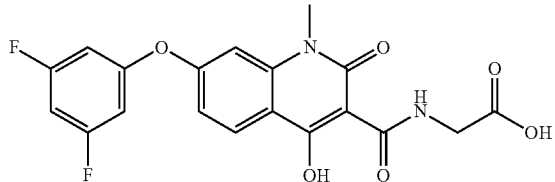 [SMILES: Cn1c(=O)c(C(=O)NCC(=O)O)c(O)c2ccc(Oc3cc(F)cc(F)c3)cc21]

Step 1: methyl 7-(3,5-difluorophenoxy)-4-hydroxy-1-methyl-2-oxo-1,2-dihydroquinoline-3-carboxylate To a two-neck round-bottom flask were added methyl 7-bromo-4-hydroxy-1-methyl-2-oxo-1,2-dihydroquinoline-3-carboxylate (500 mg, 1.60 mmol), 3,5-difluorophenol (271 mg, 2.08 mmol), cuprous iodide (61 mg, 0.32 mmol), N,N-dimethylglycine (50 mg, 0.485 mmol), cesium carbonate (1.30 g, 4.00 mmol) and dimethyl sulfoxide (20 mL) in turn under nitrogen protection. The mixture was stirred at 140° C. for 20 h. The mixture was cooled to room temperature and acidified with diluted hydrochloric acid (1 M) to pH 4, and the resulting mixture was extracted with ethyl acetate (50 mL×3). The combined organic layers were washed successively with water (50 mL×2) and saturated brine (50 mL), dried over anhydrous sodium sulfate, and filtered. The filtrate was concentrated in vacuo to remove the solvent. The residue was purified by column chromatography (petroleum ether/ethyl acetate (v/v)=2/1,) to give a white solid (350 mg, 60.45%).

MS (ESI, pos.ion) m/z: 361.9 (M+1).

Step 2: 2-(7-(3,5-difluorophenoxy)-4-hydroxy-1-methyl-2-oxo-1,2-dihydroquinoline-3-carboxamido)acetic acid A solution of methyl 7-(3,5-difluorophenoxy)-4-hydroxy-1-methyl-2-oxo-1,2-dihydroquinoline-3-carboxylate (350 mg, 0.969 mmol) and sodium glycinate (200 mg, 2.06 mmol) in ethylene glycol monomethyl ether (30 mL) was refluxed for 2 h. The mixture was cooled to room temperature and concentrated in vacuo to remove the solvent. To the residue was added water (30 mL) and the mixture was acidified with diluted hydrochloric acid (1 M) to pH 4, then the resulting mixture was extracted with ethyl acetate (30 mL×3). The combined organic layers were washed successively with water (50 mL) and saturated brine (50 mL), dried over anhydrous sodium sulfate, and filtered. The filtrate was concentrated in vacuo to remove the solvent and give a white solid (172 mg, 43.9%).

MS (ESI, pos.ion) m/z: 404.8 (M+1);

$^1$H NMR (400 MHz, DMSO-d$_6$) δ (ppm): 10.48 (t, J=5.2 Hz, 1H), 8.13 (d, J=8.8 Hz, 1H), 7.32 (d, J=2.0 Hz, 1H), 7.13 (tt, J=9.3, 2.2 Hz, 1H), 7.05 (dd, J=8.8, 2.1 Hz, 1H), 6.97 (dd, J=8.2, 2.0 Hz, 2H), 4.13 (d, J=5.5 Hz, 2H), 3.58 (s, 3H).

Example 19: 2-(7-(2,5-difluorophenoxy)-4-hydroxy-1-methyl-2-oxo-1,2-dihydroquinoline-3-carboxamido)acetic acid

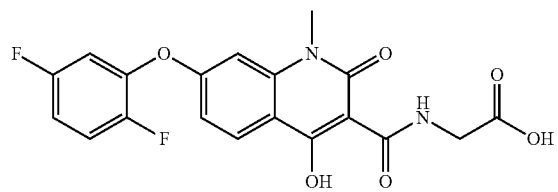 [SMILES: Cn1c(=O)c(C(=O)NCC(=O)O)c(O)c2ccc(Oc3cc(F)ccc3F)cc21]

Step 1: methyl 7-(2,5-difluorophenoxy)-4-hydroxy-1-methyl-2-oxo-1,2-dihydroquinoline-3-carboxylate To a three-neck flask were added 2,5-difluorophenol (1.25 g, 9.61 mmol), methyl 7-bromo-4-hydroxy-1-methyl-2-oxo-1,2-dihydroquinoline-3-carboxylate (2.00 g, 6.41 mmol), N,N-dimethylglycine (0.20 g, 1.94 mmol), cuprous iodide (0.245 g, 1.29 mmol), cesium carbonate (5.22 g, 16.0 mmol) and dimethyl sulfoxide (40 mL) in turn under nitrogen protection. The mixture was stirred at 140° C. for 30 h. The mixture was cooled to room temperature and acidified with diluted hydrochloric acid (1 M) to pH 3. To the mixture was added water (60 mL), and the resulting mixture was extracted with ethyl acetate (50 mL×3). The combined organic layers were washed successively with water (30 mL×2) and saturated brine (50 mL), dried over anhydrous sodium sulfate, and filtered. The filtrate was concentrated in vacuo to remove the solvent. The residue was purified by column chromatography (petroleum ether/ethyl acetate (v/v)=1/2) to give a white solid (500 mg, 21.6%).

MS (ESI, pos.ion) m/z: 362.1 (M+1).

Step 2: 2-(7-(2,5-difluorophenoxy)-4-hydroxy-1-methyl-2-oxo-1,2-dihydroquinoline-3-carboxamido)acetic acid To a solution of methyl 7-(2,5-difluorophenoxy)-4-hydroxy-1-methyl-2-oxo-1,2-dihydroquinoline-3-carboxylate (0.500 g, 1.38 mmol) in ethylene glycol monomethyl ether (20 mL) was added sodium glycinate (0.268 g, 2.76 mmol). The mixture was stirred at 130° C. for 1 h. The mixture was cooled to room temperature and concentrated in vacuo to remove the solvent. To the residue was added water (20 mL) and the mixture was acidified with diluted hydrochloric acid (1 M) to pH 3. The resulting mixture was filtered, and the filter cake washed with water and dried, which was purified by recrystallization from ethyl acetate/petroleum ether ((v/v)=1/3) to give a white solid (200 mg, 40.0%).

MS (ESI, neg.ion) m/z: 403.15 (M−1);

$^1$H NMR (400 MHz, DMSO-d$_6$) δ (ppm): 10.47 (s, 1H), 8.10 (d, J=8.9 Hz, 1H), 7.60-7.48 (m, J=9.8, 5.2 Hz, 1H), 7.41-7.31 (m, 1H), 7.27-7.15 (m, 2H), 6.95 (d, J=8.8 Hz, 1H), 4.12 (d, J=5.5 Hz, 2H), 3.57 (s, 3H).

Example 20: 2-(7-(3-chloro-2-fluorophenoxy)-4-hydroxy-1-methyl-2-oxo-1,2-dihydroquinoline-3-carboxamido)acetic acid

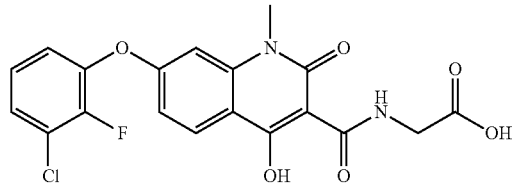 [SMILES: Cn1c(=O)c(C(=O)NCC(=O)O)c(O)c2ccc(Oc3cccc(Cl)c3F)cc21]

Step 1: methyl 7-(3-chloro-2-fluorophenoxy)-4-hydroxy-1-methyl-2-oxo-1,2-dihydroquinoline-3-carboxylate To a two-neck flask were added methyl 7-bromo-4-hydroxy-1-methyl-2-oxo-1,2-dihydroquinoline-3-carboxylate (2.00 g, 6.41 mmol), 3-chloro-2-fluorophenol (1.50 g, 10.2 mmol), cuprous iodide (490 mg, 2.57 mmol), N,N-dimethylglycine (400 mg, 3.88 mmol), cesium carbonate (5.2 g, 16.0 mmol) and dimethyl sulfoxide (50 mL) in turn under nitrogen protection. The mixture was stirred at 150° C. for 30 h. The mixture was cooled to room temperature, and water (50 mL) was added. The mixture was acidified with diluted hydrochloric acid (1 M) to pH 4, and the resulting mixture was extracted with ethyl acetate (30 mL×3). The combined organic layers were washed with water (20 mL×2) and saturated brine (40 mL), dried over anhydrous sodium sulfate. The filtrate was concentrated in vacuo to remove the solvent. The residue was purified by column chromatography (petroleum ether/ethyl acetate (v/v)=4/1) to give a crude product, which were further purified by column chromatography to give a white solid (550 mg, 22.7%).

MS (ESI, pos.ion) m/z: 378.1 (M+1).

Step 2: 2-(7-(3-chloro-2-fluorophenoxy)-4-hydroxy-1-methyl-2-oxo-1,2-dihydroquinoline-3-carboxamido)acetic acid A solution of methyl 7-(3-chloro-2-fluorophenoxy)-4-hydroxy-1-methyl-2-oxo-1,2-dihydroquinoline-3-carboxylate (550 mg, 1.46 mmol) and sodium glycinate (290 mg, 2.99 mmol) in ethylene glycol monomethyl ether (20 mL) was refluxed for 2 h. The mixture was cooled to room temperature and filtered. The filter cake was washed with ethyl acetate and dissolved in water (20 mL), and the mixture was acidified with diluted hydrochloric acid (1 M) to pH 4, then the resulting mixture was filtered. The filter cake was washed with ethyl acetate and dried to give a white solid (350 mg, 57.1%).

MS (ESI, pos.ion) m/z: 420.8 (M+1);

$^1$H NMR (400 MHz, DMSO-$d_6$) δ (ppm): 12.92 (s, 1H), 10.47 (t, J=5.5 Hz, 1H), 8.09 (d, J=8.9 Hz, 1H), 7.58-7.49 (m, 1H), 7.40-7.26 (m, 3H), 6.94 (dd, J=8.9, 1.9 Hz, 1H), 4.13 (d, J=5.5 Hz, 2H), 3.57 (s, 3H).

Example 21: 2-(7-(4-chloro-2-fluorophenoxy)-4-hydroxy-1-methyl-2-oxo-1,2-dihydroquinoline-3-carboxamido)acetic acid

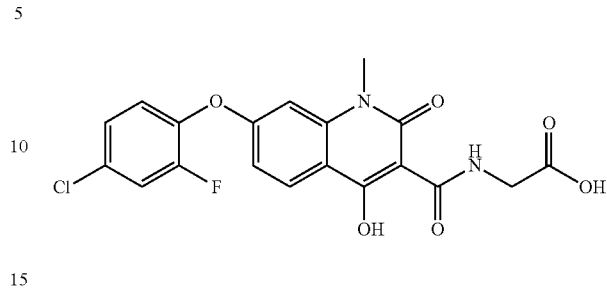

Step 1: methyl 7-(4-chloro-2-fluorophenoxy)-4-hydroxy-1-methyl-2-oxo-1,2-dihydroquinoline-3-carboxylate To a two-neck flask were added methyl 7-bromo-4-hydroxy-1-methyl-2-oxo-1,2-dihydroquinoline-3-carboxylate (500 mg, 1.60 mmol), 4-chloro-2-fluorophenol (353 mg, 2.41 mmol), cuprous iodide (61 mg, 0.32 mmol), N,N-dimethylglycine (67 mg, 0.65 mmol), cesium carbonate (1.3 g, 4.0 mmol) and dimethyl sulfoxide (15 mL) in turn under nitrogen protection. The mixture was stirred at 140° C. for 20 hours. The mixture was cooled to room temperature and acidified with diluted hydrochloric acid (1 M) to pH 4, and the resulting mixture was extracted with ethyl acetate (20 mL×3). The combined organic layers were washed successively with water (30 mL×2) and saturated brine (40 mL), dried over anhydrous sodium sulfate, and filtered. The filtrate was concentrated in vacuo to remove the solvent. The residue was purified by column chromatography (petroleum ether/ethyl acetate (v/v)=1/1) to give a light yellow solid (130 mg, 21.5%).

MS (ESI, pos.ion) m/z: 378.1 (M+1).

Step 2: 2-(7-(4-chloro-2-fluorophenoxy)-4-hydroxy-1-methyl-2-oxo-1,2-dihydroquinoline-3-carboxamido)acetic acid A mixture of methyl 7-(4-chloro-2-fluorophenoxy)-4-hydroxy-1-methyl-2-oxo-1,2-dihydroquinoline-3-carboxylate (132 mg, 0.349 mmol) and sodium glycinate (102 mg, 1.05 mmol) in ethylene glycol monomethyl ether (25 mL) was refluxed for 3 h. The mixture was cooled to room temperature and concentrated in vacuo to remove the solvent. To the residue was added water (10 mL) and the mixture was acidified with diluted hydrochloric acid (1 M) to pH 4, then the resulting mixture was extracted with ethyl acetate (15 mL×3). The combined organic layers were washed successively with water (30 mL×2) and saturated brine (40 mL), dried over anhydrous sodium sulfate, and filtered. The filtrate was concentrated in vacuo to give a light yellow solid (40 mg, 27.2%).

MS (ESI, pos.ion) m/z: 421.2 (M+1);

$^1$H NMR (400 MHz, DMSO-$d_6$) δ (ppm): 12.90 (s, 1H), 10.46 (t, J=5.5 Hz, 1H), 8.07 (d, J=8.9 Hz, 1H), 7.76-7.69 (m, 1H), 7.47-7.35 (m, 2H), 7.22 (d, J=2.1 Hz, 1H), 6.94-6.85 (m, 1H), 4.13 (d, J=5.5 Hz, 2H), 3.56 (s, 3H).

Example 22: 2-(7-(5-chloro-2-fluorophenoxy)-4-hydroxy-1-methyl-2-oxo-1,2-dihydroquinoline-3-carboxamido)acetic acid

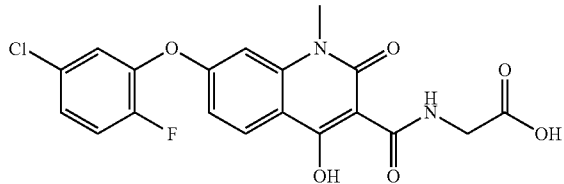 [SMILES: Cn1c(=O)c(C(=O)NCC(=O)O)c(O)c2ccc(Oc3cc(Cl)ccc3F)cc21]

Step 1: methyl 7-(5-chloro-2-fluorophenoxy)-4-hydroxy-1-methyl-2-oxo-1,2-dihydroquinoline-3-carboxylate To a round-bottom flask were added methyl 7-bromo-4-hydroxy-1-methyl-2-oxo-1,2-dihydroquinoline-3-carboxylate (2.0 g, 6.4 mmol), 5-chloro-2-fluorophenol (1.00 mL, 9.61 mmol), N,N-dimethylglycine (200 mg, 1.94 mmol), cuprous iodide (250 mg, 1.31 mmol), cesium carbonate (5.20 g, 16.0 mmol) and dimethyl sulfoxide (100 mL) in turn under nitrogen protection. The mixture was stirred at 140° C. for 30 h. The mixture was cooled to room temperature, and then water (50 mL) was added. The mixture was acidified with diluted hydrochloric acid (1 M) to pH 4, and the resulting mixture was extracted with ethyl acetate (50 mL×3). The combined organic layers were washed successively with water (10 mL) and saturated brine (30 mL), dried over anhydrous sodium sulfate and filtered. The filtrate was concentrated in vacuo to remove the solvent. The residue was purified by column chromatography (petroleum ether/ethyl acetate (v/v)=4/1) to give a white solid (400 mg, 17.0%).

MS (ESI, pos.ion) m/z: 378.1 (M+1).

Step 2: 2-(7-(5-chloro-2-fluorophenoxy)-4-hydroxy-1-methyl-2-oxo-1,2-dihydroquinoline-3-carboxamido)acetic acid A mixture of methyl 7-(5-chloro-2-fluorophenoxy)-4-hydroxy-1-methyl-2-oxo-1,2-dihydroquinoline-3-carboxylate (400 mg, 1.06 mmol) and sodium glycinate (210 mg, 2.16 mmol) in ethylene glycol monomethyl ether (20 mL) was refluxed for 2 h. The mixture was cooled to room temperature and filtered. The filter cake was washed with ethyl acetate and dissolved in water (20 mL), and the mixture was acidified with diluted hydrochloric acid (1 M) to pH 4, then the resulting mixture was filtered. The filter cake was washed with ethyl acetate and dried to give a white solid (290 mg, 65.1%).

MS (ESI, pos.ion) m/z: 420.8 (M+1);

$^1$H NMR (400 MHz, DMSO-$d_6$) δ (ppm): 12.96 (s, 1H), 10.47 (t, J=5.5 Hz, 1H), 8.10 (d, J=8.9 Hz, 1H), 7.60-7.48 (m, 2H), 7.47-7.38 (m, 1H), 7.27 (d, J=1.9 Hz, 1H), 6.94 (dd, J=8.9, 1.9 Hz, 1H), 4.13 (d, J=5.5 Hz, 2H), 3.58 (s, 3H).

Example 23: 2-(7-(2-chloro-6-fluorophenoxy)-4-hydroxy-1-methyl-2-oxo-1,2-dihydroquinoline-3-carboxamido)acetic acid

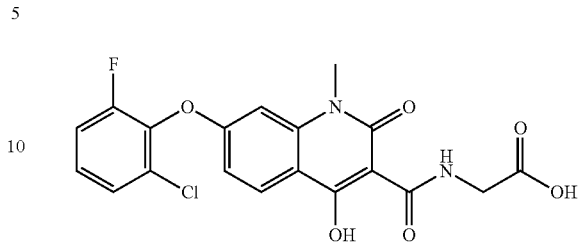

Step 1: methyl 7-(2-chloro-6-fluorophenoxy)-4-hydroxy-1-methyl-2-oxo-1,2-dihydroquinoline-3-carboxylate To a two-neck flask were added methyl 7-bromo-4-hydroxy-1-methyl-2-oxo-1,2-dihydroquinoline-3-carboxylate (4.00 g, 12.8 mmol), 2-chloro-6-fluorophenol (2.50 g, 17.1 mmol), cuprous iodide (1.00 g, 5.25 mmol), N,N-dimethylglycine (900 mg, 8.73 mmol), cesium carbonate (10.5 g, 32.2 mmol) and dimethyl sulfoxide (20 mL) in turn under nitrogen protection. The mixture was stirred at 150° C. for 35 h. The mixture was cooled to room temperature and to the mixture was added water (60 mL). The resulting mixture was acidified with diluted hydrochloric acid (1 M) to pH 4, then the mixture was extracted with ethyl acetate (50 mL×3). The combined organic layers were washed successively with water (50 mL×2) and saturated brine (50 mL), dried over anhydrous sodium sulfate and filtered. The filtrate was concentrated in vacuo to remove solvent. The residue was purified by column chromatography (petroleum ether/ethyl acetate (v/v)=4/1) to give a crude product, which were further purified by preparative chromatography to give a white solid (100 mg, 2.07%).

MS (ESI, pos.ion) m/z: 378.1 (M+1).

Step 2: 2-(7-(2-chloro-6-fluorophenoxy)-4-hydroxy-1-methyl-2-oxo-1,2-dihydroquinoline-3-carboxamido)acetic acid A mixture of methyl 7-(2-chloro-6-fluorophenoxy)-4-hydroxy-1-methyl-2-oxo-1,2-dihydroquinoline-3-carboxylate (100 mg, 0.26 mmol) and sodium glycinate (50 mg, 0.51 mmol) in ethylene glycol monomethyl ether (20 mL) was refluxed for 2 h. The mixture was cooled to room temperature and filtered. The filter cake was washed with ethyl acetate and dissolved in water (20 mL), and the mixture was acidified with diluted hydrochloric acid (1 M) to pH 4, then the resulting mixture was filtered. The filter cake was washed with ethyl acetate and dried to give a white solid (60 mg, 53.9%).

MS (ESI, pos.ion) m/z: 420.8 (M+1);

$^1$H NMR (400 MHz, DMSO-$d_6$) δ (ppm): 12.92 (s, 1H), 10.46 (t, J=5.5 Hz, 1H), 8.08 (d, J=8.9 Hz, 1H), 7.63-7.41 (m, 3H), 7.23 (d, J=2.1 Hz, 1H), 6.76 (dd, J=8.9, 2.0 Hz, 1H), 4.13 (d, J=5.5 Hz, 2H), 3.58 (s, 3H).

Example 24: 2-(7-(2-chloro-3-fluorophenoxy)-4-hydroxy-1-methyl-2-oxo-1,2-dihydroquinoline-3-carboxamido)acetic acid

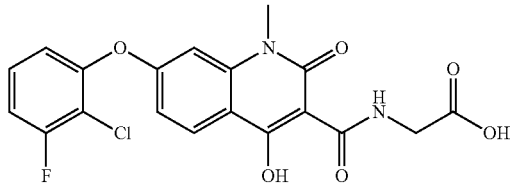 [SMILES: Cn1c(=O)c(C(=O)NCC(=O)O)c(O)c2ccc(Oc3cccc(F)c3Cl)cc21]

Step 1: methyl 7-(2-chloro-3-fluorophenoxy)-4-hydroxy-1-methyl-2-oxo-1,2-dihydroquinoline-3-carboxylate To a three-neck flask were added 2-chloro-3-fluorophenol (1.41 g, 9.62 mmol), methyl 7-bromo-4-hydroxy-1-methyl-2-oxo-1,2-dihydroquinoline-3-carboxylate (2.00 g, 6.41 mmol), N,N-dimethylglycine (400 mg, 3.88 mmol), cuprous iodide (490 mg, 2.57 mmol), cesium carbonate (5.22 g, 16.0 mmol) and dimethyl sulfoxide (15 mL) in turn under nitrogen protection. The mixture was stirred at 140° C. for 24 h. The mixture was cooled to room temperature and acidified with diluted hydrochloric acid (1 M) to pH 3, and the resulting mixture was extracted with ethyl acetate (30 mL×3). The combined organic layers were washed successively with water (30 mL×2) and saturated brine (50 mL), dried over anhydrous sodium sulfate, and filtered. The filtrate was concentrated in vacuo to remove the solvent. The residue was purified by column chromatography (petroleum ether/ethyl acetate (v/v)=1/2) to give a red solid (240 mg, 10.0%).

Step 2: 2-(7-(2-chloro-3-fluorophenoxy)-4-hydroxy-1-methyl-2-oxo-1,2-dihydroquinoline-3-carboxamido)acetic acid To a solution of methyl 7-(2-chloro-3-fluorophenoxy)-4-hydroxy-1-methyl-2-oxo-1,2-dihydroquinoline-3-carboxylate (240 mg, 0.635 mmol) in ethylene glycol monomethyl ether (25 mL) was added sodium glycinate (320 mg, 3.30 mmol). The mixture was stirred at 130° C. for 3 h. The mixture was cooled to room temperature and concentrated in vacuo to remove the solvent. To the residue was added water (15 mL) and the mixture was acidified with diluted hydrochloric acid (1 M) to pH 3. The resulting mixture was extracted with EtOAc (20 mL×3). The combined organic layers were washed with saturated brine (45 mL), dried over anhydrous sodium sulfate, and filtered. The filtrate was concentrated in vacuo to remove solvent and give a pink solid (250.6 mg, 93.8%).

MS (ESI, pos.ion) m/z: 420.8 (M+1);

$^1$H NMR (400 MHz, DMSO-d$_6$) δ (ppm): 10.46 (t, J=5.4 Hz, 1H), 8.09 (d, J=8.9 Hz, 1H), 7.54-7.43 (m, 1H), 7.38 (t, J=8.2 Hz, 1H), 7.27 (d, J=2.0 Hz, 1H), 7.17 (d, J=8.3 Hz, 1H), 6.93-6.80 (m, 1H), 4.13 (d, J=5.5 Hz, 2H), 3.57 (s, 3H).

Example 25: 2-(7-(4-chloro-3-fluorophenoxy)-4-hydroxy-1-methyl-2-oxo-1,2-dihydroquinoline-3-carboxamido)acetic acid

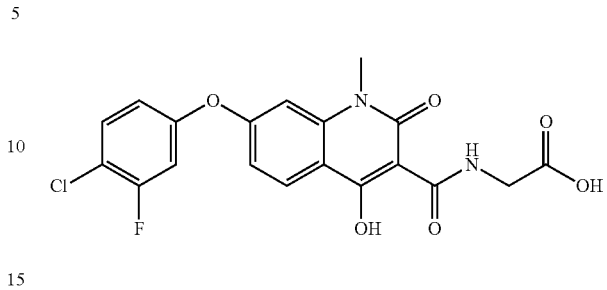

Step 1: methyl 7-(4-chloro-3-fluorophenoxy)-4-hydroxy-1-methyl-2-oxo-1,2-dihydroquinoline-3-carboxylate To a three-neck flask were added methyl 7-bromo-4-hydroxy-1-methyl-2-oxo-1,2-dihydroquinoline-3-carboxylate (500 mg, 1.60 mmol), 4-chloro-3-fluorophenol (305 mg, 2.08 mmol), N,N-dimethylglycine (50 mg, 0.485 mmol), cuprous iodide (61 mg, 0.320 mmol), cesium carbonate (1.30 g, 3.99 mmol) and dimethyl sulfoxide (20 mL) in turn under nitrogen protection. The mixture was stirred at 140° C. for 20 h. The mixture was cooled to room temperature, and water (20 mL) was added. The resulting mixture was extracted with EtOAc (20 mL×3). The combined organic layers were washed successively with water (30 mL) and saturated brine (30 mL), dried over anhydrous sodium sulfate, and filtered. The filtrate was concentrated in vacuo to remove the solvent. The residue was purified by column chromatography (petroleum ether/ethyl acetate (v/v)=2/1) to give a white solid (400 mg, 66.2%).

MS (ESI, pos.ion) m/z: 378.1 (M+1).

Step 2: 2-(7-(4-chloro-3-fluorophenoxy)-4-hydroxy-1-methyl-2-oxo-1,2-dihydroquinoline-3-carboxamido)acetic acid To a solution of methyl 7-(4-chloro-3-fluorophenoxy)-4-hydroxy-1-methyl-2-oxo-1,2-dihydroquinoline-3-carboxylate (400 mg, 1.06 mmol) in ethylene glycol monomethyl ether (30 mL) was added sodium glycinate (200 mg, 2.06 mmol). The mixture was refluxed for 2 h. The mixture was cooled to room temperature and concentrated in vacuo to remove the solvent. The residue was dissolved in water (30 mL), and the aqueous phase was washed with EtOAc (50 mL×2), then acidified with hydrochloric acid (1 M) to pH 4. The resulting mixture was filtered and the filter cake was washed with water, then dried in oven to give a white solid (15 mg, 3.37%).

MS (ESI, pos.ion) m/z: 420.8 (M+1);

$^1$H NMR (400 MHz, DMSO-d$_6$) δ (ppm): 12.93 (s, 1H), 10.47 (s, 1H), 8.10 (d, J=8.8 Hz, 1H), 7.67 (t, J=8.7 Hz, 1H), 7.37 (d, J=8.7 Hz, 1H), 7.28 (s, 1H), 7.04 (dd, J=21.6, 8.5 Hz, 2H), 4.13 (d, J=5.4 Hz, 2H), 3.57 (s, 3H).

Example 26: 2-(7-(3-chloro-5-fluorophenoxy)-4-hydroxy-1-methyl-2-oxo-1,2-dihydroquinoline-3-carboxamido)acetic acid

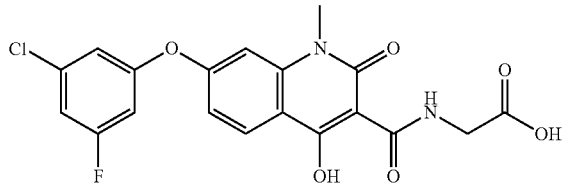 [SMILES: Cn1c(=O)c(C(=O)NCC(=O)O)c(O)c2ccc(Oc3cc(F)cc(Cl)c3)cc21]

Step 1: methyl 7-(3-chloro-5-fluorophenoxy)-4-hydroxy-1-methyl-2-oxo-1,2-dihydroquinoline-3-carboxylate To a two-neck flask were added methyl 6-bromo-4-hydroxy-1-methyl-2-oxo-1,2-dihydroquinoline-3-carboxylate (1.80 g, 5.77 mmol), cesium carbonate (3.80 g, 12.0 mmol), cuprous iodide (440 mg, 2.30 mmol), N,N-dimethylglycine (360 mg, 3.50 mmol), 3-chloro-5-fluorophenol (850 mg, 5.80 mmol) and N,N-dimethylformamide (30 mL) in turn under nitrogen protection. The mixture was stirred at 140° C. for 38 h. The reaction mixture was cooled to room temperature and diluted with water (30 mL). The resulting mixture was acidified with hydrochloric acid (2 M) to pH 5, and the mixture was extracted with EtOAc (100 mL×2). The combined organic layers were dried over anhydrous sodium sulfate, and filtered. The filtrate was concentrated in vacuo to remove the solvent. The residue was purified by column chromatography (PE/EtOAc (v/v)=3/1) to give red oil (650 mg, 29.8%).

MS (ESI, pos.ion) m/z: 378.2 (M+1).

Step 2: 2-(7-(3-chloro-5-fluorophenoxy)-4-hydroxy-1-methyl-2-oxo-1,2-dihydroquinoline-3-carboxamido)acetic acid To a single-neck flask were added methyl 7-(3-chloro-5-fluorophenoxy)-4-hydroxy-1-methyl-2-oxo-1,2-dihydroquinoline-3-carboxylate (150 mg, 0.397 mmol), sodium glycinate (192 mg, 1.98 mmol) and ethylene glycol monomethyl ether (10 mL). The mixture was stirred at 130° C. for 3 h under nitrogen protection. The mixture was cooled to room temperature and filtered by suction. The filter cake was dissolved in water (30 mL) and the mixture was acidified with hydrocloric acid (2 M) to pH 4. The resulting mixture was filtered, and the filter cake was dried in vacuo to give a pale solid (95 mg, 56.9%).

MS (ESI, neg. ion) m/z: 419.10 (M−1);
$^1$H NMR (400 MHz, DMSO-d$_6$) δ (ppm): 10.48 (s, 1H), 8.12 (d, J=8.9 Hz, 1H), 7.39-7.25 (m, 2H), 7.20-7.08 (m, 2H), 7.04 (dd, J=8.8, 2.0 Hz, 1H), 4.13 (d, J=5.5 Hz, 2H), 3.58 (s, 3H).

Example 27: 2-(7-(2-chloro-5-fluorophenoxy)-4-hydroxy-1-methyl-2-oxo-1,2-dihydroquinoline-3-carboxamido)acetic acid

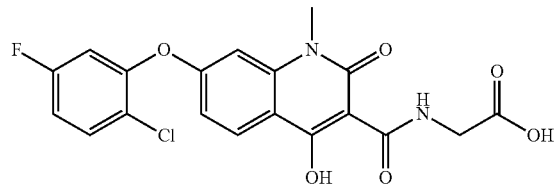

Step 1: methyl 7-(2-chloro-5-fluorophenoxy)-4-hydroxy-1-methyl-2-oxo-1,2-dihydroquinoline-3-carboxylate To a two-neck flask were added methyl 7-bromo-4-hydroxy-1-methyl-2-oxo-1,2-dihydroquinoline-3-carboxylate (2.00 g, 6.41 mmol), 2-chloro-5-fluorophenol (1.41 g, 9.61 mmol), cuprous iodide (0.245 g, 1.29 mmol), N,N-dimethylglycine (0.20 g, 1.94 mmol), cesium carbonate (5.22 g, 16.0 mmol) and dimethyl sulfoxide (40 mL) in turn under nitrogen protection. The mixture was stirred at 140° C. for 30 h. The mixture was cooled to room temperature and acidified with diluted hydrochloric acid (1 M) to pH 4, and the resulting mixture was extracted with ethyl acetate (50 mL×3). The combined organic layers were washed successively with water (20 mL×2) and saturated brine (20 mL), dried over anhydrous sodium sulfate, and filtered. The filtrate was concentrated in vacuo to remove the solvent. The residue was purified by column chromatography (petroleum ether/ethyl acetate (v/v)=1/2) to give a white solid (190 mg, 7.85%).

MS (ESI, pos.ion) m/z: 362.1 (M+1).

Step 2: 2-(7-(2-chloro-5-fluorophenoxy)-4-hydroxy-1-methyl-2-oxo-1,2-dihydroquinoline-3-carboxamido)acetic acid A mixture of methyl 7-(2-chloro-5-fluorophenoxy)-4-hydroxy-1-methyl-2-oxo-1,2-dihydroquinoline-3-carboxylate (0.190 g, 0.503 mmol) and sodium glycinate (0.100 g, 1.03 mmol) in ethylene glycol monomethyl ether (10 mL) was refluxed for 1 h. The mixture was cooled to room temperature and concentrated in vacuo to remove the solvent, and then water (20 mL) was added. The resulting mixture was acidified with diluted hydrochloric acid (1 M) to pH 3, then filtered. The filter cake was washed with water and dried, which was recrystallized from ethyl acetate/petroleum ether ((v/v)=1/3) to give a white solid (200 mg, 40.0%).

$^1$H NMR (400 MHz, DMSO-d$_6$) δ (ppm): 12.92 (s, 1H), 10.47 (s, 1H), 8.10 (d, J=8.8 Hz, 1H), 7.73 (dd, J=8.9, 5.9 Hz, 1H), 7.31 (d, J=9.2 Hz, 1H), 7.23 (dd, J=12.6, 3.9 Hz, 2H), 6.88 (d, J=7.8 Hz, 1H), 4.13 (d, J=5.4 Hz, 2H), 3.58 (s, 3H).

Example 28: 2-(7-(2-chloro-4-fluorophenoxy)-4-hydroxy-1-methyl-2-oxo-1,2-dihydroquinoline-3-carboxamido)acetic acid

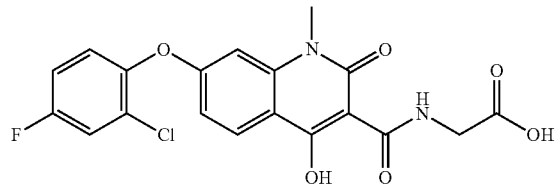 [SMILES: Cn1c(=O)c(C(=O)NCC(=O)O)c(O)c2ccc(Oc3ccc(F)cc3Cl)cc21]

Step 1: methyl 7-(2-chloro-4-fluorophenoxy)-4-hydroxy-1-methyl-2-oxo-1,2-dihydroquinoline-3-carboxylate To a two-neck flask were added methyl 7-bromo-4-hydroxy-1-methyl-2-oxo-1,2-dihydroquinoline-3-carboxylate (1.00 g, 3.20 mmol), 2-chloro-4-fluorophenol (0.60 mL, 5.50 mmol), cuprous iodide (130 mg, 0.683 mmol), N,N-dimethylglycine (100 mg, 0.970 mmol), cesium carbonate (2.60 g, 7.98 mmol) and dimethyl sulfoxide (100 mL) in turn under nitrogen protection. The mixture was stirred at 140° C. for 20 h. The mixture was cooled to room temperature and acidified with diluted hydrochloric acid (1 M) to pH 4, and the resulting mixture was extracted with ethyl acetate (50 mL×2). The combined organic layers were washed with water (50 mL×2) and saturated brine (50 mL), dried over anhydrous sodium sulfate, and filtered. The filtrate was concentrated in vacuo to remove the solvent. The residue was purified by column chromatography (petroleum ether/ethyl acetate (v/v)=4/1) to give a white solid (730 mg, 60.3%).

MS (ESI, pos. ion) m/z: 377.8 (M+1).

Step 2: 2-(7-(2-chloro-4-fluorophenoxy)-4-hydroxy-1-methyl-2-oxo-1,2-dihydroquinoline-3-carboxamido)acetic acid A mixture of methyl 7-(2-chloro-4-fluorophenoxy)-4-hydroxy-1-methyl-2-oxo-1,2-dihydroquinoline-3-carboxylate (730 mg, 1.93 mmol) and sodium glycinate (380 mg, 3.92 mmol) in ethylene glycol monomethyl ether (20 mL) was refluxed for 2 h. The mixture was cooled to room temperature and filtered. The filter cake was washed with ethyl acetate and dissolved in water (20 mL), and the mixture was acidified with diluted hydrochloric acid (1 M) to pH 4, then the resulting mixture was filtered. The filter cake was washed with ethyl acetate and dried to give a white solid (325 mg, 39.97%).

MS (ESI, pos.ion) m/z: 420.8 (M+1);

$^1$H NMR (400 MHz, DMSO-$d_6$) δ (ppm): 12.91 (s, 1H), 10.46 (t, J=5.5 Hz, 1H), 8.07 (d, J=8.9 Hz, 1H), 7.72 (dd, J=8.4, 2.9 Hz, 1H), 7.44 (dd, J=9.0, 5.3 Hz, 1H), 7.36 (td, J=8.6, 3.0 Hz, 1H), 7.18 (d, J=2.1 Hz, 1H), 6.80 (dd, J=8.9, 2.1 Hz, 1H), 4.13 (d, J=5.6 Hz, 2H), 3.56 (s, 3H).

Example 29: 2-(7-(3-chloro-4-fluorophenoxy)-4-hydroxy-1-methyl-2-oxo-1,2-dihydroquinoline-3-carboxamido)acetic acid

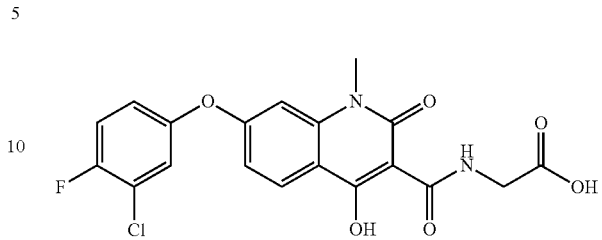

Step 1: methyl 7-(3-chloro-4-fluorophenoxy)-4-hydroxy-1-methyl-2-oxo-1,2-dihydroquinoline-3-carboxylate To a two-neck flask were added methyl 7-bromo-4-hydroxy-1-methyl-2-oxo-1,2-dihydroquinoline-3-carboxylate (500 mg, 1.60 mmol), 3-chloro-4-fluorophenol (353 mg, 2.41 mmol), cuprous iodide (61 mg, 0.320 mmol), N,N-dimethylglycine (67 mg, 0.650 mmol), cesium carbonate (1.3 g, 4.0 mmol) and dimethyl sulfoxide (15 mL) in turn under nitrogen protection. The mixture was stirred at 140° C. overnight. The mixture was cooled to room temperature and acidified with diluted hydrochloric acid (1 M) to pH 3, and the resulting mixture was extracted with ethyl acetate (25 mL×3). The combined organic layers were washed successively with water (40 mL×2) and saturated brine (50 mL), dried over anhydrous sodium sulfate, and filtered. The filtrate was concentrated in vacuo to remove the solvent. The residue was purified by column chromatography (petroleum ether/ethyl acetate (v/v)=1/1) to give a light yellow solid (320 mg, 52.87%).

MS (ESI, pos.ion) m/z: 378.1 (M+1).

Step 2: 2-(7-(3-chloro-4-fluorophenoxy)-4-hydroxy-1-methyl-2-oxo-1,2-dihydroquinoline-3-carboxamido)acetic acid A mixture of methyl 7-(3-chloro-4-fluorophenoxy)-4-hydroxy-1-methyl-2-oxo-1,2-dihydroquinoline-3-carboxylate (320 mg, 0.847 mmol) and sodium glycinate (250 mg, 2.58 mmol) in ethylene glycol monomethyl ether (25 mL) was refluxed for 3 h. The mixture was cooled to room temperature and concentrated in vacuo to remove the solvent. The residue was dissolved in water (10 mL) and the mixture was acidified with diluted hydrochloric acid (1 M) to pH 3, then the resulting mixture was extracted with ethyl acetate (15 mL×3). The combined organic layers were washed successively with water (30 mL×2) and saturated brine (50 mL), dried over anhydrous sodium sulfate, and filtered. The filtrate was concentrated in vacuo to give a light yellow solid (94.5 mg, 26.5%).

MS (ESI, pos.ion) m/z: 421.1 (M+1);

$^1$H NMR (400 MHz, DMSO-$d_6$) δ (ppm): 12.90 (s, 1H), 10.47 (d, J=5.0 Hz, 1H), 8.09 (d, J=8.8 Hz, 1H), 7.58-7.48 (m, 2H), 7.30-7.19 (m, 2H), 6.95 (d, J=8.8 Hz, 1H), 4.13 (d, J=5.5 Hz, 2H), 3.56 (s, 3H).

Example 30: 2-(7-(2,3-dichlorophenoxy)-4-hydroxy-1-methyl-2-oxo-1,2-dihydroquinoline-3-carboxamido)acetic acid

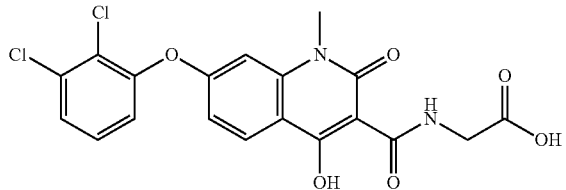 [SMILES: Cn1c(=O)c(C(=O)NCC(=O)O)c(O)c2ccc(Oc3cccc(Cl)c3Cl)cc21]

Step 1: methyl 7-(2,3-dichlorophenoxy)-4-hydroxy-1-methyl-2-oxo-1,2-dihydroquinoline-3-carboxylate To a two-neck round-bottom flask were added methyl 6-bromo-4-hydroxy-1-methyl-2-oxo-1,2-dihydroquinoline-3-carboxylate (2.00 g, 6.40 mmol), cesium carbonate (4.20 g, 13.0 mmol), cuprous iodide (0.49 g, 2.60 mmol), N,N-dimethylglycine (0.40 g, 3.90 mmol), 2,3-dichlorophenol (1.60 g, 9.80 mmol) and N,N-dimethylformamide (30 mL). The mixture was stirred at 140° C. for 28 h under nitrogen protection. The reaction mixture was cooled to room temperature and quenched with water (30 mL). The resulting mixture was acidified with hydrochloric acid (2 M) to pH 5, and the mixture was extracted with EtOAc (100 mL×2). The combined organic layers were dried over anhydrous sodium sulfate, and filtered. The filtrate was concentrated in vacuo to remove the solvent. The residue was purified by column chromatography (petroleum ether/ethyl acetate (v/v)=1/1) to give a pink solid (600 mg, 23.8%).

MS (ESI, pos.ion) m/z: 394.10 (M+1).

Step 2: 2-(7-(2,3-dichlorophenoxy)-4-hydroxy-1-methyl-2-oxo-1,2-dihydroquinoline-3-carboxamido)acetic acid To a single-neck flask were added methyl 7-(2,3-dichlorophenoxy)-4-hydroxy-1-methyl-2-oxo-1,2-dihydroquinoline-3-carboxylate (600 mg, 1.52 mmol), sodium glycinate (0.44 g, 4.5 mmol) and ethylene glycol monomethyl ether (15 mL). The mixture was stirred at 130° C. for 2 h. The mixture was cooled to room temperature and filtered by suction. The filter cake was dissolved in water and the mixture was acidified with diluted hydrocloric acid (2 M) to pH 4. The resulting mixture was filtered, and the filter cake was dried in vacuo to give a pink solid (410 mg, 61.6%).

MS (ESI, pos.ion) m/z: 436.70 (M+1);
$^1$H NMR (400 MHz, DMSO-$d_6$) δ (ppm): 10.46 (d, J=5.4 Hz, 1H), 8.09 (d, J=8.9 Hz, 1H), 7.60 (d, J=7.3 Hz, 1H), 7.47 (t, J=8.2 Hz, 1H), 7.29 (dd, J=12.7, 5.0 Hz, 2H), 6.86 (dd, J=8.9, 1.9 Hz, 1H), 4.13 (d, J=5.5 Hz, 2H), 3.58 (s, 3H).

Example 31: 2-(7-(2,4-dichlorophenoxy)-4-hydroxy-1-methyl-2-oxo-1,2-dihydroquinoline-3-carboxamido)acetic acid

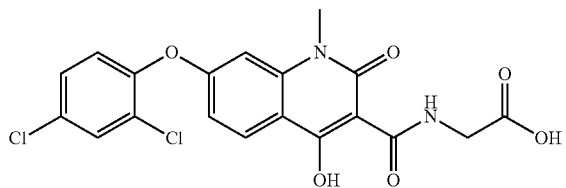 [SMILES: Cn1c(=O)c(C(=O)NCC(=O)O)c(O)c2ccc(Oc3ccc(Cl)cc3Cl)cc21]

Step 1: methyl 7-(2,4-dichlorophenoxy)-4-hydroxy-1-methyl-2-oxo-1,2-dihydroquinoline-3-carboxylate To a two-neck flask were added methyl 7-bromo-4-hydroxy-1-methyl-2-oxo-1,2-dihydroquinoline-3-carboxylate (500 mg, 1.60 mmol), 2,4-difluorophenol (353 mg, 2.17 mmol), cuprous iodide (61 mg, 0.320 mmol), N,N-dimethylglycine (67 mg, 0.650 mmol), cesium carbonate (1.30 g, 4.00 mmol) and dimethyl sulfoxide (15 mL) in turn under nitrogen protection. The mixture was stirred at 140° C. for 20 h. The mixture was cooled to room temperature and acidified with diluted hydrochloric acid (1 M) to pH 3, and the resulting mixture was extracted with ethyl acetate (30 mL×3). The combined organic layers were washed successively with water (50 mL×2) and saturated brine (50 mL), dried over anhydrous sodium sulfate, and filtered. The filtrate was concentrated in vacuo to remove the solvent. The residue was purified by column chromatography (petroleum ether/ethyl acetate (v/v)=1/1) to give a light yellow solid (150 mg, 23.8%).

MS (ESI, pos.ion) m/z: 394.1 (M+1).

Step 2: 2-(7-(2,4-dichlorophenoxy)-4-hydroxy-1-methyl-2-oxo-1,2-dihydroquinoline-3-carboxamido)acetic acid To a solution of methyl 7-(2,4-dichlorophenoxy)-4-hydroxy-1-methyl-2-oxo-1,2-dihydroquinoline-3-carboxylate (78 mg, 0.198 mmol) in ethylene glycol monomethyl ether (20 mL) was added sodium glycinate (100 mg, 1.03 mmol). The mixture was stirred at 130° C. for 3 h. The mixture was cooled to room temperature and concentrated in vacuo to remove the solvent. To the residue was added water (20 mL) and the mixture was acidified with hydrochloric acid (1 M) to pH 3. The resulting mixture was extracted with ethyl acetate (15 mL×3), and the combined organic layers were washed with saturated brine (30 mL), dried over anhydrous sodium sulfate, and filtered. The filtrate was concentrated in vacuo to give a light yellow solid (35 mg, 40.5%).

MS (ESI, pos.ion) m/z: 437.1 (M+1);
$^1$H NMR (400 MHz, DMSO-$d_6$) δ (ppm): 12.92 (s, 1H), 10.44 (s, 1H), 7.94 (d, J=83.7 Hz, 2H), 7.62-7.08 (m, 3H), 6.83 (s, 1H), 4.12 (s, 2H), 3.54 (s, 3H).

Example 32: 2-(7-(2,6-dichlorophenoxy)-4-hydroxy-1-methyl-2-oxo-1,2-dihydroquinoline-3-carboxamido)acetic acid

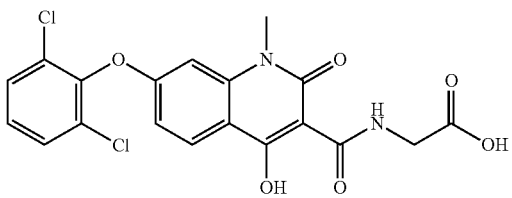

Step 1: methyl 7-(2,6-dichlorophenoxy)-4-hydroxy-1-methyl-2-oxo-1,2-dihydroquinoline-3-carboxylate To a two-neck flask were added methyl 7-bromo-4-hydroxy-1-methyl-2-oxo-1,2-dihydroquinoline-3-carboxylate (5.00 g, 16.0 mmol), 2,6-dichlorophenol (3.50 g, 21.5 mmol), cuprous iodide (1.30 g, 6.83 mmol), N,N-dimethylglycine (1.10 g, 10.7 mmol), cesium carbonate (13.5 g, 41.4 mmol) and dimethyl sulfoxide (200 mL) in turn under nitrogen protection. The mixture was stirred at 140° C. for 20 h. The mixture was cooled to room temperature and acidified with diluted hydrochloric acid (1 M) to pH 4, and the resulting mixture was extracted with dichloromethane (100 mL×3). The combined organic layers were washed successively with water (100 mL×2) and saturated brine (100 mL), dried over anhydrous sodium sulfate, and filtered. The filtrate was concentrated in vacuo to remove the solvent, and the residue was purified by preparative chromatography to give a white solid (73 mg, 1.16%).

MS (ESI, pos.ion) m/z: 393.8 (M+1).

Step 2: 2-(7-(2,6-dichlorophenoxy)-4-hydroxy-1-methyl-2-oxo-1,2-dihydroquinoline-3-carboxamido) acetic acid A mixture of methyl 7-(2,6-dichlorophenoxy)-4-hydroxy-1-methyl-2-oxo-1,2-dihydroquinoline-3-carboxylate (73 mg, 0.185 mmol) and sodium glycinate (40 mg, 0.412 mmol) in ethylene glycol monomethyl ether (10 mL) was refluxed for 2 h. The mixture was cooled to room temperature and concentrated in vacuo to remove the solvent. To the residue was added water (10 mL) and the mixture was acidified with diluted hydrochloric acid (1 M) to pH 4, then the resulting mixture was filtered. The filter cake was washed with water and dried to give a yellow solid (30 mg, 37.05%).

MS (ESI, pos.ion) m/z: 437.2 (M+1);
$^1$H NMR (400 MHz, DMSO-$d_6$) δ (ppm): 10.46 (t, J=5.3 Hz, 1H), 8.07 (d, J=8.9 Hz, 1H), 7.71 (d, J=8.2 Hz, 2H), 7.45 (t, J=8.2 Hz, 1H), 7.21 (d, J=1.9 Hz, 1H), 6.66 (dd, J=8.9, 2.1 Hz, 1H), 4.13 (d, J=5.5 Hz, 2H), 3.58 (s, 3H).

Example 33: 2-(7-(3,4-dichlorophenoxy)-4-hydroxy-1-methyl-2-oxo-1,2-dihydroquinoline-3-carboxamido)acetic acid

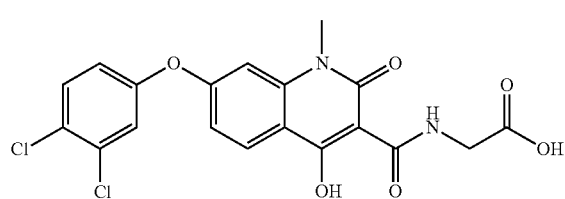 [SMILES: Cn1c(=O)c(C(=O)NCC(=O)O)c(O)c2ccc(Oc3ccc(Cl)c(Cl)c3)cc21]

Step 1: methyl 7-(3,4-dichlorophenoxy)-4-hydroxy-1-methyl-2-oxo-1,2-dihydroquinoline-3-carboxylate To a two-neck flask were added methyl 7-bromo-4-hydroxy-1-methyl-2-oxo-1,2-dihydroquinoline-3-carboxylate (0.500 g, 1.60 mmol), 3,4-dichlorophenol (0.340 g, 2.09 mmol), cuprous iodide (0.061 g, 0.32 mmol), N,N-dimethylglycine (0.050 g, 0.48 mmol), cesium carbonate (1.30 g, 3.99 mmol) and dimethyl sulfoxide (10 mL) in turn under nitrogen protection. The mixture was stirred at 140° C. for 18 h. The mixture was cooled to room temperature and acidified with diluted hydrochloric acid (1 M) to pH 4, and the resulting mixture was extracted with ethyl acetate (50 mL×2). The combined organic layers were washed successively with water (50 mL) and saturated brine (50 mL), dried over anhydrous sodium sulfate, and filtered. The filtrate was concentrated in vacuo to remove the solvent. The residue was purified by column chromatography (petroleum ether/ethyl acetate (v/v)=1/2) to give a white solid (262 mg, 41.5%).

MS (ESI, pos.ion) m/z: 394.2 (M+1).

Step 2: 2-(7-(3,4-dichlorophenoxy)-4-hydroxy-1-methyl-2-oxo-1,2-dihydroquinoline-3-carboxamido) acetic acid The mixture of methyl 7-(3,4-dichlorophenoxy)-4-hydroxy-1-methyl-2-oxo-1,2-dihydroquinoline-3-carboxylate (0.262 g, 0.665 mmol) and sodium glycinate (0.130 g, 1.34 mmol) in ethylene glycol monomethyl ether (10 mL) was refluxed for 2 h. The mixture was cooled to room temperature and filtered. The filter cake was dissolved in water (20 mL), and the mixture was acidified with diluted hydrochloric acid (1 M) to pH 3, then the resulting mixture was filtered. The filter cake was washed with water and dried, then recrystallized from ethyl acetate/petrol ether ((v/v)=1/3) to give a white solid (250 mg, 86.0%).

MS (ESI, pos.ion) m/z: 437.2 (M+1);
$^1$H NMR (400 MHz, DMSO-$d_6$) δ (ppm): 10.48 (s, 1H), 8.12 (d, J=8.5 Hz, 1H), 7.71 (d, J=8.6 Hz, 1H), 7.53 (s, 1H), 7.29 (s, 1H), 7.21 (d, J=8.9 Hz, 1H), 7.01 (d, J=9.3 Hz, 1H), 4.07 (d, J=4.5 Hz, 2H), 3.57 (s, 3H).

Example 34: 2-(7-(3,5-dichlorophenoxy)-4-hydroxy-1-methyl-2-oxo-1,2-dihydroquinoline-3-carboxamido)acetic acid

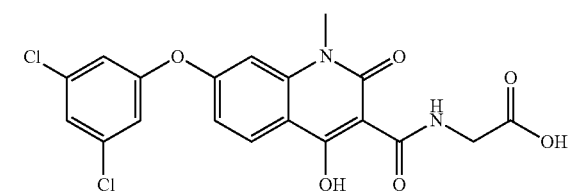 [SMILES: Cn1c(=O)c(C(=O)NCC(=O)O)c(O)c2ccc(Oc3cc(Cl)cc(Cl)c3)cc21]

Step 1: methyl 7-(3,5-dichlorophenoxy)-4-hydroxy-1-methyl-2-oxo-1,2-dihydroquinoline-3-carboxylate To a three-neck flask were added 3,5-dichlorophenol (800 mg, 4.91 mmol), methyl 7-bromo-4-hydroxy-1-methyl-2-oxo-1,2-dihydroquinoline-3-carboxylate (1.00 g, 3.20 mmol), N,N-dimethylglycine (100 mg, 0.970 mmol), cuprous iodide (130 mg, 0.683 mmol), cesium carbonate (2.60 g, 7.98 mmol) and dimethyl sulfoxide (50 mL) in turn under nitrogen protection. The mixture was stirred at 140° C. for 20 h. The mixture was cooled to room temperature and acidified with hydrochloric acid (1 M) to pH 3. To the mixture was added water (20 mL), and the resulting mixture was extracted with ethyl acetate (25 mL×3). The combined organic layers were washed with water (30 mL×2) and saturated brine (50 mL), dried over anhydrous sodium sulfate, and filtered. The filtrate was concentrated in vacuo to remove the solvent. The residue was purified by column chromatography (petroleum ether/ethyl acetate (v/v)=4/1) to give a white solid (166 mg, 13.1%).

MS (ESI, pos.ion) m/z: 393.8 (M+1).

Step 2: 2-(7-(3,5-dichlorophenoxy)-4-hydroxy-1-methyl-2-oxo-1,2-dihydroquinoline-3-carboxamido)acetic acid To a solution of methyl 7-(3,5-dichlorophenoxy)-4-hydroxy-1-methyl-2-oxo-1,2-dihydroquinoline-3-carboxylate (166 mg, 0.421 mmol) in ethylene glycol monomethyl ether (20 mL) was added sodium glycinate (80 mg, 0.824 mmol). The mixture was stirred at 130° C. for 2 h. The mixture was cooled to room temperature and concentrated in vacuo to remove the solvent. To the residue was added water (15 mL) and the mixture was acidified with diluted hydrochloric acid (1 M) to pH 4. The resulting mixture was extracted with EtOAc (20 mL×3). The combined organic layers were washed with saturated brine (45 mL), dried over anhydrous sodium sulfate, and filtered. The filtrate was concentrated in vacuo to give a white solid (100 mg, 54.3%).

MS (ESI, pos.ion) m/z: 437.1 (M+1);
$^1$H NMR (400 MHz, DMSO-$d_6$) δ (ppm): 12.93 (s, 1H), 10.47 (t, J=5.3 Hz, 1H), 8.12 (d, J=8.8 Hz, 1H), 7.49 (s, 1H), 7.37-7.25 (m, 3H), 7.03 (dd, J=8.8, 1.7 Hz, 1H), 4.14 (d, J=5.5 Hz, 2H), 3.58 (s, 3H).

Example 35: 2-(7-(2,5-dichlorophenoxy)-4-hydroxy-1-methyl-2-oxo-1,2-dihydroquinoline-3-carboxamido)acetic acid

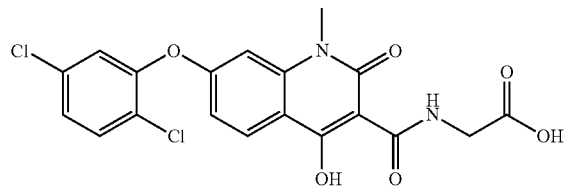 [SMILES: Cn1c(=O)c(C(=O)NCC(=O)O)c(O)c2ccc(Oc3cc(Cl)ccc3Cl)cc21]

Step 1: methyl 7-(2,5-dichlorophenoxy)-4-hydroxy-1-methyl-2-oxo-1,2-dihydroquinoline-3-carboxylate To a three-neck flask were added 2,5-dichlorophenol (1.60 g, 9.80 mmol), methyl 7-bromo-4-hydroxy-1-methyl-2-oxo-1,2-dihydroquinoline-3-carboxylate (2.00 g, 6.41 mmol), N,N-dimethylglycine (270 mg, 2.62 mmol), cuprous iodide (245 mg, 1.29 mmol), cesium carbonate (5.30 g, 16.0 mmol) and dimethyl sulfoxide (50 mL) in turn under nitrogen protection. The mixture was stirred at 140° C. for 36 h. The mixture was acidified with hydrochloric acid (1 M) to pH 3. To the mixture was added water (20 mL), and the resulting mixture was extracted with ethyl acetate (25 mL×3). The combined organic layers were washed successively with water (30 mL×3) and saturated brine (50 mL), dried over anhydrous sodium sulfate, and filtered. The filtrate was concentrated in vacuo to remove the solvent. The residue was purified by column chromatography (petroleum ether/ethyl acetate (v/v)=1/1) to give a red solid (700 mg, 27.7%).

MS (ESI, pos.ion) m/z: 394.1 (M+1).

Step 2: 2-(7-(2,5-dichlorophenoxy)-4-hydroxy-1-methyl-2-oxo-1,2-dihydroquinoline-3-carboxamido)acetic acid To a solution of methyl 7-(2,5-dichlorophenoxy)-4-hydroxy-1-methyl-2-oxo-1,2-dihydroquinoline-3-carboxylate (240 mg, 0.609 mmol) in ethylene glycol monomethyl ether (25 mL) was added sodium glycinate (300 mg, 3.09 mmol). The mixture was stirred at 130° C. for 3 h. The mixture was cooled to room temperature and concentrated in vacuo to remove the solvent. To the residue was added water (15 mL), and the mixture was acidified with diluted hydrochloric acid (1 M) to pH 3, and the resulting mixture was extracted with ethyl acetate (20 mL×3). The combined organic layers were washed successively with saturated brine (45 mL), dried over anhydrous sodium sulfate. The filtrate was concentrated in vacuo to remove the solvent and give a light yellow solid (130 mg, 48.8%).

MS (ESI, pos.ion) m/z: 436.7 (M+1);
$^1$H NMR (400 MHz, DMSO-$d_6$) δ (ppm): 12.93 (s, 1H), 10.47 (s, 1H), 8.10 (d, J=8.8 Hz, 1H), 7.72 (d, J=8.6 Hz, 1H), 7.50-7.37 (m, 2H), 7.27 (s, 1H), 6.93-6.82 (m, 1H), 4.12 (s, 2H), 3.58 (s, 3H).

Example 36: 2-(4-hydroxy-7-(4-methoxyphenoxy)-1-methyl-2-oxo-1,2-dihydroquinoline-3-carboxamido)acetic acid

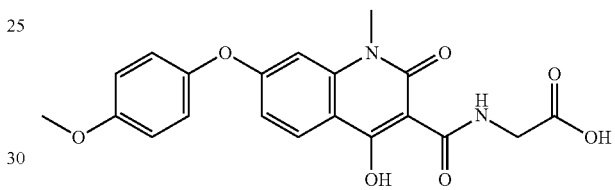

Step 1: methyl 4-hydroxy-7-(4-methoxyphenoxy)-1-methyl-2-oxo-1,2-dihydroquinoline-3-carboxylate To a three-neck flask were added methyl 7-bromo-4-hydroxy-1-methyl-2-oxo-1,2-dihydroquinoline-3-carboxylate (500 mg, 1.60 mmol), cuprous iodide (61.0 mg, 0.320 mmol), (1R,2R)—$N^1$,$N^2$-dimethyl cyclohexane-1,2-diamine (101 μL, 0.640 mmol), 4-methoxyphenol (0.298 g, 2.40 mmol), cesium carbonate (1.30 g, 4.00 mmol) and N,N-dimethylformamide (15 mL) in turn under nitrogen protection. The mixture was stirred at 130° C. for 12 h. The mixture was cooled to room temperature and quenched with water (40 mL). The mixture was acidified with diluted hydrochloric acid (2 M) to pH 3, and the resulting mixture was extracted with ethyl acetate (100 mL×2). The combined organic layers were washed successively with water (20 mL) and saturated brine (20 mL), dried over anhydrous sodium sulfate, and filtered. The filtrate was concentrated. The residue was purified by column chromatography (petroleum ether/ethyl acetate (v/v)=2/1) to give a white solid (275 mg, 48.3%).

MS (ESI, pos.ion) m/z: 355.9 (M+1).

Step 2: 2-(4-hydroxy-7-(4-methoxyphenoxy)-1-methyl-2-oxo-1,2-dihydroquinoline-3-carboxamido)acetic acid To a solution of methyl 4-hydroxy-7-(4-methoxyphenoxy)-1-methyl-2-oxo-1,2-dihydroquinoline-3-carboxylate (275 mg, 0.774 mmol) in ethylene glycol monomethyl ether (10 mL) was added sodium glycinate (0.150 g, 1.55 mmol). The mixture was refluxed for 3 h. The mixture was cooled to room temperature and concentrated in vacuo to remove the solvent. The residue was dissolved in water (20 mL), and the mixture was acidified with hydrochloric acid (1 M) to pH 4. The resulting mixture was filtered and the filter cake was washed with water, then dried in oven to give a white solid (220 mg, 71.3%).

MS (ESI, neg. ion) m/z: 397.05 (M−1);

¹H NMR (400 MHz, DMSO-d₆) δ (ppm): 10.46 (t, J=5.5 Hz, 1H), 8.04 (d, J=8.9 Hz, 1H), 7.16 (d, J=9.0 Hz, 2H), 7.06 (dd, J=17.4, 5.5 Hz, 3H), 6.82 (dd, J=8.9, 2.1 Hz, 1H), 4.12 (d, J=5.5 Hz, 2H), 3.79 (s, 3H), 3.53 (s, 3H).

Example 37: 2-(4-hydroxy-7-(3-methoxyphenoxy)-1-methyl-2-oxo-1,2-dihydroquinoline-3-carboxamido)acetic acid

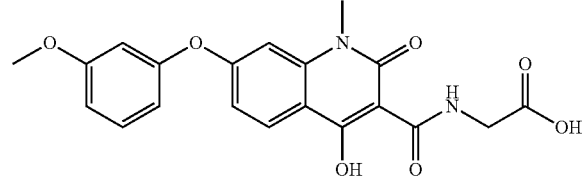 [SMILES: COc1cccc(Oc2ccc3c(O)c(C(=O)NCC(=O)O)c(=O)n(C)c3c2)c1]

Step 1: methyl 4-hydroxy-7-(3-methoxyphenoxy)-1-methyl-2-oxo-1,2-dihydroquinoline-3-carboxylate To a two-neck round bottom flask were added methyl 7-bromo-4-hydroxy-1-methyl-2-oxo-1,2-dihydroquinoline-3-carboxylate (500 mg, 1.60 mmol), 3-methoxyphenol (300 mg, 2.42 mmol), cesium carbonate (1.31 g, 4.00 mmol), cuprous iodide (62.0 mg, 0.326 mmol), N,N-dimethylglycine (70 mg, 0.679 mmol) and dimethyl sulfoxide (15 mL) in turn under nitrogen protection. The mixture was stirred at 140° C. overnight. The mixture was cooled to room temperature and acidified with diluted hydrochloric acid (2 M) to pH 3, and the resulting mixture was extracted with ethyl acetate (25 mL×3). The combined organic layers were washed with water (20 mL×2) and saturated brine (40 mL), dried over anhydrous sodium sulfate, and filtered. The filtrate was concentrated in vacuo to remove the solvent. The residue was purified by column chromatography (petroleum ether/ethyl acetate (v/v)=1/1) to give a red solid (341 mg, 59.9%).

MS (ESI, pos.ion) m/z: 355.9 (M+1).

Step 2: 2-(4-hydroxy-7-(3-methoxyphenoxy)-1-methyl-2-oxo-1,2-dihydroquinoline-3 carboxamido)acetic acid To a solution of methyl 4-hydroxy-7-(3-methoxyphenoxy)-1-methyl-2-oxo-1,2-dihydroquinoline-3-carboxylate (341 mg, 0.960 mmol) in ethylene glycol monomethyl ether (30 mL) was added sodium glycinate (200 mg, 2.061 mmol). The mixture was stirred at 130° C. for 3 h under nitrogen protection. The mixture was cooled to room temperature and concentrated in vacuo to remove the solvent. To the residue was added water (25 mL), and the mixture was washed with ethyl acetate (15 mL×3). The aqueous layer was acidified with hydrochloric acid (1 M) to pH 4, and the resulting mixture was extracted with ethyl acetate (25 mL×3). The combined organic layers were washed with saturated brine (30 mL), dried over anhydrous sodium sulfate, and filtered. The filtrate was concentrated in vacuo to give a yellow solid (370 mg, 96.8%).

MS (ESI, pos.ion) m/z: 399.2 (M+1);

¹H NMR (400 MHz, DMSO-d₆) δ (ppm): 12.88 (s, 1H), 10.46 (t, J=5.3 Hz, 1H), 8.05 (d, J=8.9 Hz, 1H), 7.38 (t, J=8.2 Hz, 1H), 7.17 (s, 1H), 6.94-6.80 (m, 2H), 6.80-6.68 (m, 2H), 4.13 (d, J=5.4 Hz, 2H), 3.77 (s, 3H), 3.54 (s, 3H).

Example 38: 2-(4-hydroxy-7-(2-methoxyphenoxy)-1-methyl-2-oxo-1,2-dihydroquinoline-3-carboxamido)acetic acid

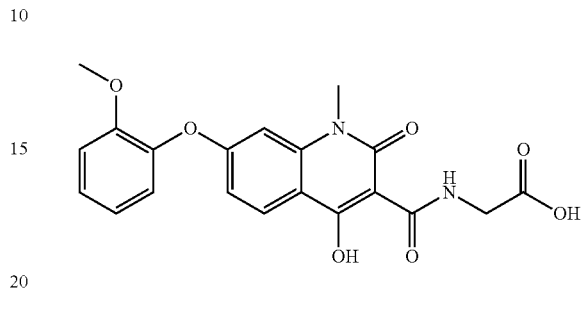

Step 1: methyl 4-hydroxy-7-(2-methoxyphenoxy)-1-methyl-2-oxo-1,2-dihydroquinoline-3-carboxylate To a two-neck round-bottom flask were added methyl 7-bromo-4-hydroxy-1-methyl-2-oxo-1,2-dihydroquinoline-3-carboxylate (500 mg, 1.60 mmol), guaiacol (0.298 g, 2.40 mmol), cesium carbonate (1.30 g, 4.00 mmol), cuprous iodide (61.0 mg, 0.320 mmol), trans-N,N'-dimethyl-1,2-cyclopentanediamine (28 mg, 0.27 mmol) and N,N-dimethylglycine (15 mL) in turn under nitrogen protection. The mixture was stirred at 130° C. for 24 h. The mixture was cooled to room temperature and acidified with diluted hydrochloric acid (2 M) to pH 3, and the resulting mixture was extracted with ethyl acetate (25 mL×3). The combined organic layers were washed successively with water (20 mL×2) and saturated brine (40 mL), dried over anhydrous sodium sulfate, and filtered. The filtrated was concentrated in vacuo to remove the solvent. The residue was purified by column chromatography (petroleum ether/ethyl acetate (v/v)=2/1) to give a yellow solid (150 mg, 26.4%).

MS (ESI, pos.ion) m/z: 356.25 (M+1).

Step 2: 2-(4-hydroxy-7-(2-methoxyphenoxy)-1-methyl-2-oxo-1,2-dihydroquinoline-3-carboxamido) acetic acid To a solution of methyl 4-hydroxy-7-(2-methoxyphenoxy)-1-methyl-2-oxo-1,2-dihydroquinoline-3-carboxylate (150 mg, 0.422 mmol) in ethylene glycol monomethyl ether (10 mL) was added sodium glycinate (81.0 mg, 0.835 mmol). The mixture was stirred at 130° C. for 3 h under nitrogen protection. The mixture was cooled to room temperature and concentrated in vacuo to remove the solvent. To the residue was added water (25 mL), and the mixture was washed with ethyl acetate (15 mL×3). The aqueous layer was acidified with hydrochloric acid (1 M) to pH 4, and the resulting mixture was extracted with ethyl acetate (25 mL×3). The combined organic layers were washed with saturated brine (30 mL), dried over anhydrous sodium sulfate, and filtered. The filtrate was concentrated in vacuo to remove the solvent and give a beige solid (25.0 mg, 14.9%).

MS (ESI, pos.ion) m/z: 398.85 (M+1);

¹H NMR (600 MHz, DMSO-d₆) δ (ppm): 10.48 (t, J=5.5 Hz, 1H), 8.03 (d, J=8.9 Hz, 1H), 7.37-7.29 (m, 1H), 7.28-

7.18 (m, 2H), 7.10-7.02 (m, 2H), 6.74-6.67 (m, 1H), 4.13 (d, J=5.6 Hz, 2H), 3.75 (s, 3H), 3.54 (s, 3H).

Example 39: 2-(6-fluoro-4-hydroxy-1-methyl-2-oxo-7-phenoxy-1,2-dihydroquinoline-3-carboxamido)acetic acid

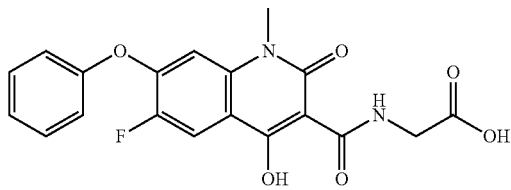 [SMILES: Cn1c(=O)c(C(=O)NCC(=O)O)c(O)c2cc(F)c(Oc3ccccc3)cc21]

Step 1) 2-amino-4-bromo-5-fluorobenzoic acid

Methyl 2-amino-4-bromo-5-fluorobenzoate (6.20 g, 25.0 mmol) and sodium hydroxide (5.00 g, 125 mmol) were dissolved in a mixed solvent of tetrahydrofuran/methanol/water (100 mL, v/v/v=1/1/1). The mixture was stirred at room temperature overnight. The mixture was concentrated in vacuo to remove the solvent. The residue was dissolved in water (50 mL), and the mixture was acidified with diluted hydrochloric acid (1 M) to pH 4, then the resulting mixture was filtered. The filter cake was washed with water and dried in vacuo to give a white solid (5.75 g, 98.3%).
MS (ESI, pos.ion) m/z: 234.1 (M+1).

Step 2: 7-bromo-6-fluoro-1H-benzo[d][1,3]oxazine-2,4-dione

To a solution of 2-amino-4-bromo-5-fluorobenzoic acid (2.70 g, 12.0 mmol) in tetrahydrofuran (10 mL) was added triphosgene (2.00 g, 6.74 mmol). The mixture was refluxed overnight. The mixture was cooled to room temperature and to the mixture was added water (10 mL), then there was a solid precipitated out. The mixture was filtered, and the filter cake was dried in oven to give a white solid (2.90 g, 97.0%).
MS (ESI, pos.ion) m/z: 259.8 (M+1).

Step 3: 7-bromo-6-fluoro-1-methyl-1H-benzo[d][1,3]oxazine-2,4-dione

To a two-neck flask were added sodium hydride (600 mg, 15.0 mmol), N,N-dimethylformamide (30 mL) and 7-bromo-6-fluoro-1H-benzo[d][1,3]oxazine-2,4-dione (2.90 g, 11.0 mmol). The mixture was stirred at room temperature for 30 min, then iodomethane (0.80 mL, 13.0 mmol) was added. Then the resulting mixture was stirred for 18 h at rt. To the mixture was added water (50 mL), and there was a solid precipitated out, then the mixture was filtered. The filter cake was washed with water (20 mL) and methyl tert-butyl ether (10 mL) in turn, then dried in vacuo to give a white solid (2.00 g, 65.0%).
MS (ESI, pos.ion) m/z: 273.8 (M+1).

Step 4: methyl 7-bromo-6-fluoro-4-hydroxy-1-methyl-2-oxo-1,2-dihydroquinoline-3-carboxylate To a solution of 7-bromo-6-fluoro-1-methyl-1H-benzo[d][1,3]oxazine-2,4-dione (1.57 g, 4.76 mmol) in N,N-dimethylformamide (50 mL) were added dimethyl malonate (1.30 mL, 11.4 mmol) and a solution of sodium tert-butoxide (1.15 g, 11.6 mmol) in N,N-dimethylformamide (10 mL). The mixture was stirred at 95° C. for 1 h. The mixture was cooled to room temperature and acidified with diluted hydrochloric acid (2 M) to pH 4, then water (20 mL) was added. Then there was a solid precipitated out, and the mixture was filtered. The filter cake was washed with water and dried to give a light yellow solid (1.57 g, 84.1%).
MS (ESI, pos.ion) m/z: 329.8 (M+1).

Step 5: methyl 6-fluoro-4-hydroxy-1-methyl-2-oxo-7-phenoxy-1,2-dihydroquinoline-3-carboxylate To a two-neck flask were added methyl 7-bromo-6-fluoro-4-hydroxy-1-methyl-2-oxo-1,2-dihydroquinoline-3-carboxylate (1.57 g, 4.76 mmol), phenol (0.60 mL, 6.80 mmol), cuprous iodide (190 mg, 0.99 mmol), N,N-dimethylglycine (200 mg, 1.94 mmol), cesium carbonate (3.88 g, 11.9 mmol) and dimethyl sulfoxide (50 mL) in turn under nitrogen protection. The mixture was stirred at 140° C. for 20 h. The mixture was cooled to room temperature and acidified with diluted hydrochloric acid (1 M) to pH 4, and the resulting mixture was extracted with dichloromethane (50 mL×2). The combined organic layers were washed successively with water (50 mL) and saturated brine (50 mL), dried over anhydrous sodium sulfate, and filtered. The filtrate was concentrated in vacuo, and the residue was purified by preparative chromatography to give a white solid (124 mg, 7.59%).
MS (ESI, pos.ion) m/z: 344.2 (M+1).

Step 6: 2-(6-fluoro-4-hydroxy-1-methyl-2-oxo-7-phenoxy-1,2-dihydroquinoline-3-carboxamido)acetic acid A mixture of methyl 6-fluoro-4-hydroxy-1-methyl-2-oxo-7-phenoxy-1,2-dihydroquinoline-3-carboxylate (124 mg, 0.361 mmol) and sodium glycinate (70 mg, 0.721 mmol) in ethylene glycol monomethyl ether (20 mL) was refluxed for 2 h. The mixture was cooled to room temperature and filtered. The filter cake was dissolved in water (20 mL), and the mixture was acidified with diluted hydrochloric acid (1 M) to pH 4, then the resulting mixture was filtered. The filter cake was washed with water and dried to give a white solid (75 mg, 53.8%).
MS (ESI, pos.ion) m/z: 387.2 (M+1);
$^1$H NMR (400 MHz, DMSO-$d_6$) δ (ppm): 10.48 (s, 1H), 7.95 (d, J=10.8 Hz, 1H), 7.46 (t, J=7.8 Hz, 2H), 7.33-7.20 (m, 2H), 7.16 (d, J=8.1 Hz, 2H), 4.14 (d, J=5.4 Hz, 2H), 3.49 (s, 3H).

Example 40: 2-(4-hydroxy-1-methyl-2-oxo-7-(2-(trifluoromethoxy)phenoxy)-1,2-dihydroquinoline-3-carboxamido)acetic acid

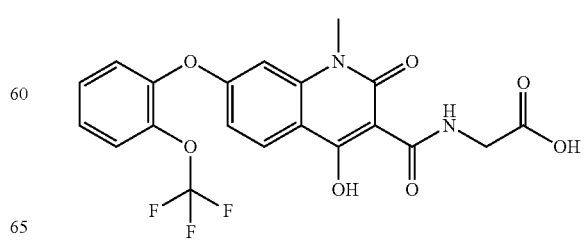

Step 1: methyl 4-hydroxy-1-methyl-2-oxo-7-(2-(trifluoromethoxy)phenoxy)-1,2-dihydroquinoline-3-carboxylate To a three-neck flask were added methyl 7-bromo-4-hydroxy-1-methyl-2-oxo-1,2-dihydroquinoline-3-carboxylate (1.03 g, 3.30 mmol), 2-(trifluoromethoxy)phenol (0.92 g, 5.16 mmol), cesium carbonate (2.10 g, 6.45 mmol), N,N-dimethylglycine (0.13 g, 1.26 mmol), cuprous iodide (0.125 g, 0.656 mmol) and N,N-dimethylformamide (50 mL) in turn under nitrogen protection. The mixture was stirred at 140° C. for 20 h. Then the mixture was cooled to room temperature and filtered. The filter cake was washed with ethyl acetate (50 mL). The collected filtrates were concentrated in vacuo to remove the solvent. The residue was purified by column chromatography (petroleum ether/ethyl acetate (v/v)=3/1) to give a yellow solid (0.95 g, 70.0%).

MS (ESI, pos.ion) m/z: 410.2 (M+1).

Step 2: 2-(4-hydroxy-1-methyl-2-oxo-7-(2-(trifluoromethoxy)phenoxy)-1,2-dihydroquinoline-3-carboxamido)acetic acid To a solution of methyl 4-hydroxy-1-methyl-2-oxo-7-(2-(trifluoromethoxy) phenoxy)-1,2-dihydroquinoline-3-carboxylate (0.95 g, 2.30 mmol) in methyl tert-butyl ether (50 mL) was added sodium glycinate (0.51 g, 5.3 mmol). The mixture was stirred at 130° C. for 5 h. The mixture was filtered while hot, and the filter cake was washed with ethyl acetate (50 mL). The filter cake was dissolved in water (20 mL), and the mixture was extracted with ethyl acetate (20 mL×2). The combined organic layers were dried over anhydrous sodium sulfate and filtered. The filtrate was concentrated in vacuo to remove the solvent and give a white solid (0.56 g, 53.0%).

MS (ESI, pos.ion) m/z: 453.2 (M+1);
$^1$H NMR (400 MHz, DMSO-d$_6$) δ (ppm): 12.95 (s, 1H), 10.47 (t, J=5.4 Hz, 1H), 8.11 (d, J=8.9 Hz, 1H), 7.62 (d, J=8.0 Hz, 1H), 7.51 (td, J=7.9, 1.4 Hz, 1H), 7.46-7.33 (m, 2H), 7.24 (d, J=2.0 Hz, 1H), 6.88 (dd, J=8.9, 2.1 Hz, 1H), 4.13 (d, J=5.5 Hz, 2H), 3.57 (s, 3H).

Example 41: 2-(4-hydroxy-7-(3-hydroxyphenoxy)-1-methyl-2-oxo-1,2-dihydroquinoline-3-carboxamido)acetic acid

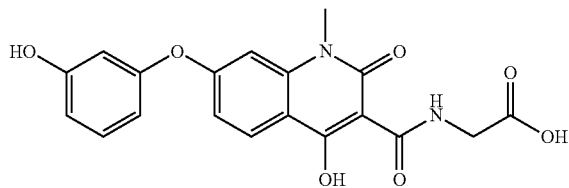 [SMILES: Cn1c(=O)c(C(=O)NCC(=O)O)c(O)c2ccc(Oc3cccc(O)c3)cc21]

Step 1: methyl 4-hydroxy-7-(3-hydroxyphenoxy)-1-methyl-2-oxo-1,2-dihydroquinoline-3-carboxylate To a mixture of methyl 7-bromo-4-hydroxy-1-methyl-2-oxo-1,2-dihydroquinoline-3-carboxylate (1.02 g, 3.27 mmol), resorcinol (1.07 g, 9.72 mmol), cesium carbonate (2.12 g, 6.51 mmol), N,N-dimethylglycine (0.135 g, 1.30 mmol) and cuprous iodide (0.12 g, 0.63 mmol) was added N,N-dimethylformamide (50 mL) under nitrogen protection. The mixture was stirred at 140° C. for 20 h. The mixture was filtered, and the filter cake was washed with ethyl acetate (50 mL). The combined filtrates were concentrated by spin steaming instrument. The residue was purified by chromatography eluted with dichloromethane/methanol ((v/v)=20/1) to give a yellow solid (0.91 g, 82.0%).

MS (ESI, pos.ion) m/z: 341.9 (M+1).

Step 2: 2-(4-hydroxy-7-(3-hydroxyphenoxy)-1-methyl-2-oxo-1,2-dihydroquinoline-3-carboxamido)acetic acid To a solution of methyl 4-hydroxy-7-(3-hydroxyphenoxy)-1-methyl-2-oxo-1,2-dihydroquinoline-3-carboxylate (0.91 g, 2.70 mmol) in methyl tert-butyl ether (50 mL) was added sodium glycinate (0.578 g, 5.96 mmol). The mixture was stirred at 130° C. for 5 h. Then the resulting mixture was filtered while hot. The filter cake was washed with ethyl acetate (10 mL) and dried to give a white solid (0.23 g, 22.0%).

MS (ESI, pos.ion) m/z: 384.8 (M+1);
$^1$H NMR (400 MHz, DMSO-d$_6$) δ (ppm): 12.89 (s, 1H), 10.47 (t, J=5.5 Hz, 1H), 9.76 (s, 1H), 8.08 (d, J=8.9 Hz, 1H), 7.25 (t, J=8.1 Hz, 1H), 7.19 (d, J=2.0 Hz, 1H), 6.90 (dd, J=8.9, 2.1 Hz, 1H), 6.66 (dd, J=8.2, 1.5 Hz, 1H), 6.58 (dd, J=7.8, 1.8 Hz, 1H), 6.53 (t, J=2.2 Hz, 1H), 4.13 (d, J=5.6 Hz, 2H), 3.56 (s, 3H).

Example 42: 2-(1-(cyclopropylethyl)-4-hydroxy-2-oxo-7-phenoxy-1,2-dihydroquinoline-3-carboxamido)acetic acid

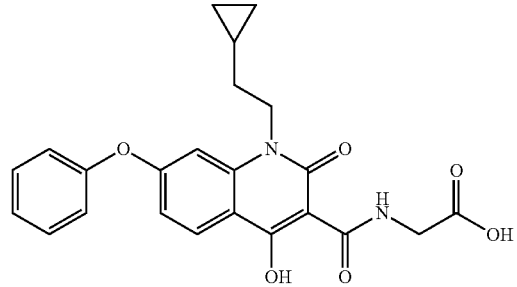 [SMILES: O=C(O)CNC(=O)c1c(O)c2ccc(Oc3ccccc3)cc2n(CCC2CC2)c1=O]

Step 1: 7-bromo-1-(2-cyclopropylethyl)-1H-benzo[d][1,3]oxazine-2,4-dione

To a three-neck flask were added 7-bromo-1H-benzo[d][1,3]oxazine-2,4-dione (2.00 g, 8.26 mmol), 2-cyclopropylethanol (0.870 g, 10.1 mmol), triphenylphosphine (3.25 g, 12.4 mmol) and tetrahydrofuran (60 mL), the mixture was cooled to 0° C., and diisopropyl azodicarboxylate (2.50 mL, 12.7 mmol) was added dropwise. After the addition, the mixture was stirred at room temperature for 4 h. The reaction mixture was concentrated in vacuo to remove the solvent. The residue was purified by column chromatography (petroleum ether/dichloromethane (v/v)=10/1) to give a white solid (2.54 g, 99.11%).

MS (ESI, pos.ion) m/z: 310.2 (M+1).

Step 2: methyl 7-bromo-1-(2-cyclopropylethyl)-4-hydroxy-2-oxo-1,2-dihydroquinoline-3-carboxylate To a solution of dimethyl malonate (2.38 g, 18.0 mmol) in N,N-dimethylformamide (20 mL) was added sodium tert-butoxide (1.73 g, 18.0 mmol). The mixture was stirred for 30 min, then the mixture was added to a solution of 7-bromo-1-(2-cyclopropylethyl)-1H-benzo[d][1,3]oxazine-2,4-dione (2.79 g, 9.00 mmol) in N,N-dimethylformamide (50 mL). The resulting mixture was stirred at 110° C. for 2 h. The mixture was cooled to 0° C. and water (100 mL) was added. The mixture was acidified with diluted hydrochloric acid (1 M) to pH 4, and the resulting mixture was extracted with ethyl acetate (60 mL×3). The combined organic layers were washed successively with water (20 mL×3) and saturated brine (20 mL), dried over anhydrous sodium sulfate, and filtered. The filtrate was concentrated in vacuo to remove the solvent. The residue was purified by column chromatography (EtOAc) to give a white solid (1.78 g, 54.0%).

MS (ESI, pos.ion) m/z: 366.2 (M+1).

Step 3: methyl 1-(2-cyclopropylethyl)-4-hydroxy-2-oxo-7-phenoxy-1,2-dihydroquinoline-3-carboxylate To a three-neck flask were added methyl 7-bromo-1-(2-cyclopropylethyl)-4-hydroxy-2-oxo-1,2-dihydroquinoline-3-carboxylate (1.78 g, 4.86 mmol), phenol (0.731 g, 7.77 mmol), cesium carbonate (3.17 g, 9.72 mmol), N,N-dimethylglycine (0.200 g, 1.94 mmol), cuprous iodide (0.185 g, 0.971 mmol) and N,N-dimethylformamide (15 mL). The mixture was stirred at 140° C. overnight. The mixture was filtered and the filtrate was concentrated in vacuo to remove the solvent. The residue was purified by column chromatography (petroleum ether/ethyl acetate (v/v)=1/2) to give a white solid (1.21 g, 76.5%).

MS (ESI, pos.ion) m/z: 380.4 (M+1).

Step 4: 2-(1-(2-cyclopropyl ethyl)-4-hydroxy-2-oxo-7-phenoxy-1,2-dihydroquinoline-3-carboxamido) acetic acid To a solution of methyl 1-(2-2-cyclopropylethyl)-4-hydroxy-2-oxo-7-phenoxy-1,2-dihydroquinoline-3-carboxylate (1.21 g, 3.19 mmol) in ethylene glycol monomethyl ether (20 mL) was added sodium glycinate (0.495 g, 5.10 mmol). The mixture was refluxed for 3 h. The mixture was cooled to room temperature and concentrated in vacuo to remove the solvent. The residue was dissolved in water (20 mL), and the mixture was washed with ethyl ether (10 mL×2), then acidified with diluted hydrochloric acid (1 M) to pH 4. The resulting mixture was filtered and the filter cake was washed with water, then dried in oven to give a white solid (0.550 g, 40.8%).

MS (ESI, pos.ion) m/z: 423.2 (M+1);
$^1$H NMR (400 MHz, DMSO-$d_6$) δ (ppm): 10.60 (t, J=5.2 Hz, 1H), 8.23 (d, J=8.9 Hz, 1H), 7.65 (t, J=7.9 Hz, 2H), 7.45 (t, J=7.4 Hz, 1H), 7.36 (d, J=7.7 Hz, 2H), 7.17 (s, 1H), 7.10 (dd, J=8.9, 1.9 Hz, 1H), 4.31 (t, 2H), 4.25 (d, J=5.5 Hz, 2H), 1.58 (dd, J=14.9, 7.2 Hz, 2H), 0.87-0.74 (m, 1H), 0.52-0.43 (m, 2H), 0.07-0.00 (m, J=5.0 Hz, 2H).

Example 43: 2-(4-hydroxy-1-methyl-2-oxo-7-(pyridin-4-yloxy)-1,2-dihydroquinoline-3-carboxamido) acetic acid

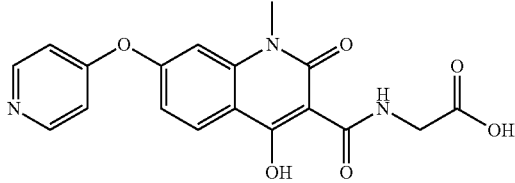 [SMILES: Cn1c(=O)c(C(=O)NCC(=O)O)c(O)c2ccc(Oc3ccncc3)cc21]

Step 1: methyl 4-hydroxy-1-methyl-2-oxo-7-(pyridin-4-yloxy)-1,2-dihydroquinoline-3-carboxylate To a three-neck flask were added methyl 7-bromo-4-hydroxy-1-methoxy-2-oxo-1,2-dihydroquinoline-3-carboxylate (1.00 g, 3.2 mmol), pyridin-4-ol (0.432 g, 4.54 mmol), N,N-dimethylglycine (0.088 g, 0.85 mmol), cuprous iodide (0.082 g, 0.43 mmol), cesium carbonate (2.50 g, 7.67 mmol) and N,N-dimethylformamide (20 mL) in turn under nitrogen protection. The mixture was stirred at 140° C. for 12 h. The mixture was cooled to room temperature and ice-water (40 mL) was added. The mixture was acidified with diluted hydrocloric acid (1 M) to pH 6. The resulting mixture was filtered, and the filter cake was dried to give a white solid (1.05 g, 100%).

MS (ESI, pos.ion) m/z: 327.3 (M+1).

Step 2: 2-(4-hydroxy-1-methyl-2-oxo-7-(pyridin-4-yloxy)-1,2-dihydroquinoline-3-carboxamido)acetic acid To a solution of methyl 4-hydroxy-1-methyl-2-oxo-7-(pyridin-4-yloxy)-1,2-dihydroquinoline-3-carboxylate (1.26 g, 3.86 mmol) in ethylene glycol monomethyl ether (50 mL) was added sodium glycinate (0.749 g, 7.72 mmol). The mixture was refluxed for 4 h. The mixture was cooled to room temperature and filtered. The filter cake was dissolved in water (30 mL), and the mixture was acidified with diluted hydrochloric acid (1 M) to pH 6, then the resulting mixture was filtered. The filter cake was dried in vacuo to give a white solid (0.620 g, 43.5%).

MS (ESI, pos.ion) m/z: 370.1 (M+1);
$^1$H NMR (400 MHz, D$_2$O) δ (ppm): 7.70 (d, J=41.5 Hz, 3H), 6.81 (s, 2H), 6.37 (s, 2H), 3.54 (s, 2H), 3.06 (s, 3H).

Example 44: 2-(4-hydroxy-1-methyl-2-oxo-7-(pyrimidin-5-yloxy)-1,2-dihydroquinoline-3-carboxamido)acetic acid

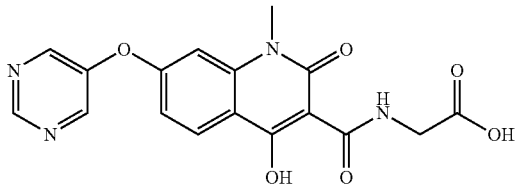 [SMILES: Cn1c(=O)c(C(=O)NCC(=O)O)c(O)c2ccc(Oc3cncnc3)cc21]

Step 1: methyl 4-hydroxy-1-methyl-2-oxo-7-(pyrimidin-5-yloxy)-1,2-dihydroquinoline-3-carboxylate To a three-neck flask were added methyl 7-bromo-4-hydroxy-1-methyl-2-oxo-1,2-dihydroquinoline-3-carboxylate (1.00 g, 3.20 mmol), pyrimidin-5-ol acetic acid salt (0.800 g, 5.12 mmol), N,N-dimethylglycine (0.091 g, 0.88 mmol), cuprous iodide (0.092 g, 0.48 mmol), cesium carbonate (2.50 g, 7.67 mmol) and N,N-dimethylformamide (20 mL) in turn under nitrogen protection. The mixture was stirred at 140° C. for 12 h. The mixture was cooled to room temperature and ice-water (40 mL) was added. The mixture was acidified with diluted hydrocloric acid (1 M) to pH 6. The resulting mixture was filtered, and the filter cake was dried to give a white solid (0.420 g, 40.1%).

MS (ESI, pos.ion) m/z: 328.3 (M+1).

Step 2: 2-(4-hydroxy-1-methyl-2-oxo-7-(pyrimidin-5-yloxy)-1,2-dihydroquinoline-3-carboxamido)acetic acid To a three-neck flask were added methyl 4-hydroxy-1-methyl-2-oxo-7-(pyrimidin-5-yloxy)-1,2-dihydroquinoline-3-carboxylate (0.420 g, 1.28 mmol), sodium glycinate (0.250 g, 2.58 mmol) and ethylene glycol monomethyl ether (15 mL). The mixture was refluxed for 4 h. The mixture was cooled to room temperature and filtered. The filter cake was washed with ethyl acetate and dried in oven, then dissolved in water (30 mL). The mixture was acidified with diluted hydrochloric acid (1 M) to pH 4, then the resulting mixture was filtered. The filter cake was washed with water and dried in oven to give a white solid (0.050 g, 11.0%).

MS (ESI, pos.ion) m/z: 371.3 (M+1);
$^1$H NMR (400 MHz, DMSO-d$_6$) δ (ppm): 10.46 (t, J=5.4 Hz, 1H), 9.11 (s, 1H), 8.80 (s, 1H), 8.12 (d, J=8.9 Hz, 2H), 7.35 (d, J=2.0 Hz, 1H), 7.09 (dd, J=8.9, 2.1 Hz, 1H), 4.14 (d, J=5.5 Hz, 2H), 3.57 (s, 3H).

Example 45: 2-(7-(2-fluorophenoxy)-4-hydroxy-1-methyl-2-oxo-1,2-dihydroquinoline-3-carboxamido)acetic acid

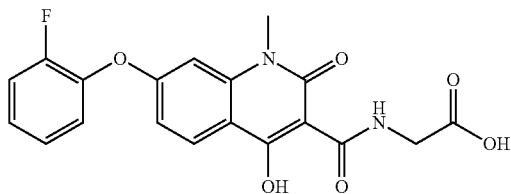 [SMILES: Cn1c(=O)c(C(=O)NCC(=O)O)c(O)c2ccc(Oc3ccccc3F)cc21]

Step 1: methyl 7-(2-fluorophenoxy)-4-hydroxy-1-methyl-2-oxo-1,2-dihydroquinoline-3-carboxylate To a round-bottom flask were added methyl 7-bromo-4-hydroxy-1-methyl-2-oxo-1,2-dihydroquinoline-3-carboxylate (1.00 g, 3.20 mmol), 2-fluorophenol (0.467 g, 4.17 mmol), N,N-dimethylglycine (0.100 g, 0.970 mmol), cuprous iodide (0.123 g, 0.646 mmol), cesium carbonate (2.61 g, 8.01 mmol) and dimethyl sulfoxide (20 mL) in turn under nitrogen protection. The mixture was stirred at 140° C. for 18 h. The mixture was cooled to room temperature and water (30 mL) was added. The resulting mixture was extracted with ethyl acetate (50 mL×3). The combined organic layers were washed successively with water (20 mL×3) and saturated brine (20 mL), dried over anhydrous sodium sulfate, and filtered. The filtrate was concentrated in vacuo to remove the solvent. The residue was purified by column chromatography (PE/EtOAc (v/v)=1/2) to give a white solid (0.640 g, 58.2%).

MS (ESI, pos.ion) m/z: 343.9 (M+1).

Step 2: 2-(7-(2-fluorophenoxy)-4-hydroxy-1-methyl-2-oxo-1,2-dihydroquinoline-3-carboxamido)acetic acid To a round-bottom flask were added methyl 7-(2-fluorophenoxy)-4-hydroxy-1-methyl-2-oxo-1,2-dihydroquinoline-3-carboxylate (0.500 g, 1.46 mmol), sodium glycinate (0.282 g, 2.91 mmol) and ethylene glycol monomethyl ether (50 mL) in turn. The mixture was refluxed for 1 h under nitrogen protection. The mixture was cooled to room temperature and water (80 mL) was added. The mixture was washed with ethyl acetate (20 mL×3), and the aqueous layer was acidified with diluted hydrochloric acid (1 M) to pH 3, then the resulting mixture was filtered. The filter cake was dried in vacuo, which was recrystallized from PE/EtOAc ((v/v)=1/3) to give a white solid (0.550 g, 97.8%).

MS (ESI, pos.ion) m/z: 386.9 (M+1);
$^1$H NMR (400 MHz, DMSO-d$_6$) δ (ppm): 10.46 (t, J=5.5 Hz, 1H), 8.08 (d, J=8.9 Hz, 1H), 7.54-7.44 (m, 1H), 7.43-7.29 (m, 3H), 7.20 (d, J=2.0 Hz, 1H), 6.85 (dd, J=8.9, 2.0 Hz, 1H), 4.13 (d, J=5.5 Hz, 2H), 3.56 (s, 3H).

Example 46: 2-(7-(3-fluorophenoxy)-4-hydroxy-1-methyl-2-oxo-1,2-dihydroquinoline-3-carboxamido)acetic acid

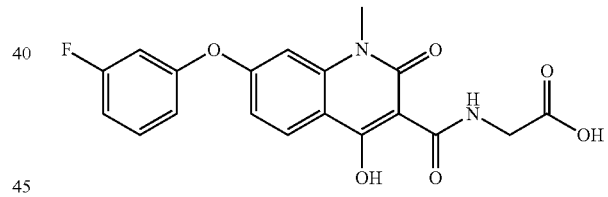

Step 1: methyl 7-(3-fluorophenoxy)-4-hydroxy-1-methyl-2-oxo-1,2-dihydroquinoline-3-carboxylate To a round-bottom flask were added methyl 7-bromo-4-hydroxy-1-methyl-2-oxo-1,2-dihydroquinoline-3-carboxylate (1.00 g, 3.20 mmol), 3-fluorophenol (0.467 g, 4.17 mmol), N,N-dimethylglycine (0.100 g, 0.970 mmol), cuprous iodide (0.123 g, 0.646 mmol), cesium carbonate (2.61 g, 8.01 mmol) and dimethyl sulfoxide (20 mL) in turn under nitrogen protection. The mixture was stirred at 140° C. for 18 h. The mixture was cooled to room temperature and water (30 mL) was added. The resulting mixture was extracted with ethyl acetate (50 mL×3). The combined organic layers were washed successively with water (20 mL×3) and saturated brine (20 mL), dried over anhydrous sodium sulfate and filtered. The filtrate was concentrated in vacuo to remove the solvent. The residue was purified by column chromatography (PE/EtOAc (v/v)=1/2) to give a white solid (0.400 g, 36.4%).

MS (ESI, pos.ion) m/z: 344.0 (M+1).

Step 2: 2-(7-(3-fluorophenoxy)-4-hydroxy-1-methyl-2-oxo-1,2-dihydroquinoline-3-carboxamido) acetic acid To a round-bottom flask were added methyl 7-(3-fluorophenoxy)-4-hydroxy-1-methyl-2-oxo-1,2-dihydroquinoline-3-carboxylate (0.400 g, 1.17 mmol), sodium glycinate (0.227 g, 2.34 mmol) and ethylene glycol monomethyl ether (20 mL) in turn. The mixture was refluxed for 1 h under nitrogen protection. The mixture was cooled to room temperature and concentrated in vacuo to remove the solvent. To the residue was added water (20 mL), and the mixture was extracted with ethyl acetate (20 mL×3). The aqueous layer was acidified with diluted hydrochloric acid (1 M) to pH 3, then the resulting mixture was filtered. The filter cake was dried in vacuo, and then recrystallized from petroleum ether/ethyl acetate ((v/v)=1/3) to give a white solid (0.20 g, 40.0%).

MS (ESI, pos.ion) m/z: 386.9 (M+1);
$^1$H NMR (400 MHz, DMSO-$d_6$) δ (ppm): 10.47 (t, J=5.4 Hz, 1H), 8.10 (d, J=8.8 Hz, 1H), 7.51 (dd, J=15.6, 8.5 Hz, 1H), 7.25 (d, J=2.0 Hz, 1H), 7.15-7.08 (m, 2H), 7.05-7.00 (m, 1H), 6.97 (dd, J=8.9, 2.1 Hz, 1H), 4.13 (d, J=5.5 Hz, 2H), 3.56 (s, 3H).

Example 47: 2-(7-(4-fluorophenoxy)-4-hydroxy-1-methyl-2-oxo-1,2-dihydroquinoline-3-carboxamido) acetic acid

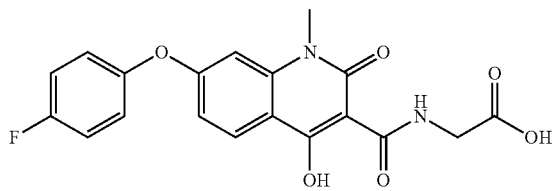 [SMILES: Cn1c(=O)c(C(=O)NCC(=O)O)c(O)c2ccc(Oc3ccc(F)cc3)cc21]

Step 1: methyl 7-(4-fluorophenoxy)-4-hydroxy-1-methyl-2-oxo-1,2-dihydroquinoline-3-carboxylate To a round-bottom flask were added methyl 7-bromo-4-hydroxy-1-methyl-2-oxo-1,2-dihydroquinoline-3-carboxylate (1.00 g, 3.20 mmol), 4-fluorophenol (0.467 g, 4.17 mmol), N,N-dimethylglycine (0.100 g, 0.970 mmol), cuprous iodide (0.123 g, 0.646 mmol), cesium carbonate (2.61 g, 8.01 mmol) and dimethyl sulfoxide (20 mL) in turn under nitrogen protection. The mixture was stirred at 140° C. for 18 h. The mixture was cooled to room temperature and water (30 mL) was added. The resulting mixture was extracted with ethyl acetate (50 mL×3). The combined organic layers were washed successively with water (20 mL×3) and saturated brine (20 mL), dried over anhydrous sodium sulfate and filtered. The filtrate was concentrated in vacuo. The residue was purified by column chromatography (petroleum ether/ethyl acetate (v/v)=1/2) to give a white solid (0.548 g, 49.8%).

MS (ESI, pos.ion) m/z: 343.9 (M+1).

Step 2: 2-(7-(4-fluorophenoxy)-4-hydroxy-1-methyl-2-oxo-1,2-dihydroquinoline-3-carboxamido) acetic acid To a round-bottom flask were added methyl 7-(4-fluorophenoxy)-4-hydroxy-1-methyl-2-oxo-1,2-dihydroquinoline-3-carboxylate (0.500 g, 1.46 mmol), sodium glycinate (0.282 g, 2.91 mmol) and ethylene glycol monomethyl ether (50 mL) in turn. The mixture was refluxed for 1 h under nitrogen protection. The mixture was cooled to room temperature and water (80 mL) was added. The mixture was extracted with ethyl acetate (20 mL×3). The aqueous layer was acidified with diluted hydrochloric acid (1 M) to pH 3, then the resulting mixture was filtered. The filter cake was dried in vacuo, then recrystallized from petroleum ether/ethyl acetate ((v/v)=1/3) to give a white solid (0.148 g, 26.3%).

MS (ESI, pos.ion) m/z: 386.9 (M+1);
$^1$H NMR (400 MHz, DMSO-$d_6$) δ (ppm): 10.46 (t, J=5.5 Hz, 1H), 8.06 (d, J=8.9 Hz, 1H), 7.36-7.29 (m, J=11.8, 5.7 Hz, 2H), 7.29-7.22 (m, 2H), 7.14 (d, J=2.0 Hz, 1H), 6.87 (dd, J=8.9, 2.1 Hz, 1H), 4.13 (d, J=5.5 Hz, 2H), 3.54 (s, 3H).

Example 48: 2-(7-(2-chlorophenoxy)-4-hydroxy-1-methyl-2-oxo-1,2-dihydroquinoline-3-carboxamido) acetic acid

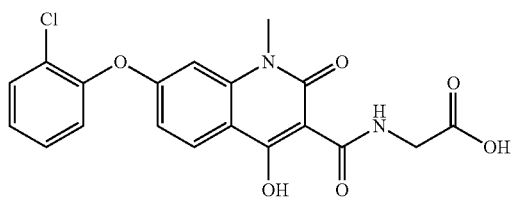

Step 1: methyl 7-(2-chlorophenoxy)-4-hydroxy-1-methyl-2-oxo-1,2-dihydroquinoline-3-carboxylate To a round-bottom flask were added methyl 7-bromo-4-hydroxy-1-methyl-2-oxo-1,2-dihydroquinoline-3-carboxylate (1.00 g, 3.20 mmol), 2-chlorophenol (0.536 g, 4.23 mmol), N,N-dimethylglycine (0.100 g, 0.970 mmol), cuprous iodide (0.123 g, 0.646 mmol), cesium carbonate (2.61 g, 8.01 mmol) and dimethyl sulfoxide (20 mL) in turn under nitrogen protection. The mixture was stirred at 140° C. for 18 h. The mixture was cooled to room temperature and water (30 mL) was added. The resulting mixture was extracted with ethyl acetate (50 mL×3). The combined organic layers were washed successively with water (20 mL×3) and saturated brine (20 mL), dried over anhydrous sodium sulfate and filtered. The filtrate was concentrated in vacuo to remove the solvent. The residue was purified by silica-gel column chromatography (petroleum ether/ethyl acetate (v/v)=1/2) to give a white solid (0.450 g, 39.0%).

MS (ESI, pos.ion) m/z: 359.8 (M+1).

Step 2: 2-(7-(2-chlorophenoxy)-4-hydroxy-1-methyl-2-oxo-1,2-dihydroquinoline-3-carboxamido) acetic acid To a round-bottom flask were added methyl 7-(2-chlorophenoxy)-4-hydroxy-1-methyl-2-oxo-1,2-dihydroquinoline-3-carboxylate (0.450 g, 1.25 mmol), sodium glycinate (0.243 g, 2.50 mmol) and ethylene glycol monomethyl ether (10 mL) in turn. The mixture was refluxed for 2 h under nitrogen protection. The mixture was cooled to room temperature and concentrated in vacuo to remove the solvent. To the residue was added water (20 mL), and the mixture was extracted with ethyl acetate (20 mL×3). The aqueous layer was acidified with diluted hydrochloric acid (1 M) to pH 3, then the resulting mixture was filtered. The filter cake was dried in vacuo, then recrystallized from petroleum ether/ethyl acetate ((v/v)=1/3) to give a white solid (0.250 g, 49.6%).

MS (ESI, pos.ion) m/z: 402.8 (M+1);
$^1$H NMR (400 MHz, DMSO-$d_6$) δ (ppm): 10.46 (t, J=5.4 Hz, 1H), 8.08 (d, J=8.9 Hz, 1H), 7.68 (d, J=7.9 Hz, 1H), 7.52-7.43 (m, 1H), 7.35 (t, J=7.5 Hz, 2H), 7.20 (d, J=1.9 Hz, 1H), 6.78 (dd, J=8.9, 2.1 Hz, 1H), 4.13 (d, J=5.5 Hz, 2H), 3.56 (s, 3H).

Example 49-56

Compounds of examples 49-50 were prepared according to the procedure as described in scheme 3 or example 1 by using suitable reagents.

Compound of example 51 was prepared according to the procedure as described in scheme 3 or example 3 by using suitable reagents.

Compounds of examples 52-55 were prepared according to the procedure as described in scheme 4 or example 7 by using suitable reagents.

Compound of example 56 were prepared according to the procedure as described in scheme 7 or example 10 by using suitable reagents.

| No. | Compound | MS [M − 1]⁻ |
|---|---|---|
| Example 49 | 2-(7-(4-carbamoylphenoxy)-4-hydroxy-1-methyl-2-oxo-1,2-dihydroquinoline-3-carboxamido)acetic acid | 410.2 |
| Example 50 | 2-(6-((2,3-dihydro-1H-inden-2-yl)methyl)-4-hydroxy-1-methyl-2-oxo-1,2-dihydroquinoline-3-carboxamido)acetic acid | 405.2 |
| Example 51 | 2-(4-hydroxy-1-methyl-2-oxo-6-(6-oxo-3-phenyltetrahydropyrimidin-1(2H)-yl)-1,2-dihydroquinoline-3-carboxamido)acetic acid | 449.2 |
| Example 52 | 2-(4-hydroxy-1-methyl-2-oxo-6-phenylsulfonyl-1,2-dihydroquinoline-3-carboxamido)acetic acid | 415.2 |
| Example 53 | 2-(4-hydroxy-1-methyl-6-(naphthalen-1-ylsulfonyl)-2-oxo-1,2-dihydroquinoline-3-carboxamido)acetic acid | 465.1 |
| Example 54 | 2-(4-hydroxy-1-methyl-2-oxo-6-((2-oxoindolin-1-yl)sulfonyl)-1,2-dihydroquinoline-3-carboxamido)acetic acid | 470.2 |
| Example 55 | 2-(4-hydroxy-1-methyl-2-oxo-6-((2-oxopyrrolidin-1-yl)sulfonyl)-1,2-dihydroquinoline-3-carboxamido)acetic acid | 422.2 |
| Example 56 | 2-(5-(2-(benzhydrylamino)-2-oxoethyl)-4-hydroxy-1-methyl-2-oxo-1,2-dihydroquinoline-3-carboxamido)acetic acid | 498.2 |

BIOLOGICAL ASSAYS

Example A: Assays of the Activities of Compounds of the Invention in Inducing Erythropoietin (EPO) Production In Vitro The activities of compounds of the invention in inducing erythropoietin (EPO) production were assessed by using human live cancer cell strain Hep3B (ATCC: American type culture collection, Manassas, Va.). Hep3B cells seeded in a 96-well plate with a density of $2.5×10^4$ cells/well were cultivated overnight in DMEM culture medium (Dulbecco's Modified Eagle's Medium) at 37° C. in the presence of 10% fetal bovine serum (FBS). The next day, the supernatant liquid of culture medium was abandoned by suction, and to the residue was added fresh DMEM (containing 0.5% DMSO, 0.5% FBS) containing compound of the invention with a series of concentrations (0.31160.00 μM) or containing solvent used for comparison. The cells were cultivated at 37° C. for 24 h. The supernatant liquid was collected and the EPO concentration of the supernatant was quantified by using human EPO ELISA kit (Abcam). The activity of each compound in inducing erythropoietin (EPO) production was represented by half maximal effective concentration ($EC_{50}$).

TABLE 2 assays of the acitivities of compounds of the invention in inducing erythropoietin (EPO) production in vitro

| Example Number | $EC_{50}$ (μM) |
|---|---|
| Example 1 | 5.35 |
| Example 2 | 5.00 |
| Example 5 | 4.00 |
| Example 7 | 6.83 |
| Example 8 | 1.63 |
| Example 9 | 2.52 |
| Example 11 | 10.23 |
| Example 12 | 4.24 |
| Example 13 | 7.10 |
| Example 14 | 10.25 |
| Example 15 | 6.92 |
| Example 16 | 8.83 |
| Example 17 | 3.16 |
| Example 18 | 6.28 |
| Example 19 | 2.26 |
| Example 20 | 3.75 |
| Example 21 | 5.75 |
| Example 22 | 4.18 |
| Example 23 | 9.23 |
| Example 24 | 9.53 |

TABLE 2-continued assays of the acitivities of compounds of the invention in inducing erythropoietin (EPO) production in vitro

| Example Number | $EC_{50}$ (μM) |
|---|---|
| Example 25 | 10.15 |
| Example 26 | 13.5 |
| Example 27 | 6.85 |
| Example 28 | 1.51 |
| Example 29 | 10.19 |
| Example 30 | 1.97 |
| Example 31 | 4.15 |
| Example 32 | 3.63 |
| Example 33 | 2.56 |
| Example 34 | 20.2 |
| Example 35 | 2.25 |
| Example 36 | 2.95 |
| Example 37 | 6.26 |
| Example 38 | 8.85 |
| Example 39 | 4.89 |
| Example 40 | 4.06 |
| Example 42 | 3.34 |
| Example 43 | 28.9 |

TABLE 2-continued assays of the acitivities of compounds of the invention in inducing erythropoietin (EPO) production in vitro

| Example Number | EC$_{50}$ (µM) |
|---|---|
| Example 45 | 6.02 |
| Example 46 | 3.61 |
| Example 47 | 3.92 |
| Example 48 | 6.60 |

Conclusion:

Table 2 shows that the compounds of the invention have good activity in inducing EPO production.

Example B: Pharmacokinetic Assays of the Compounds of the Invention

Preparation of test compound solutions: the test compound solution was prepared for oral and intravenous administration by using 5% DMSO, 5% Solutol HS 15 and 90% normal saline.

Male SD rats weighing 190-250 g were randomly divided into two groups, and each group had three rats; one group was administered with test compound at a dose of 1.0 mg/kg by intravenous injection, the other group was administered with test compound at a dose of 5.0 mg/kg by oral. After administering, blood samples were collected at time points of 0.0833, 0.25, 0.5, 1.0, 2.0, 4.0, 7.0 and 24 h. Standard curve was plotted based on concentrations of the samples in a suitable range, and the concentrations of test compounds in plasma samples were determined by using AB SCIEX API4000 LC-MS/MS in MRM mode. Pharmacokinetic parameters were calculated according to drug concentration–time curve using a noncompartmental method with WinNonLin 6.3 software.

TABLE 3

Pharmacokinetic parameters of the compounds of the invention

| No. | administration route | dosage (mg/kg) | AUC$_{last}$ (h * ng/mL) | C$_{max}$ (ng/mL) | T$_{1/2}$ (h) | T$_{max}$ (h) | V$_{ss}$ (L/kg) | Cl (mL/min/kg) | F (%) |
|---|---|---|---|---|---|---|---|---|---|
| Example 1 | iv | 1 | 9340 | 8910 | 7.79 | 0.083 | 0.234 | 1.77 | 81.5 |
| | po | 5 | 38400 | 18400 | 4.2 | 0.667 | N/A | N/A | |
| Example 2 | iv | 1 | 20200 | 7190 | 3.74 | 0.222 | 0.159 | 0.833 | 100.4 |
| | po | 5 | 101000 | 13200 | 3.99 | 2.17 | N/A | N/A | |
| Example 13 | iv | 1 | 13100 | 8480 | 0.959 | 0.083 | 0.107 | 1.32 | 94.6 |
| | po | 5 | 57000 | 12300 | 4.23 | 1.17 | N/A | N/A | |
| Example 19 | iv | 1 | 8260 | 6080 | 1.09 | 0.083 | 0.164 | 2.06 | 98.7 |
| | po | 5 | 41000 | 9560 | 1.4 | 0.50 | N/A | N/A | |
| Example 22 | iv | 1 | 10800 | 10100 | 0.959 | 0.083 | 0.146 | 1.56 | 108.6 |
| | po | 5 | 58700 | 10700 | 2.79 | 0.833 | N/A | N/A | |
| Example 28 | iv | 1 | 6200 | 4170 | 0.99 | 0.083 | 0.217 | 2.67 | 107.8 |
| | po | 5 | 33300 | 11700 | 1.76 | 0.917 | N/A | N/A | |
| Example 47 | iv | 1 | 10200 | 6400 | 1.06 | 0.083 | 0.144 | 1.66 | 90.7 |
| | po | 5 | 46200 | 11500 | 2.64 | 0.5 | N/A | N/A | |

Notes:
iv means intravenous injection; po means oral administration; N/A means "no".

Conclusion:

Table 3 shows that the compounds of the invention have good in vivo pharmacokinetic properties, such as good absorption, high exposure level and high bioavailability.

Reference throughout this specification to "an embodiment," "some embodiments," "one embodiment", "another example," "an example," "a specific examples," or "some examples," means that a particular feature, structure, material, or characteristic described in connection with the embodiment or example is included in at least one embodiment or example of the present disclosure. Thus, the appearances of the phrases such as "in some embodiments," "in one embodiment", "in an embodiment", "in another example, "in an example," "in a specific examples," or "in some examples," in various places throughout this specification are not necessarily referring to the same embodiment or example of the present disclosure. Furthermore, the particular features, structures, materials, or characteristics may be combined in any suitable manner in one or more embodiments or examples. In addition, those skilled in the art can integrate and combine different embodiments, examples or the features of them as long as they are not contradictory to one another.

Although explanatory embodiments have been shown and described, it would be appreciated by those skilled in the art that the above embodiments cannot be construed to limit the present disclosure, and changes, alternatives, and modifications can be made in the embodiments without departing from spirit, principles and scope of the present disclosure.

What is claimed is:

1. A compound having Formula (I) or a stereoisomer, a geometric isomer, a tautomer, an N-oxide, a hydrate, a solvate, a metabolite, an ester, a pharmaceutically acceptable salt or a prodrug thereof,

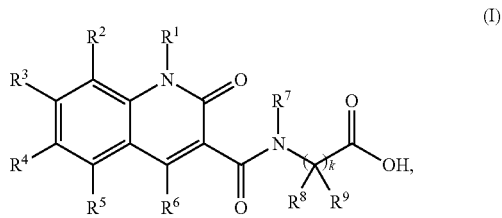

(I)

wherein,

R$^1$ is C$_{1-4}$ alkyl, and wherein C$_{1-4}$ alkyl is optionally substituted with one, two, three or four substituents independently selected from C$_{3-6}$ cycloalkyl, or C$_{2-5}$ heterocyclyl;

each of R$^2$, R$^3$, R$^4$ and R$^5$ is independently H or -L-R$^{10}$, with the proviso that R$^2$, R$^3$, R$^4$ and R$^5$ are not H at the same time;

wherein each L is independently —(CR$^{11}$R$^{12}$)$_p$—O—, —(CR$^{11}$R$^{12}$)$_p$—S(=O)$_n$—, —(CR$^{11}$R$^{12}$)$_p$—N(R$^{13}$)—, or —(CR$^{11}$R$^{12}$)$_p$—C(=X)—;

wherein each X is independently O or S;

each R$^{11}$ and R$^{12}$ is independently H, halogen, cyano, hydroxy, mercapto, C$_{1-6}$ alkyl, C$_{1-6}$ haloalkyl, C$_{1-6}$ alkoxy, C$_{1-6}$ haloalkoxy, C$_{3-10}$ cycloalkyl, C$_{2-9}$ heterocyclyl, C$_{6-10}$ aryl or C$_{1-9}$ heteroaryl, and wherein optionally each of C$_{1-6}$ alkyl, C$_{1-6}$ haloalkyl, C$_{1-6}$ alkoxy, C$_{1-6}$ haloalkoxy, C$_{3-10}$ cycloalkyl, C$_{2-9}$ heterocyclyl, C$_{6-10}$ aryl and C$_{1-9}$ heteroaryl is independently substituted with one, two, three or four substituents independently selected from oxo (=O), halogen, hydroxy, amino, C$_{1-6}$ alkyl, C$_{1-6}$ haloalkyl, C$_{1-6}$ alkoxy, C$_{1-6}$ haloalkoxy, acyl, sulfonyl, C$_{3-8}$ cycloalkyl, C$_{2-7}$ heterocyclyl, C$_{6-10}$ aryl or C$_{1-9}$ heteroaryl;

each R$^{13}$ is independently H, C$_{1-6}$ alkyl, C$_{3-10}$ cycloalkyl, C$_{2-9}$ heterocyclyl, C$_{6-10}$ aryl or C$_{1-9}$ heteroaryl, and wherein optionally each of C$_{1-6}$ alkyl, C$_{3-10}$ cycloalkyl, C$_{2-9}$ heterocyclyl, C$_{6-10}$ aryl and C$_{1-9}$ heteroaryl is independently substituted with one, two, three or four substituents independently selected from oxo (=O), cyano, nitro, halogen, hydroxy, amino, mercapto, C$_{1-6}$ alkyl, C$_{1-6}$ haloalkyl, C$_{1-6}$ alkoxy, C$_{1-6}$ haloalkoxy, acyl, sulfonyl, C$_{3-8}$ cycloalkyl, C$_{2-7}$ heterocyclyl, C$_{6-10}$ aryl or C$_{1-9}$ heteroaryl;

each R$^{10}$ is independently —OR$^{14}$, —NR$^{15}$R$^{16}$, —C(=O)NR$^{15}$R$^{16}$, —N(R$^{15}$)C(=O)R$^{17}$, —C(=O)R$^{17}$, —S(=O)$_n$R$^{18}$, —S(=O)$_2$NR$^{15}$R$^{16}$, —N(R$^{15}$)S(=O)$_2$R$^{18}$, C$_{3-10}$ cycloalkyl, C$_{3-10}$ cycloalkyl-C$_{1-6}$-alkyl, C$_{2-9}$ heterocyclyl, C$_{2-9}$ heterocyclyl-C$_{1-6}$-alkyl, C$_{6-10}$ aryl, C$_{6-10}$ aryl-C$_{1-6}$-alkyl, C$_{1-9}$ heteroaryl or C$_{1-9}$ heteroaryl-C$_{1-6}$-alkyl, and wherein optionally each of C$_{3-10}$ cycloalkyl, C$_{3-10}$ cycloalkyl-C$_{1-6}$-alkyl, C$_{2-9}$ heterocyclyl, C$_{2-9}$ heterocyclyl-C$_{1-6}$-alkyl, C$_{6-10}$ aryl, C$_{6-10}$ aryl-C$_{1-6}$-alkyl, C$_{1-9}$ heteroaryl and C$_{1-9}$ heteroaryl-C$_{1-6}$-alkyl is independently substituted with one, two, three or four substituents independently selected from oxo (=O), halogen, hydroxy, mercapto, amino, nitro, cyano, C$_{1-6}$ alkyl, C$_{1-6}$ haloalkyl, C$_{1-6}$ alkoxy, C$_{1-6}$ haloalkoxy, acyl, sulfonyl, C$_{3-10}$ cycloalkyl, C$_{2-9}$ heterocyclyl, C$_{6-10}$ aryl or C$_{1-9}$ heteroaryl;

wherein each R$^{14}$, R$^{16}$, R$^{17}$ and R$^{18}$ is independently C$_{3-10}$ cycloalkyl, C$_{3-10}$ cycloalkyl-C$_{1-6}$-alkyl, C$_{2-9}$ heterocyclyl, C$_{2-9}$ heterocyclyl-C$_{1-6}$-alkyl, C$_{6-10}$ aryl, C$_{6-10}$ aryl-C$_{1-6}$-alkyl, C$_{1-9}$ heteroaryl or C$_{1-9}$ heteroaryl-C$_{1-6}$-alkyl;

each R$^{15}$ is independently H or C$_{1-6}$ alkyl;

R$^6$ is hydroxy;

R$^7$ is H;

each R$^8$ and R$^9$ is H;

k is 1;

each m is independently 1, 2, 3 or 4;

each n is independently 0, 1 or 2; and each p and q is independently 0, 1, 2, 3 or 4.

2. The compound according to claim 1, wherein
each L is independently —(CR$^{11}$R$^{12}$)$_p$—O—, —(CR$^{11}$R$^{12}$)$_p$—S(=O)$_n$—, or —(CR$^{11}$R$^{12}$)$_p$—N(R$^{13}$)—;

wherein each R$^{11}$ and R$^{12}$ is independently H, fluorine, chlorine, bromine, C$_{1-4}$ alkyl, C$_{1-4}$ haloalkyl, C$_{3-6}$ cycloalkyl, C$_{2-5}$ heterocyclyl, C$_{6-10}$ aryl or C$_{1-5}$ heteroaryl, and wherein optionally each of C$_{1-4}$ alkyl, C$_{1-4}$ haloalkyl, C$_{3-6}$ cycloalkyl, C$_{2-5}$ heterocyclyl, C$_{6-10}$ aryl and C$_{1-5}$ heteroaryl is independently substituted with one, two, three or four substituents independently selected from oxo (=O), fluorine, chlorine, bromine, hydroxy, —NH$_2$, methylamino, dimethylamino, methyl, ethyl, propyl, n-butyl, t-butyl, trifluoromethyl, methoxy, trifluoromethoxy, cyclopropyl, cyclopentyl, cyclohexyl, pyrrolidyl, piperidyl, morpholinyl, phenyl, naphthyl, pyrrolyl, thienyl or pyridyl;

each R$^{13}$ is independently H, C$_{1-4}$ alkyl, C$_{3-6}$ cycloalkyl, C$_{2-5}$ heterocyclyl, C$_{6-10}$ aryl or C$_{1-5}$ heteroaryl, and wherein optionally each of C$_{1-4}$ alkyl, C$_{3-6}$ cycloalkyl, C$_{2-5}$ heterocyclyl, C$_{6-10}$ aryl and C$_{1-5}$ heteroaryl is independently substituted with one, two, three or four substituents independently selected from oxo (=O), cyano, nitro, fluorine, chlorine, bromine, hydroxy, —NH$_2$, methylamino, dimethylamino, methyl, ethyl, propyl, n-butyl, t-butyl, trifluoromethyl, methoxy, trifluoromethoxy, acetyl, methylsulfonyl, cyclopropyl, cyclopentyl, cyclohexyl, pyrrolidyl, piperidyl, morpholinyl, phenyl or pyridyl.

3. The compound according to claim 2, wherein
each L is independently —O—, —S(=O)$_n$—, or —N(R$^{13}$)—;

wherein each R$^{11}$ and R$^{12}$ is independently H, C$_{1-4}$ alkyl, C$_{3-6}$ cycloalkyl, C$_{2-5}$ heterocyclyl, C$_{6-10}$ aryl and C$_{1-5}$ heteroaryl, and wherein optionally each of C$_{1-4}$ alkyl, C$_{3-6}$ cycloalkyl, C$_{2-5}$ heterocyclyl, C$_{6-10}$ aryl and C$_{1-5}$ heteroaryl is independently substituted with one, two, three or four substituents independently selected from fluorine, chlorine, bromine, hydroxy, —NH$_2$, methyl, ethyl, propyl, n-butyl, t-butyl, trifluoromethyl, methoxy, trifluoromethoxy, cyclopropyl, cyclopentyl, cyclohexyl, pyrrolidyl, piperidyl, morpholinyl, phenyl, pyrrolyl or pyridyl;

each R$^{13}$ is independently H or C$_{1-4}$ alkyl, and wherein C$_{1-4}$ alkyl is optionally substituted with one, two, three or four substituents independently selected from cyano, nitro, fluorine, chlorine, bromine, hydroxy, —NH, methylamino, dimethylamino, methyl, ethyl, trifluoromethyl, methoxy, trifluoromethoxy, acetyl, methylsulfonyl, cyclopropyl, cyclopentyl, cyclohexyl, pyrrolidyl, piperidyl, morpholinyl, phenyl or pyridyl.

4. The compound according to claim 1, wherein
each R$^{10}$ is independently C$_{3-8}$ cycloalkyl, C$_{3-8}$ cycloalkyl-C$_{1-4}$-alkyl, C$_{2-7}$ heterocyclyl, C$_{2-7}$ heterocyclyl-C$_{1-4}$-alkyl, C$_{6-10}$ aryl, C$_{6-10}$ aryl-C$_{1-4}$-alkyl, C$_{1-9}$ heteroaryl or C$_{1-9}$ heteroaryl-C$_{1-4}$-alkyl, and wherein optionally each of C$_{3-8}$ cycloalkyl, C$_{3-8}$ cycloalkyl-C$_{1-4}$-alkyl, C$_{2-7}$ heterocyclyl, C$_{2-7}$ heterocyclyl-C$_{1-4}$-alkyl, C$_{6-10}$ aryl, C$_{6-10}$ aryl-C$_{1-4}$-alkyl, C$_{1-9}$ heteroaryl and C$_{1-9}$ heteroaryl-C$_{1-4}$-alkyl is independently substituted with one, two, three or four substituents independently selected from oxo (=O), fluorine, chlorine, bromine, hydroxy, —NH$_2$, methylamino, dimethylamino, nitro, cyano, C$_{1-4}$ alkyl, C$_{1-4}$ haloalkyl, C$_{1-4}$ alkoxy, C$_{1-4}$ haloalkoxy, acyl, sulfonyl, C$_{3-6}$ cycloalkyl, C$_{2-5}$ heterocyclyl, C$_{6-10}$ aryl or C$_{1-9}$ heteroaryl.

5. The compound according to claim 4, wherein
each R$^{10}$ is independently C$_{3-6}$ cycloalkyl, C$_{2-5}$ heterocyclyl, C$_{6-10}$ aryl or C$_{1-9}$ heteroaryl, and wherein optionally each of C$_{3-6}$ cycloalkyl, C$_{2-5}$ heterocyclyl, C$_{6-10}$ aryl and C$_{1-9}$ heteroaryl is independently substituted with one, two, three or four substituents independently selected from oxo (=O), fluorine, chlorine, bromine, hydroxy, —NH$_2$, methylamino, dimethylamino, nitro, cyano, methyl, ethyl, propyl, n-butyl, t-butyl, trifluoromethyl, methoxy, ethoxy, trifluoromethoxy, acetyl, methoxycarbonyl, carbamoyl, methylsulfonyl, aminosulfonyl, methoxysulfonyl, cyclopropyl, cyclohexyl, pyrrolidyl, piperidyl, morpholinyl, oxomorpholinyl, phenyl, naphthyl, pyrrolyl, thienyl, pyridyl, pyrimidyl or quinolyl.

6. The compound according to claim 1 having Formula (II), or a stereoisomer, a geometric isomer, a tautomer, an N-oxide, a hydrate, a solvate, a metabolite, an ester, a pharmaceutically acceptable salt or a prodrug thereof,

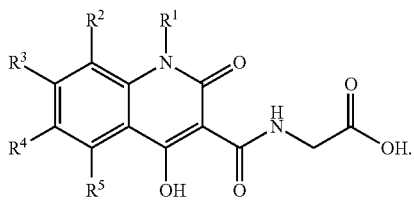

(II)

7. The compound according to claim 1, wherein
each L is independently —O—, —S(=O)$_2$—, —C(=O)N(R$^{13}$)—, —(CR$^{11}$R$^{12}$)—C(=O)N(R$^{13}$)—, or —C(=O)N(R$^{13}$)—(CR$^{11}$R$^{12}$)—;
wherein each R$^{11}$ and R$^{12}$ is independently H, methyl, ethyl, propyl, butyl, cyclopropyl, cyclopentyl, cyclohexyl, pyrrolidyl, piperidyl, morpholinyl, phenyl or pyridyl, and wherein optionally each of methyl, ethyl, propyl, butyl, cyclopyl, cyclopentyl, cyclohexyl, pyrrolidyl, piperidyl, morpholinyl, phenyl and pyridyl is independently substituted with one, two, three or four substituents independently selected from fluorine, chlorine, bromine, hydroxy, —NH$_2$, methylamino, dimethylamino, methyl, ethyl, trifluoromethyl, methoxy or trifluoromethoxy; and
each R$^{13}$ is independently H, methyl, ethyl, propyl or butyl.

8. The compound according to claim 1, wherein
each R$^{10}$ is independently cyclopyl, cyclopentyl, cyclohexyl, oxiranyl, pyrrolidyl, pyrazolidyl, oxazolidinyl, piperidyl, morpholinyl, tetrahydropyrimidinyl, piperazinyl, oxazinanyl, phenyl, 2,3-dihydro-1H-indenyl, naphthyl, pyrrolyl, pyrazolyl, furyl, imidazolyl, oxazolyl, thienyl, thiazolyl, pyridinyl, pyrimidinyl, indolyl, dihydroindolyl, quinolyl, isoquinolyl, quinazolinyl, imidazopyridinyl, benzimidazolyl, benzofuranyl or benzothienyl, and wherein optionally each of cyclopyl, cyclopentyl, cyclohexyl, oxiranyl, pyrrolidyl, pyrazolidyl, oxazolidinyl, piperidyl, morpholinyl, tetrahydropyrimidinyl, piperazinyl, oxazinanyl, phenyl, 2,3-dihydro-1H-indenyl, naphthyl, pyrrolyl, pyrazolyl, furyl, imidazolyl, oxazolyl, thienyl, thiazolyl, pyridinyl, pyrimidinyl, indolyl, dihydroindolyl, quinolyl, isoquinolyl, quinazolinyl, imidazopyridinyl, benzimidazolyl, benzofuranyl and benzothienyl is independently substituted with one, two, three or four substituents independently selected from oxo (=O), fluorine, chlorine, bromine, hydroxy, —NH$_2$, methylamino, dimethylamino, nitro, cyano, methyl, ethyl, propyl, n-butyl, t-butyl, trifluoromethyl, methoxy, ethoxy, trifluoromethoxy, acetyl, methoxycarbonyl, carbamoyl, methylsulfonyl, aminosulfonyl, methoxysulfonyl, cyclopyl, cyclopentyl, cyclohexyl, pyrrolidyl, piperidyl, morpholinyl, oxomorpholinyl, phenyl, pyrrolyl, thienyl or pyridyl.

9. The compound according to claim 1 having one of the following structures:

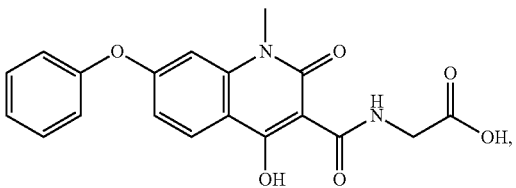

(1)

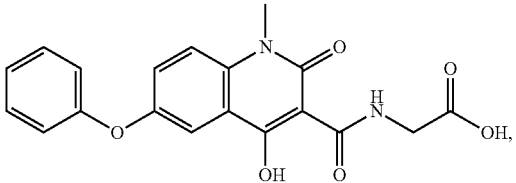

(2)

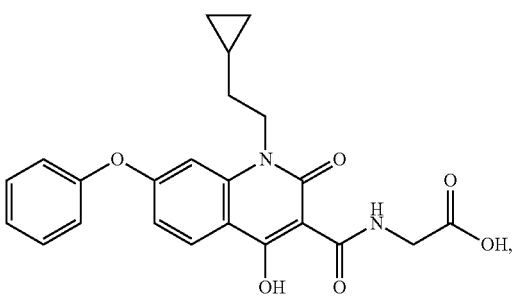

(3)

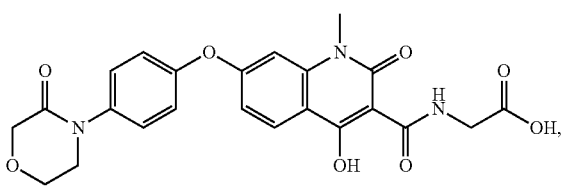

(4)

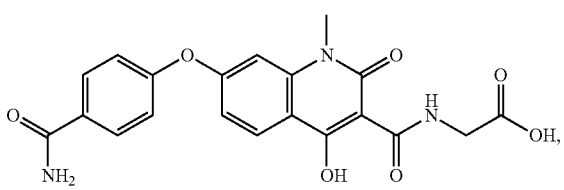

(5)

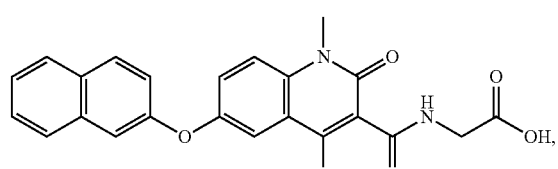

(6)

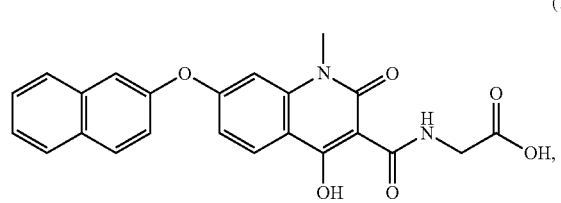

(7)

(14)
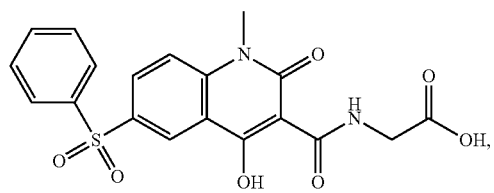
(15)
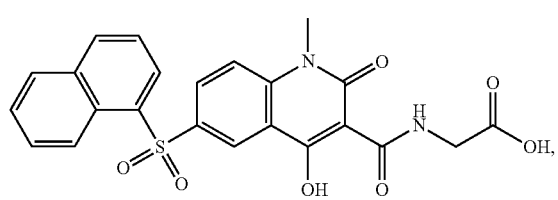
(16)
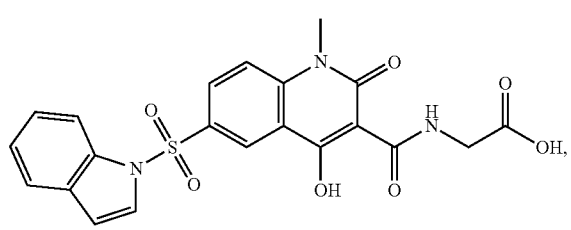
(17)
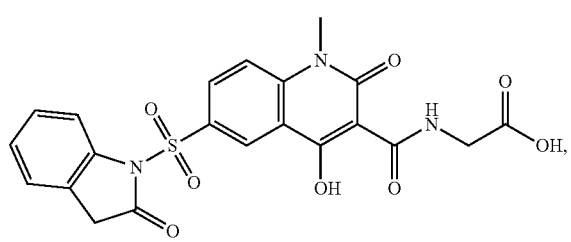
(18)
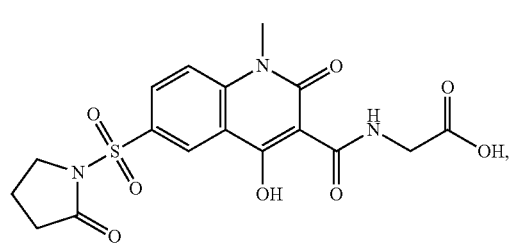
(20)
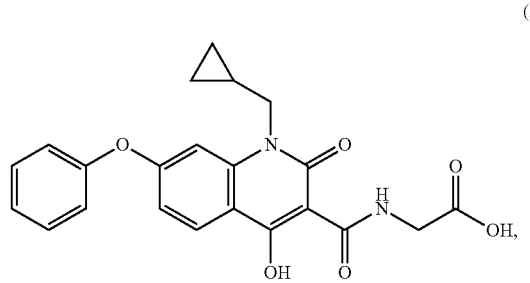
(21)
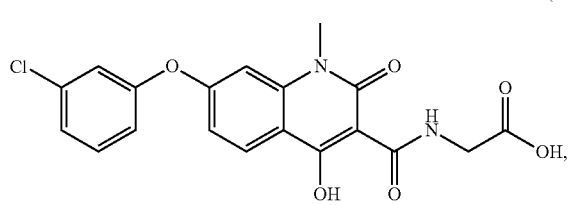
(22)
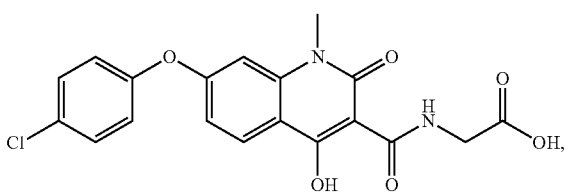
(23)
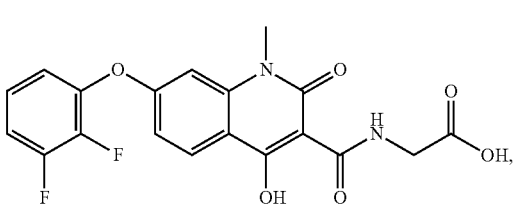
(24)
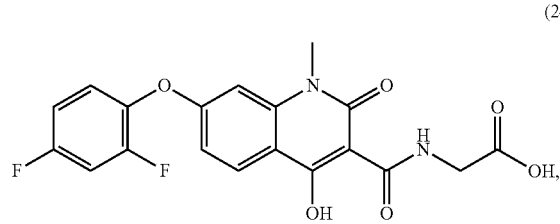
(25)
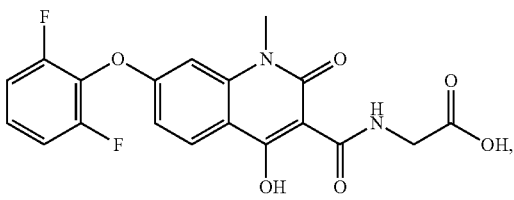
(26)
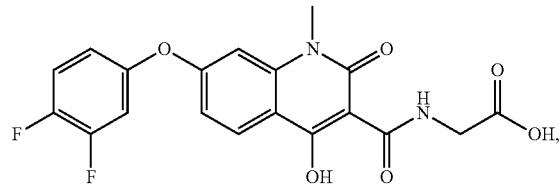
(27)
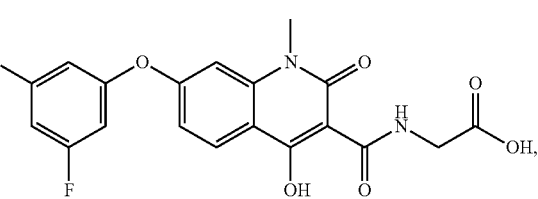
(28)
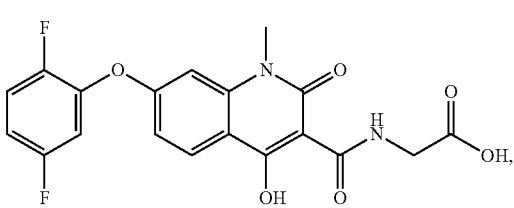

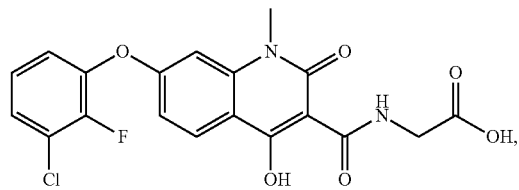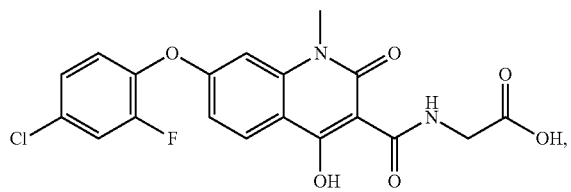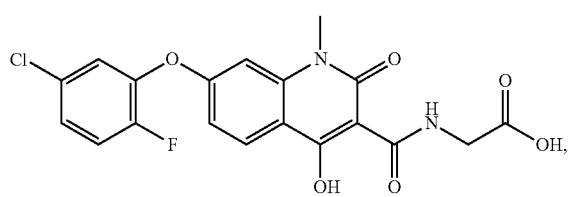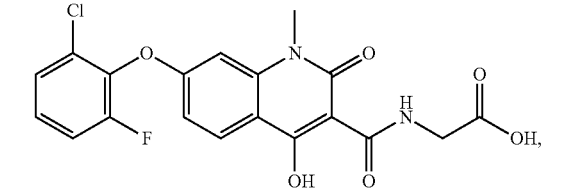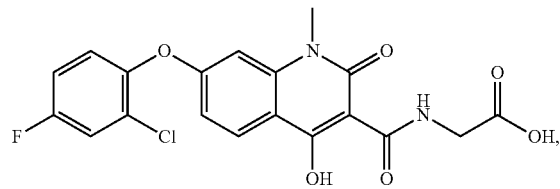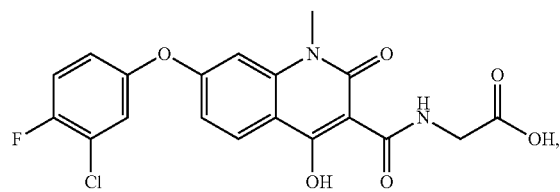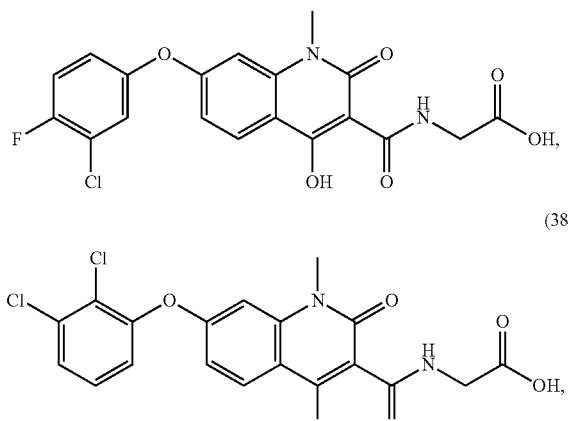

(43)
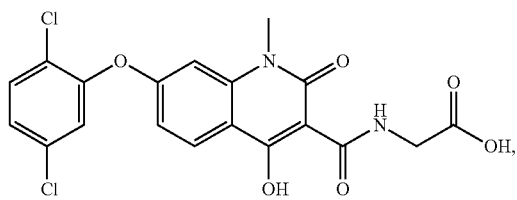
(44)
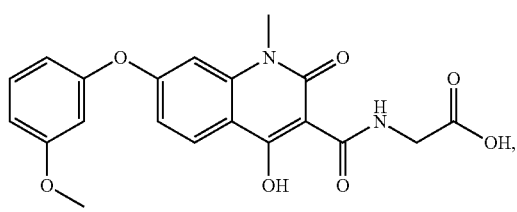
(45)
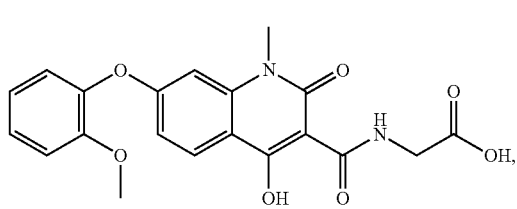
(46)
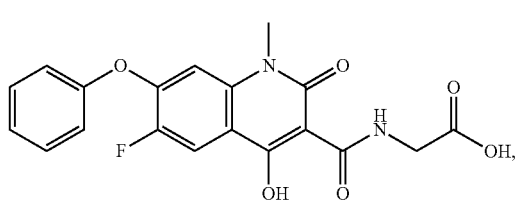
(47)
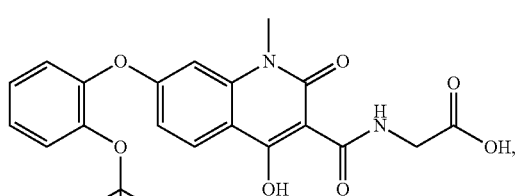
(48)
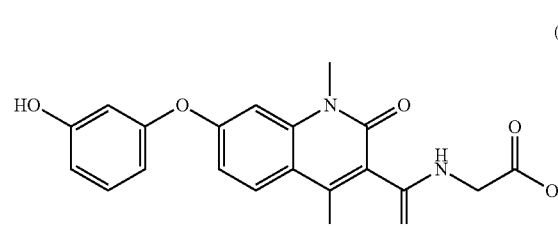
(49)
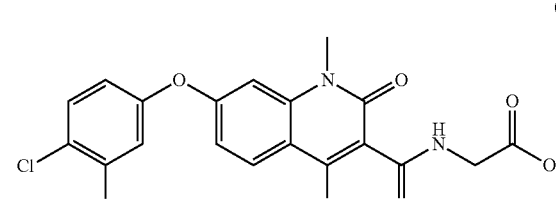
(50)
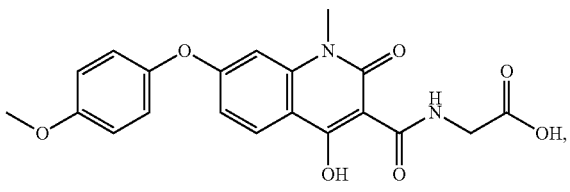
(51)
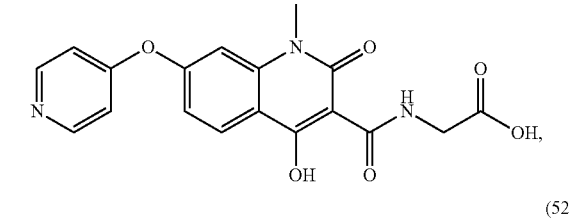
(52)
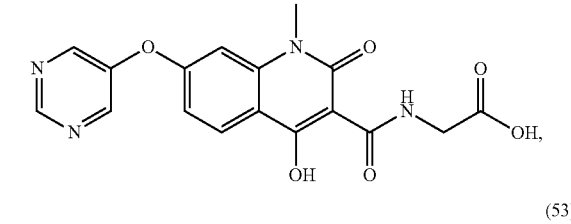
(53)
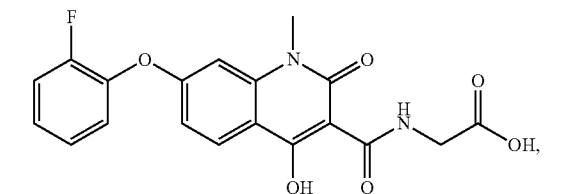
(54)
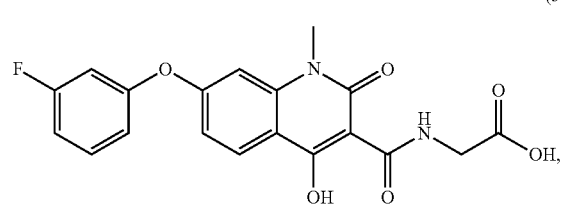
(55)
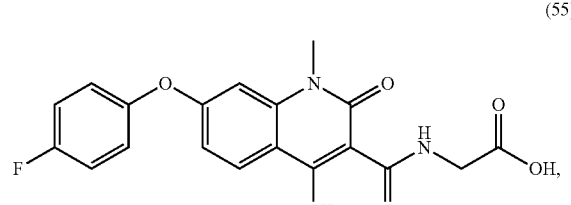
(56)
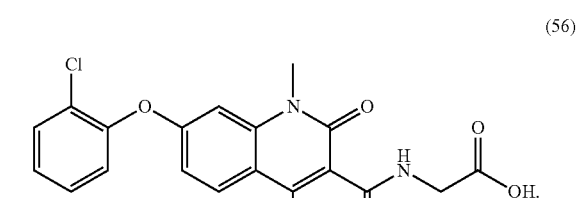
10. A pharmaceutical composition comprising the compound according to claim 1.

11. The pharmaceutical composition according to claim 10 further comprising at least one of pharmaceutically acceptable carriers, excipients, diluents, adjuvants and vehicles.

12. A method for treating or lessening a disease related to hypoxia inducible factor and/or erythropoietin in a patient comprising administering to the patient a therapeutically effective amount of the compound according to claim 1, wherein the disease is anemia, ischemia, a vascular disease, angina pectoris, myocardial ischemia, myocardial infarction, or wound healing.

13. A method for treating or lessening a disease related to hypoxia inducible factor and/or erythropoietin in a patient comprising administering to the patient a therapeutically effective amount of the pharmaceutical composition according to claim 10, wherein the disease is anemia, ischemia, a vascular disease, angina pectoris, myocardial ischemia, myocardial infarction, or wound healing.

* * * * *